US007014994B1

(12) United States Patent
Barany et al.

(10) Patent No.: US 7,014,994 B1
(45) Date of Patent: Mar. 21, 2006

(54) COUPLED POLYMERASE CHAIN REACTION-RESTRICTION-ENDONUCLEASE DIGESTION-LIGASE DETECTION REACTION PROCESS

(75) Inventors: Francis Barany, New York, NY (US); Joseph P. Day, Pacifica, CA (US); Robert P. Hammer, Baton Rouge, LA (US); Donald E. Bergstrom, West Lafayette, IN (US)

(73) Assignees: Cornell Research Foundation, Inc., Ithaca, NY (US); Purdue Research Foundation, West Lafayette, IN (US); Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 09/528,014

(22) Filed: Mar. 17, 2000

Related U.S. Application Data

(60) Provisional application No. 60/125,251, filed on Mar. 19, 1999.

(51) Int. Cl.
*C12Q 1/68* (2006.01)
*C12P 19/34* (2006.01)
*C07H 21/04* (2006.01)

(52) U.S. Cl. .................. 435/6; 435/91.1; 435/91.2; 435/183; 536/23.1; 536/24.3; 536/25.32

(58) Field of Classification Search .............. 435/6, 435/91.2, 91.1, 183; 536/24.3, 23.1, 25, 536/32
See application file for complete search history.

(56) References Cited

U.S. PATENT DOCUMENTS

| | | |
|---|---|---|
| 4,683,202 A | 7/1987 | Mullis |
| 4,749,647 A | 6/1988 | Thomas et al. |
| 4,883,750 A | 11/1989 | Whiteley et al. |
| 4,889,818 A | 12/1989 | Gelfand et al. |
| 4,988,617 A | 1/1991 | Landegren et al. |
| 5,035,996 A | 7/1991 | Hartley |
| 5,143,854 A | 9/1992 | Pirrung et al. |
| 5,202,231 A | 4/1993 | Drmanac et al. |
| 5,242,794 A | 9/1993 | Whiteley et al. |
| 5,258,506 A | 11/1993 | Urdea et al. |
| 5,278,298 A | 1/1994 | Chakraborty et al. |
| 5,288,468 A | 2/1994 | Church et al. |
| 5,290,925 A | 3/1994 | Fino |
| 5,304,487 A | 4/1994 | Wilding et al. |
| 5,314,809 A | 5/1994 | Erlich et al. |
| 5,324,633 A | 6/1994 | Fodor et al. |
| 5,352,582 A | 10/1994 | Lichtenwalter et al. |
| 5,371,241 A | 12/1994 | Brush |
| 5,391,480 A | 2/1995 | Davis et al. |
| 5,405,783 A | 4/1995 | Pirrung et al. |
| 5,407,798 A | 4/1995 | Martinelli et al. |
| 5,412,087 A | 5/1995 | McGall et al. |
| 5,415,839 A | 5/1995 | Zaun et al. |
| 5,424,186 A | 6/1995 | Fodor et al. |
| 5,470,705 A | 11/1995 | Grossman et al. |
| 5,494,810 A | 2/1996 | Barany et al. |
| 5,496,699 A | 3/1996 | Sorenson |
| 5,506,137 A | 4/1996 | Mathur et al. |
| 5,516,635 A | 5/1996 | Ekins et al. |
| 5,516,663 A | 5/1996 | Backman et al. |
| 5,525,464 A | 6/1996 | Drmanac et al. |
| 5,536,649 A | 7/1996 | Fraiser et al. |
| 5,593,840 A | 1/1997 | Bhatnagar et al. |
| 5,648,213 A | 7/1997 | Reddy et al. |
| 5,667,974 A | 9/1997 | Birkenmeyer et al. |
| 5,695,934 A | 12/1997 | Brenner |
| 5,731,171 A | 3/1998 | Bohlander |
| 5,744,305 A | 4/1998 | Fodor et al. |
| 5,800,984 A | 9/1998 | Vary |
| 5,830,711 A | 11/1998 | Barany et al. |
| 5,834,181 A | 11/1998 | Shuber |
| 5,858,659 A | 1/1999 | Sapolsky et al. |
| 5,859,221 A * | 1/1999 | Cook et al. ............... 536/23.1 |
| 5,869,252 A | 2/1999 | Bouma et al. |
| 5,888,731 A | 3/1999 | Yager et al. |
| 5,912,148 A | 6/1999 | Eggerding |
| 5,981,176 A | 11/1999 | Wallace |
| 6,013,445 A | 1/2000 | Albrecht et al. |
| 6,013,513 A | 1/2000 | Reber et al. |

(Continued)

FOREIGN PATENT DOCUMENTS

AU 730633 3/2001

(Continued)

OTHER PUBLICATIONS

Jacobson et al. "A highly sensitive assay for mutant ras genes and its application ot the study of presentation and relapse genotypes in acute leukemia" Oncogene, 1994, 9: 553-563.*

(Continued)

*Primary Examiner*—BJ Forman
(74) *Attorney, Agent, or Firm*—Nixon Peabody LLP

(57) ABSTRACT

The present invention provides a method for identifying one or more low abundance sequences differing by one or more single-base changes, insertions, or deletions, from a high abundance sequence in a plurality of target nucleotide sequences. The high abundance wild-type sequence is selectively removed using high fidelity polymerase chain reaction analog conversion, facilitated by optimal buffer conditions, to create a restriction endonuclease site in the high abundance wild-type gene, but not in the low abundance mutant gene. This allows for digestion of the high abundance DNA. Subsequently the low abundant mutant DNA is amplified and detected by the ligase detection reaction assay. The present invention also relates to a kit for carrying out this procedure.

17 Claims, 19 Drawing Sheets

U.S. PATENT DOCUMENTS

| | | | |
|---|---|---|---|
| 6,020,124 | A | 2/2000 | Sorenson |
| 6,025,139 | A | 2/2000 | Yager et al. |
| 6,027,889 | A | 2/2000 | Barany et al. |
| 6,033,880 | A | 3/2000 | Haff et al. |
| 6,054,564 | A | 4/2000 | Barany |
| 6,143,495 | A | 11/2000 | Lizardi et al. |
| 6,268,148 | B1 | 7/2001 | Barany et al. |

FOREIGN PATENT DOCUMENTS

| | | |
|---|---|---|
| CA | 2049879 | 3/1992 |
| EP | 0 130 515 A2 | 9/1985 |
| EP | 0 185 494 A3 | 6/1986 |
| EP | 0 236 069 A2 | 9/1987 |
| EP | 0 246 864 A2 | 11/1987 |
| EP | 0 320 308 A2 | 6/1989 |
| EP | 0 324 616 A2 | 7/1989 |
| EP | 0 336 731 A2 | 10/1989 |
| EP | 0 373 962 A2 | 6/1990 |
| EP | 0 439 182 A2 | 7/1991 |
| EP | 0 473 155 A2 | 3/1992 |
| EP | 0 601 714 A1 | 6/1994 |
| WO | WO 89/09835 | 10/1989 |
| WO | WO 89/10977 | 11/1989 |
| WO | WO 90/11372 | 10/1990 |
| WO | WO 90/15070 | 12/1990 |
| WO | WO 91/17239 | 11/1991 |
| WO | WO 92/10566 | 6/1992 |
| WO | WO 92/10588 | 6/1992 |
| WO | WO 92/16655 | 10/1992 |
| WO | WO 93/17126 | 9/1993 |
| WO | WO 93/20236 | 10/1993 |
| WO | WO 93/25563 | 12/1993 |
| WO | WO 94/09022 | 4/1994 |
| WO | WO 94/11530 | 5/1994 |
| WO | WO 94/17206 | 8/1994 |
| WO | WO 94/17210 | 8/1994 |
| WO | WO 96/06190 | 2/1996 |
| WO | WO 96/15262 | 5/1996 |
| WO | WO 97/31256 | 8/1997 |
| WO | WO-97/31256 A2 * | 8/1997 |
| WO | WO 98/03673 | 1/1998 |

OTHER PUBLICATIONS

Day et al. "Detection of steroid 21-hydroxylase alleles using gene-specific PCR and a multiplexed ligation detection reaction" Genomics, 1995, 29: 152-162.*

O'Dell et al., "CpG-PCR Combined With Sample Pooling and Mutant Enrichment for CpG Mutation Screening in Population Studies," *Clinical Chem.*, 44:183-185 (1998).

Jacobson et al., Rapid, Nonradioactive Screening for Activating *ras* Oncogene Mutations Using PCR-Primer Introduced Restriction Analysis (PCR-PIRA), *PCR Methods and Applications*, Cold Spring Harbor, NY, 1:146-148 (1991).

Day et al., "Nucleotide Analogs and New Buffers Improve a Generalized Method to Enrich for Low Abundance Mutations," *Nucl. Acids Res.*, 27(8):1819-1830 (1999).

Watson et al., "In Vitro Mutagenesis," *Recombinant DNA*, Second Edition, New York, New York: W. H. Freeman and Company, pp. 191-194 (1983).

Takahashi et al., "Thermophilic DNA Ligase—Purification and Properties of the Enzyme from *Thermus thermophilus* HB8," *J. Biol. Chem.* 259(16):10041-10047 (1984).

Saiki et al., "Enzymatic Amplification of β-Globin Genomic Sequences and Restriction Site Analysis for Diagnosis of Sickle Cell Anemia," *Science* 230:1350-1354 (1985).

Saiki et al., "Primer-Directed Enzymatic Amplification of DNA with a Thermostable DNA Polymerase," *Science* 239:487-491 (1988).

Kumar et al., "Oncogene Detection at the Single Cell Level," *Oncogene* 3(6):647-651 (1988).

Landegren et al., "A Ligase-Mediated Gene Detection Technique," *Science* 241:1077-1080 (1988).

Landegren et al., "DNA Diagnostics—Molecular Techniques and Automation," *Science* 242:229-237 (1988).

Iovannisci et al., "Ligation Amplification and Fluorescence Detection of Mycobacterium Tuberculosis DNA," *Mol. Cell. Probes* 7(1):35-43 (1993).

Wu et al., "The Ligation Amplification Reaction (LAR)-Amplification of Specific DNA Sequences Using Sequential Rounds of Template-Dependent Ligation," *Genomics* 4:560-569 (1989).

Darnell et al., "Manipulating Macromolecules," *Molecular Cell Biology*, Second Edition, New York, New York: W. H. Freeman and Company, pp. 189-225 (1990).

Eckert et al., "High Fidelity DNA Synthesis by the *Thermus aquaticus* DNA Polymerase," *Nucleic Acids Res.* 18(13):3739-3744 (1990).

Kwok et al., "Effects of Primer-Template Mismatches on the Polymerase Chain Reaction: Human Immunodeficiency Virus Type 1 Model Studies," *Nucleic Acids Res.* 18(4):999-1005 (1990).

Suzuki et al., "Detection of Ras Gene Mutations in Human Lung Cancers by Single-Strand Conformation Polymorphism Analysis of Polymerase Chain Reaction Products," *Oncogene* 5:1037-1043 (1990).

Barany, "Genetic Disease Detection and DNA Amplification Using Cloned Thermostable Ligase," *Proc. Nat'l. Acad. Sci. USA* 88:189-193 (1991).

Barany, "The Ligase Chain Reaction in a PCR World," *PCR Methods and Applications* 1:5-16 (1991).

Eckert et al., "DNA Polymerase Fidelity and the Polymerase Chain Reaction," *PCR Methods and Applications* 1(1):17-24 (1991).

Erlich et al., "Recent Advances in the Polymerase Chain Reaction," *Science* 252:1643-1651 (1991).

Kuppuswamy et al., "Single Nucleotide Primer Extension to Detect Genetic Diseases: Experimental Application to Hemophilia B (Factor IX) and Cystic Fibrosis Genes," *Proc. Natl. Acad. Sci. USA* 88:1143-1147 (1991).

Mitsudomi et al., "Mutations of ras Genes Distinguish a Subset of Non-Small-Cell Lung Cancer Cell Lines from Small-Cell Lung Cancer Cell Lines," *Oncogene* 6:1353-1362 (1991).

Tada et al., "Clinical Application of ras Gene Mutation for Diagnosis of Pancreatic Adenocarcinoma," *Gastroent.* 100:233-238 (1991).

Winn-Deen et al., "Sensitive Fluorescence Method for Detecting DNA Ligation Amplification Products," *Clinical Chemistry* 37(9):1522-1523 (1991).

Anderson et al., "Prevalence of RAS Oncogene Mutation in Head and Neck Carcinomas," *The Journal of Otolaryngology* 21(5):321-326 (1992).

Devlin, "Textbook of Biochemistry, with clinical correlations," A Wiley Medical publication, pp. 985-995 (1982).

Sandy et al., "Genotypic Analysis of Mutations in Taq I Restriction Recognition Sites by Restriction Fragment Length Polymorphism/Polymerase Chain Reaction," *Proc. Natl. Acad. Sci. USA* 89:890-894 (1992).

Sidransky et al., "Identification of ras Oncogene Mutations in the Stool of Patients with Curable Colorectal Tumors," *Science* 256:102-105 (1992).

Bottema et al., "PCR Amplification Of Specific Alleles: Rapid Detection of Known Mutations and Polymorphisms," *Mutation Research* 288(1):93-102 (1993).

Cariello et al., "Mutational Analysis Using Denaturing Gradient Gel Electrophoresis and PCR," *Mutation Research* 288:103-112 (1993).

Cotton, "Current Methods of Mutation Detection," *Mutation Research* 285(1):125-144 (1993).

Fan et al., "Limitations in the Use of SSCP Analysis," *Mutation Research* 288:85-92 (1993).

Lu et al., "Quantitative Aspects of the Mutant Analysis by PCR and Restriction Enzyme Cleavage (MAPREC)" *PCR Methods and Appl.* 3:176-180 (1993).

Pourzand et al., "Genotypic Mutation Analysis by RFLP/PCR," *Mutation Research* 288(1):113-121 (1993).

Powell et al., "Molecular Diagnosis of Familial Adenomatous Polyposis," *The New England Journal of Medicine* 329(27):1982-1987 (1993).

Rust et al., "Mutagenically Separated PCR (MS-PCR): A Highly Specific One Step Procedure for Easy Mutation Detection," *Nucl. Acids Res.* 21(16):3623-3629 (1993).

New England Biolabs Catlog, p. 63, Beverly, MA, 1986.

Balles et al., "Facilitated Isolation of Rare Recombinants by Ligase Chain Reaction: Selection for Intragenic Crossover Events in the *Drosophila optomotor-blind* Gene," *Molec. Gen. Genet.* 245:734-740 (1994).

Barnes, "PCR Amplification of Up To 35-kb DNA With High Fidelity and High Yield From λ Bacteriophage Templates," *Proc. Natl. Acad. Sci. USA* 91(6):2216-2220 (1994).

Cheng et al., Effective Amplification of Long Targets From Cloned Inserts and Human Genomic DNA, *Proc. Natl. Acad. Sci. USA* 91(12):5695-5699 (1994).

Grossman et al., "High-Density Multiplex Detection of Nucleic Acid Sequences: Oligonucleotide Ligation Assay and Sequence-Coded Separation," *Nucleic Acids Research* 22(21):4527-4534 (1994).

Hayashi et al., "Genetic Diagnosis Identifies Occult Lymph Node Metastases Undetectable by the Histopathological Method," *Cancer Res.* 54:3853-3856 (1994).

Jen et al., "Molecular Determinants of Dysplasia in Colorectal Lesions," *Cancer Res.* 54:5523-5526 (1994).

Abravaya et al., "Detection of Point Mutations With a Modified Ligase Chain Reaction (Gap-LCR)," *Nucleic Acids Research* 23(4):675-682 (1995).

Berthélemy et al., "Brief Communications—Identification of K-ras Mutations in Pancreatic Juice in the Early Diagnosis of Pancreatic Cancer," *Annals of Internal Medicine* 123(3):188-191 (1995).

Brennan et al., "Molecular Assessment of Histopathological Staging in Squamous-Cell Carcinoma of the Head and Neck," *New England Journal of Medicine* 332(7):429-435 (1995).

Day et al., "Detection Of Steroid 21-Hydroxylase Alleles Using Gene-Specific PCR and a Multiplexed Ligation Detection Reaction," *Genomics* 29:152-162 (1995).

Frenkel, "Specific, Sensitive, and Rapid Assay for Human Immunodeficiency Virus Type I pol Mutations Associated with Resistance to Zidovudine and Didanosine," *Journal of Clinical Microbiology* 33(2):342-347 (1995).

Redston et al., "Common Occurrence of APC and K-ras Gene Mutations in the Spectrum of Colitis-Associated Neoplasias," *Gastroenterology* 108:383-392 (1995).

Luo et al., "Improving the Fidelity of *Thermus thermophilus* DNA Ligase," *Nucleic Acids Research* 24(14):3071-3078 (1996).

O'Dell et al., "PCR Induction of a TaqI Restriction Site at Any CpG Dinucleotide Using Two Mismatched Primers (CpG-PCR)," *Genome Research* 6(6):558-568 (1996).

Sang et al., "Generation of Site-Directed Mutagenesis by Extralong, High-Fidelity Polymerase Chain Reaction," *Analytical Biochemistry* 233(1):142-144 (1996).

Khanna et al., "Multiplex PCR/LDR for Detection of K-ras Mutations in Primary Colon Tumors," *Oncogene* 18:27-38 (1999).

Cha et al., "Mismatch Amplification Mutation Assay (MAMA): Application to the c-H-ras Gene," *PCR Methods Appl.* 2(1):14-20 (1992).

Haliassos et al., "Detection of Minority Point Mutations by Modified PCR Technique: A New Approach for a Sensitive Diagnosis of Tumor-Progression Markers," *Nucleic Acids Res.* 17:8093-8099 (1989).

Chen et al., "A Nonradioactive, Allele-Specific Polymerase Chain Reaction for Reproducible Detection of Rare Mutations in Large Amounts of Genomic DNA: Application to Human K-Ras," *Anal. Biochem.* 244:191-194 (1997).

Kumar et al., "Designed Diagnostic Restriction Fragment Length Polymorphisms for the Detection of Point Mutations in ras Oncogenes," *Oncogene Res.* 4(3):235-241 (1989).

Jacobson et al., "A Highly Sensitive Assay for Mutant *ras* Genes and its Application to the Study of Presentation and Relapse Genotypes in Acute Leukemia," *Oncogene* 9(2):553-563 (1994).

Chen et al., "A Method to Detect ras Point Mutations in Small Subpopulations of Cells," *Anal. Biochem.* 195(1):51-56 (1991).

DiGiuseppe et al., "Detection of K-ras Mutations in Mucinous Pancreatic Duct Hyperplasia from a Patient with a Family History of Pancreatic Carcinoma," *Am. J. Pathol.* 144(5):889-895 (1994).

Kahn et al., "Rapid and Sensitive Nonradioactive Detection of Mutant K-ras Genes Via 'Enriched' PCR Amplification," *Oncogene* 6:1079-1083 (1991).

Levi et al., "Multiple K-ras Codon 12 Mutations in Cholangiocarcinomas Demonstrated with a Sensitive Polymerase Chain Reaction Technique," *Cancer Research* 51(Jul.):3497-3502 (1991).

Hattori et al., "Mismatch PCR RFLP Detection of DRD2 SER311CYS Polymorphism and Schizophrenia," *Biochem. Biophys. Res. Commun.* 202(2):757-763 (1994).

Hodaňová et al., "Incorrect Assignment of N370S Mutation Status by Mismatched PCR/RFLP Method in Two Gaucher Patients," *J. Inherit. Metab. Dis.* 20(4):611-612 (1997).

Hoops et al., "Template Directed Incorporation of Nucleotide Mixtures Using Azole-Nucleobase Analogs," *Nucleic Acids Res.* 25(24):4866-4871 (1997).

Brown et al., "Synthesis and Duplex Stability of Oligonucleotides Containing Adenine-Guanine Analogues," *Carbohydrate Research* 216:129-139 (1991).

Bergstrom et al., "Design and Synthesis of Heterocyclic Carboxamides as Natural Nucleic Acid Base Mimics," *Nucleosides and Nucleotides* 15(1-3):59-68 (1996).

Bergstrom et al., "Synthesis, Structure, and Deoxyribonucleic Acid Sequenceing with a Universal Nucleoside: 1-(2'-Deoxy-β-D-Ribofuranosyl)-3-nitropyrrole," *J. Am. Chem. Soc.* 117:1201-1209 (1995).

Zhang et al., "Exploratory Studies on Azole Carboxamides as Nucleobase Analogs: Thermal Denaturation Studies on Oligodeoxyribonucleotide Duplexes Containing Pyrrole-3-Carboxamide," *Nucleic Acids Res.* 26:2208-2215 (1998).

Hill et al., "Polymerase Recognition of Synthetic Oligodeoxyribonucleotides Incorporating Degenerate Pyrimidine and Purine Bases," *Proc. Natl. Acad. Sci. USA* 95(8):4258-4263 (1998).

Cline et al., "PCR Fidelity of Pfu DNA Polymerase and Other Thermostable DNA Polymerases," *Nucleic Acids Res.* 24(18):3546-3451 (1996).

Brail et al., "Improved Polymerase Fidelity in PCR-SS-CPA," *Mutat. Res.* 303(4):171-175 (1993).

Gotoda et al., "Detection of Three Separate DNA Polymorphisms in the Human Lipoprotein Lipase Gene by Gene Amplification and Restriction Endonuclease Digestion," *J. Lipid Res.* 33(7):1067-1072 (1992).

Athma et al., "Single Base Polymorphism Linked to the Ataxia-Telangiectasia Locus is Detected by Mismatch PCR," *Biochem. and Biophys. Res. Commun.* 210(3):982-986 (1995).

Celi et al., "A Rapid and Versatile Method to Synthesize Internal Standards for Competitive PCR," *Nucleic Acids Research* 21(4):1047 (1993).

Wiedmann et al., "Ligase Chain Reaction (LCR)-Overview and Applications," *PCR Methods and Applications* CSH Laboratory Press, S51-S64 (1994).

Mao et al., "Microsatellite Alterations as Clonal Markers for the Detection of Human Cancer," *Proc. Natl. Acad. Sci. USA* 91:9871-9875 (1994).

Mao et al., "Molecular Detection of Primary Bladder Cancer by Microsatellite Analysis," *Science* 271:659-662 (1996).

Radford et al., "Allelotyping of Ductal Carcinoma in Situ of the Breast: Deletion of Loci on 8p, 13q, 16q, 17p and 171q" *Cancer Research* 55:3399-3405 (1995).

Cawkwell et al., "Frequency of Allele Loss of DCC, p53, RBI, WTI, NFI, NM23 and PC/MCC in Colorectal Cancer Assayed by Fluorescent Multiplex Polymerase Chain Reaction," *Br. J. Cancer,* 70(5):813-818 (1994).

Reed et al., "Chromosome-Specific Microsatellite Sets for Fluorescence-Based, Semi-Automated Genome Mapping," *Nature Genetics* 7:390-395 (1994).

Syvänen et al., "Identification of Individuals by Analysis of Biallelic DNA Markers, Using PCR and Solid-Phase Minisequencing," *Am. J. Hum. Genet.* 52:46-59 (1993).

Deng et al., "An Improved Method of Competitive PCR for Quantitation of Gene Copy Number," *Nucleic Acids Research* 21(20):4848-4849 (1993).

Hsuih et al., "Novel, Ligation-Dependent PCR Assay for Detection of Hepatitus C Virus in Serum," *J. Clin. Microbiol.* 34(3):a-g (1996).

Park et al., "Detection of Hepatitis C Virus RNA Using Ligation-Dependent Polymerase Chain Reaction in Formalin-Fixed, Paraffin-Embedded Liver Tissue," 149(5):1485-1491 (1996).

Wegmüller et al., "Combination of Oligonucleotide Ligation and PCR to Detect Point Mutations," (unpublished).

Nilsson et al., "Padlock Probes: Circularizing Oligonucleotides for Localized DNA Detection," *Science* 265:2085-2088 (1994).

Newton et al., "The Production of PCR Products With 5' Single-Stranded Tails Using Primers That Incorporate Novel Phosphoram Phosphoramidite Intermediates," *Nucleic Acids Research* 21(5):1155-1162 (1993).

Jin et al., "Alternating Current Impedance Characterization of the Structure of Alkylsiloxane Self-Assembled Monolayers on Silicon," *Langmuir* 10:2662-2671 (1994).

Cheng et al., "In Situ Attenuated Total Reflectance Fourier Transform Infrared Spectroscopy of Carboxylate-Bearing, Siloxane-Anchored, Self-Assembled Monolayers: A Study of Carboxylate Reactivity and Acid-Base Properties," *Langmuir* 11:1190-1195 (1995).

Kim et al., "Polymeric Self-Assembled Monolayers. 2. Synthesis and Characterization of Self-Assembled Polydiacetylene Mono- and Multilayers," *J. Am. Chem. Soc.* 117:3963-3967 (1995).

Lauer et al., "Cloning, Nucleotide Sequence, and Engineered Expression of *Thermus thermophilus* DNA Ligase, a Homolog of *Escherichia coli* DNA Ligase," *J. Bacteriol.* 173(16):5047-5053 (1991).

Barany et al., "Cloning, Overexpression and Nucleotide Sequence of a Thermostable DNA Ligase-Encoding Gene," *Gene* 109:1-11 (1991).

Jou et al., "Deletion Detection in the Dystrophin Gene by Multiplex Gap Ligase Chain Reaction and Immunochromatographic Strip Technology," *Human Mutation* 5:86-93 (1995).

Chan et al., "Polymeric Self-Assembled Monolayers. 3. Pattern Transfer by Use of Photolithography, Electrochemical Methods and an Ultrathin, Self-Assembled Diacetylenic Resist," *J. Am. Chem. Soc.* 117:5875-5876 (1995).

Munkholm et al., "Polymer Modification of Fiber Optic Chemical Sensors as a Method of Enhancing Fluorescence Signal for pH Measurement," *Anal. Chem.* 58:1427-1430 (1986).

Graham et al., "Gene Probe Assays on a Fibre-Optic Evanescent Wave Biosensor," *Biosensors & Bioelectronics* 7:487-493 (1992).

Chetverin et al., "Sequencing of Pools of Nucleic Acids on Oligonucleotide Arrays," *BioSystems* 30:215-231 (1993).

Pease et al., "Light-Generated Oligonucleotide Arrays for Rapid DNA Sequence Analysis," *Proc. Natl. Acad. Sci. USA* 91:5022-5026 (1994).

Beattie et al., "Advances in Genosensor Research," *Clin. Chem.* 41(5):700-706 (1995).

Bains, "Mixed Hybridization and Conventional Strategies for DNA Sequencing," *Gata* 10(3-4):84-94 (1993).

Kuznetsova et al., "DNA Sequencing by Hybridization with Oligonucleotides Immobilized in a Gel," *Mol. Biol. (Mosk) (Russia),* 28(2):290-299 (English abstract), no date available.

Lysov et al., "Measurement of Distances Between DNA Segments Increases the Efficiency of Sequencing by Hybridization with Oligonucleotide Matrix," *Molecular Biology* 28(3)(Part 2):433-436 (1994).

Livshits et al., "Dissociation of Duplexes Formed by Hybridization of DNA with Gel-Immobilized Oligonucleotides," *Journal of Biomolecular Structure & Dynamics* 11(4):783-795 (1994).

Davis et al., "Quantitative Detection of Hepatitis C Virus RNA With a Solid-phase Signal Amplification Method: Definition of Optimal Conditions for Specimen Collection and Clinical Application in Interferon-treated Patients," *Hepatology* 19(6):1337-1341 (1994).

Urdea, "Synthesis and Characterization of Branched DNA (bDNA) for the Direct and Quantitative Detection of CMV, HBV, HCV, and HIV," *Clincal Chemistry* 39(4):725-726 (1993).

Reynolds et al., "Analysis of Genetic Markers in Forensic DNA Samples Using the Polymerase Chain Reaction," *Anal. Chem.* 63:2-15 (1991).

Buyse et al., "Rapid DNA Typing of Class II HLA Antigens Using the Polymerase Chain Reaction and Reverse Dot Blot Hybridization," *Tissue Antigens* 41:1-14 (1993).

Gyllensten et al., "PCR-Based HLA Class II Typing," *PCR Meth. Appl.* 1:91-98 (1991).

Chamberlain et al., "Deletion Screening of the Duchenne Muscular Dystrophy Locus Via Multiplex DNA Amplification," *Nucleic Acids Res.* 16(23):11141-11156 (1988).

Tsui, "Mutations and Sequence Variations Detected in the Cystic Fibrosis Transmembrane Conductance Regulator (CFTR) Gene: A Report From the Cystic Fibrosis Genetic Analysis Consortium," *Human Mutat.* 1:197-203 (1992).

Hollstein et al., "p53 Mutations in Human Cancers," *Science* 253:49-53 (1991).

Gibbs et al., "Detection of Single DNA Base Differences by Competitive Oligonucleotide Priming," *Nucleic Acids Res.* 17:2437-2448 (1989).

Chehab et al., "Detection of Specific DNA Sequences by Fluorescence Amplification: A Color Complementation Assay," *Proc. Natl. Acad. Sci. USA* 86:9178-9182 (1989).

Livak et al., "Detection of Single Base Differences Using Biotinylated Nucleotides With Very Long Linker Arms," *Nucleic Acids Res.* 20(18):4831-4837 (1992).

Nickerson et al., "Automated DNA Diagnostics Usi ng an ELISA-Based Oligonucleotide Ligation Assay," *Proc. Natl. Acad. Sci. USA* 87:8923-8927 (1990).

Weber et al., "Abundant Class of Human DNA Polymorphisms Which Can Be Typed Using the Polymerase Chain Reaction," *Am. J. Hum. Genet.* 44:388-396 (1989).

Weissenbach et al., "A Second-Generation Linkage Map of the Human Genome," *Nature (London)* 359:794-801 (1992).

Ruppert et al., "Evidence for Two Bladder Cancer Suppressor Loci on Human Chromosome $9^1$," *Cancer Res.* 53:5093-5095 (1993).

van der Riet et al., "Frequent Loss of Chromosome 9p21-22 Early in Head and Neck Cancer Progression," *Cancer Res.* 54:1156-1158 (1994).

Nawroz et al., "Allelotype of Head and Neck Squamous Cell Carcinoma," *Cancer Res.* 54:1152-1155 (1994).

Cairns et al., "Homozygous Deletions of 9p21 in Primary Human Bladder Tumors Detected by Comparative Multiple Polymerase Chain Reaction," *Cancer Res.* 54:1422-1424 (1994)

The Huntington's Disease Collaborative Research Group, "A Novel Gene Containing a Trinucleotide Repeat That is Expanded and Unstable on Huntington's Disease Chromosomes," *Cell* 72:971-983 (1993).

Kremer et al., Mapping of DNA Instability at the Fragile X to a Trinucleotide Repeat Sequence p(CCG)n *Science* 252:1711-1714 (1991).

Imbert et al., "Origin of the Expansion Mutation in Myotonic Dystrophy," *Nat. Genet.* 4:72-76 (1993).

Orr et al., "Expansion of an Unstable Trinucleotide CAG Repeat in Spinocerebellar Ataxia Type 1," *Nat. Genet.* 4:221-226 (1993).

Biancalana et al., "Moderate Instability of the Trinucleotide Repeat in Spino Bulbar Muscular Atrophy," *Hum. Mol. Genet.* 1(4):255-58 (1992).

Chung et al., "Evidence for a Mechanism Predisposing to Intergenerational CAG Repeat Instability in Spinocerebeller Ataxia Type I," *Nat. Genet.* 5:254-258 (1993).

Koide et al., "Unstable Expansion of CAG Repeat in Hereditary Dentatorubral-Pallidoluysian Atrophy (DRPLA)," *Nat. Genet.* 6:9-13 (1994).

Peinado et al., "Isolation and Characterization of Allelic Losses and Gains in Colorectal Tumors by Arbitrarily Primed Polymerase Chain Reaction," *Proc. Natl. Acad. Sci. USA* 89:10065-10069 (1992).

Ionov et al., "Ubiquitous Somatic Mutations in Simple Repeated Sequences Reveal a New Mechanism for Colonic Carcinogenesis," *Nature (London)* 363:558-561 (1993).

Thibodeau et al., "Microsatellite Instability in Cancer of the Proximal Colon," *Science* 260:816-819 (1993).

Risinger et al., "Genetic Instability of Microsatellites in Endometrial Carcinoma," *Cancer Res.* 53:5100-5103 (1993).

Han et al., "Genetic Instability in Pancreatic Cancer and Poorly Differentiated Type of Gastric Cancer," *Cancer Res.* 53:5087-5089 (1993).

Peltomäki et al., "Microsatellite Instability is Associated with Tumors That Characterize the Hereditary Non-Polyposis Colorectal Carcinoma Syndrome," *Cancer Res.* 53:5853-5855 (1993).

Gonzalez-Zulueta et al., Microsatellite Instability in Bladder Cancer, *Cancer Res.* 53:5620-5623 (1993).

Merlo et al., "Frequent Microsatellite Instability in Primary Small Cell Lung Cancer," *Cancer Res.* 54:2098-2101 (1994).

Leach et al., "Mutations of a mutS Homolog in Hereditary Nonpolyposis Colorectal Cancer," *Cell* 75:1215-1225 (1993).

Fishel et al., "The Human Mutator Gene Homolog MSH2 and its Association with Hereditary Nonpolyposis Colon Cancer," *Cell* 75:1027-1038 (1993).

Papadopoulos et al., "Mutation of a mutl. Homolog in Hereditary Colon Cancer," *Science* 263:1625-1629 (1994).

Bronner et al., "Mutation in the DNA Mismatch Repair Gene Homologue hMLH1 is Associated with Hereditary Non-Polyposis Colon Cancer," *Nature (London)* 368:258-261 (1994).

Southern et al., "Analyzing and Comparing Nucleic Acid Sequences by Hybridization to Arrays of Oligonucleotides: Evaluation using Experimental Models," *Genomics* 13:1008-1017 (1992).

Fodor et al., "Multiplexed Biochemical Assays with Biological Chips," *Nature* 364:555-556 (1993).

Khrapko et al., "A Method for DNA Sequencing by Hybridization with Oligonucleotide Matrix," *J. DNA Seq. Map.* 1:375-388 (1991).

Van Ness et al., "A Versatile Solid Support System for Oligodeoxynucleotide Probe-based Hybridization Assays," *Nucleic Acids Res.* 19:3345-3350 (1991).

Zhang et al., "Single-base Mutational Analysis of Cancer and Genetic Diseases Using Membrane Bound Modified Oligonucleotides," *Nucleic Acids Res.* 19:3929-3933 (1991).

Lipshutz et al., "Using Oligonucleotide Probe Arrays To Assess Genetic Diversity," *Biotechniques* 19:442-447 (1995).

Maskos et al., "A Study of Oligonucleotide Reassociation Using Large Arrays of Oligonucleotides Synthesised on a Glass Support," *Nucleic Acids Res.* 21:4663-4669 (1993).

Maskos et al., "A Novel Method for the Analysis of Multiple Sequence Variants by Hybridisation to Oligonucleotides," *Nucleic Acids Res.* 21:2267-2268 (1993).

Timofeev et al., "Regioselective Immobilization of Short Oligonucleotides to Acrylic Copolymer Gels," *Nucleic Acids Res.* 24(16):3142-3148 (1996).

Guo et al., Direct Fluorescence Analysis of Genetic Polymorphisms by Hybridization with Oligonucleotide Arrays on Glass Supports, *Nucleic Acids Res.* 22:5456-5465 (1994).

Hacia et al., "Detection of Heterozygous Mutations in BRCA1 Using High Density Oligonucleotide Arrays and Two-Colour Fluorescence Analysis," *Nat. Genet.* 14:441-447 (1996).

Chee et al., "Accessing Genetic Information with High-Density DNA Arrays," *Science* 274:610-614 (1996).
Schena et al., "Parallel Human Genome Analysis: Microarray-Based Expression Monitoring of 1000 Genes," *Proc. Natl. Acad. Sci. USA* 93:10614-10619 (1996).
Shalon et al., "A DNA Microarray System for Analyzing Complex DNA Samples Using Two-Color Fluorescent Probe Hybridization," *Genome Res.* 6:639-645 (1996).
Cronin et al., "Cystic Fibrosis Mutation Detection by Hybridization to Light-Generated DNA Probe Arrays," *Human Mutation* 7:244-255 (1996).
Wang et al., "Large-Scale Identification, Mapping, and Genotyping of Single-Nucleotide Polymorphisms in the Human Genome," *Science* 280:1077-1082 (1998).
Southern, "DNA Chips: Analyzing Sequence by Hybridization to Oligonucleotides on a Large Scale," *Trends in Genet.* 12(3):110-115 (1996).
Drobyshev et al., "Sequence Analysis by Hybridization with Oligonucleotide Microchip: Identification of β-Thalassemia Mutations," *Gene* 188:45-52 (1997).
Yershov et al., "DNA Analysis and Diagnostics on Oligonucleotide Microchips," *Proc. Natl. Acad. Sci. USA* 93:4913-4918 (1996).
Parinov et al., "DNA Sequencing by Hybridization to Microchip Octa- and Decanucleotides Extended by Stacked Pentanucleotides," *Nucleic Acids Res.* 24(15):2998-3004 (1996).
Kozal et al., "Extensive Polymorphisms Observed in HIV-1 Clade B Protease Gene Using High-Density Oligonucleotide Arrays," *Nature Medicine* 2:753-759 (1996).
Telenti et al., "Competitive Polymerase Chain Reaction Using an Internal Standard: Application to the Quantitation of Viral DNA," *Journal of Virological Methods* 39:259-268 (1992).
Nikiforov et al., "Genetic Bit Analysis: A Solid Phase Method for Typing Single Nucleotide Polymorphisms," *Nucleic Acids Res.* 22(20):4167-4175 (1994).
Janssen et al., "Evaluation of the DNA Fingerprinting Method AFLP as a New Tool in Bacterial Taxonomy," *Microbiology* 142:1881-1893 (1996).
Belgrader et al., "A Multiplex PCR-Ligase Detection Reaction Assay for Human Identity Testing," *Genome Science & Tech.* 1:77-87 (1996).
Day et al., "Identification of Non-Amplifying CYP21 Genes When Using PCR-Based Diagnosis of 21-Hydroxylase Deficiency in Congenital Adrenal Hyperplasis (CAH) Affected Pedigrees," *Hum. Mol. Genet.* 5(12):2039-2048 (1996).
Heller et al., "Discovery and Analysis of Inflammatory Disease-Related Genes Using cDNA Microarrays," *Proc. Nat'l Acad. Sci. USA* 94:2150-2155 (1997).
Gerry et al., "Universal DNA Microarray Method for Multiplex Detection of Low Abundance Point Mutations," *J. Mol. Biol.* 292:251-262 (1999).
Lysov et al., "DNA Sequencing by Hybridization to Oligonucleotide Matrix. Calculation of Continuous Stacking Hybridization Efficiency," *Journal of Biomolecular Structure & Dynamics* 11(4):797-812 (1994).
Milner et al., "Selecting Effective Antisense Reagents on Combinatorial Oligonucleotide Arrays," *Nature Biotechnology* 15:537-541 (1997).
Takahashi et al., "Thermophilic HB8 DNA Ligase: Effects of Polyethylene Glycols and Polyamines on Blunt-End Ligation of DNA," *J. Biochem.* 100:123-131 (1986).

Takahashi et al., "Purification of HB8 DNA Ligase by Red Sepharose Chromatography," *Agric. Biol. Chem.* 50(5):1333-1334 (1986).
Lawyer et al., "Isolation, Characterization, and Expression in *Escherichia coli* of the DNA Polymerase Gene from *Thermuss aquaticus*," *J. Bio. Chem.* 264(11):6427-6437 (1989).
Taguchi et al., "A Chaperonin from a Thermophilic Bacterium, *Thermus thermophilus*, That Controls Refoldings of Several Thermophilic Enzymes," *J. Biol. Chem.* 266(33):22411-22418 (1991).
Schalling et al., "Direct Detection of Novel Expanded Trinucleotide Repeats in the Human Genome," *Nature Genetics*, 4:135-139 (1993).
Caskey, "Molecular Medicine—A Spin-off From the Helix," *JAMA* 269:1986-1993 (1993).
Perucho et al., "Genetic and Physical Linkage of Exogenous Sequences in Transformed Cells," *Cell* 22(Part I):309-317 (1980).
Weiss, "Hot Prospect for New Gene Amplifier," *Science*, 254:1292-1293 (1991).
Birkenmeyer et al., "Mini-Review—DNA Probe Amplification Methods," *J.Virol Methods* 35:117-126 (1991).
Holding et al., "Diagnosis of Beta-Tiialassaemia by DNA Amplification in Single Blastomeres from Mouse Preimplantation Embryos," *The Lancet* pp. 532-535 (1989).
Barringer et al., "Blunt-End and Single-Strand Ligations by *Escherichia coli* Ligase: Influence on an in vitro Amplification Scheme," *Gene* 89:117-122 (1990).
Matsuzawa et al., "Purification and Characterization of Aqualysin I (a Thermophilic Alkaline Serine Protease) Produced by *Thermus aquaticus* YT-1," *Eur. J. Biochem.* 171:441-447 (1988).
Zimmerman et al., "Macromolecular Crowding Allows Blunt-end Ligation by DNA Ligase from Rat Liver of *Escherichia coli*," 80:5852-5856 (1983).
Barany, "A Genetic System for Isolation and Characterization of TaqI Restriction Endonuclease Mutants," *Gene* 56:13-27 (1987).
Cotton, "Detection of Single Base Changes in Nucleic Acids," *Biochem J.* 263:1-10 (1989).
Konrad et al., "Genetic and Enzymic Characterization of a Conditional Lethal Mutant of *Escherichia coli* K12 with a Temperature-Sensitive DNA Ligase," *Chem Abstracts* 79(13):75781v, pp. 243-244 (1973).
Hanahan, "Studies on Transformation of *Escherichia coli* with Plasmids," *J. Molec. Biol.*. 166:557-580 (1983).
Wu et al., "Specificity of the Nick-Closing Activity of Bacteriophage T4 DNA Ligase," *Gene* 76:245-54 (1989).
Xu et al., "Microsequence Analysis of Peptides and Proteins. VIII. Improved Electroblotting of Proteins onto Membranes and Derivatized Glass-Fiber Sheets," *Analytical Biochem.* 170:19-30 (1988).
Moos et al., "Reproducible High Yield Sequencing of Proteins Electrophoretically Separated and Transferred to an Inert Support," *J. Biol. Chem.* 263(13):6005-6008 (1988).
Matsuda et al., "The Primary Structure of L-1 Light Chain of Chicken Fast Skeletal Muscle Myosin and Its Genetic Implication," *FEBS Letters* 126(1):111-113 (1981).
Lathe, "Synthetic Oligonucleotide Probes Deduced from Amino Acid Sequence Data Theoretical and Practical Considerations," *J. Molec. Biol.* 183:1-12 (1985).
Zebala et al., "Characterization of Steady State, Single-Turnover, and Binding Kinetics of the TaqI Restriction Endonuclease," *The Journal of Biology and Chemistry* 267(12):8097-8105 (1992).

Davis et al., "Protein Splicing in the Maturation of *M. tuberculosis* RecA Protein: A Mechanism for Tolerating a Novel Class of Intervening Sequence," *Cell* 71(1):201-210 (1992).

Perler et al., "Intervening Sequences in an Archaea DNA Polymerase Gene," *Proc. Natl. Acad. Sci. USA* 89:5577-5581 (1992).

Shively, "Reverse-Phase HPLC Isolation and Microsequencing," in *Methods of Protein Characterization. A Practical Handbook*, Clifton, New Jersey: Humuna Press, pp. 46-49 (1986).

Niece et al., "A Synthetic Peptide for Evaluating Protein Sequencer and Amino Analyzer Performance in Core Facilities: Design and Results," in Hugli, ed., *Techniques in Protein Chemistry*, Academic Press, Inc., pp. 89-101 (date unknown).

Walsh et al., "Advances in Protein Sequencing," *Annual Review of Biochemistry* 50:261-284 (1981).

Roitsch et al., "High-Performance Liquid Chromatography of Biologically Active Proteins in the Nanogram (Picomole) Range," in Lefkovits, eds., *Immunological Methods*, vol. III, Academic Press, Inc., pp. 85-86, 106-107, 274-284 (1985).

Wang et al., Molecular Genetic and Genetic Correlations in Sodium Channelopathies: Lack of Founder and Evidence for a Second Gene, *Am. J. Hum. Genet.* 52:1074-1084 (1993).

Feero et al., "Hyperkalemic Periodic Paralysis: Rapid Molecular Diagnosis and Relationship of Genotype to Phenotype in 12 Families," *Neurology* 43(4):668-673 (1993).

Wiedmann et al., "Detection of *Listeria monocytogenes* with a Nonisotopic Polymerase Chain Reaction-Coupled Ligase Chain Reaction Assay," *Applied Environmental Microbiology* 59(8):2743-2745 (1993).

Wiedmann et al., "Discrimination of *Listeria monocytogenes* from Other *Listeria* Species by Ligase Chain Reaction," *Applied and Environmental Microbiology* 58(11):3443-3447 (1992).

Zebala et al., "Implications for the Ligase Chain Reaction in Gastroenterology," *Clin. Gastroenterol.* 17(2):171-175 (1993).

Prchal et al., "Transcriptional Analysis of the Active X-Chromosome in Normal and Clonal Hermatopoiesis," *Blood* 81:269-271 (1993).

Ruiz-Opazo et al., "Confirmation of Mutant $\alpha_1$ Na,K-ATPase Gene and Transcript in Dahl Salt-Sensitive/JR Rats," *Hypertension* 24(3):260-270 (1994).

Landegren, "Molecular Mechanics of Nucleic Acid Sequence Amplification," *Trends in Genetics* 9:199-204 (1993).

Pfeffer et al., "A Ligase Chain Reaction Targeting Two Adjacent Nucleotides Allows the Differentiation of Cowpox Virus from Other *Orthopoxvirus* Species," *Journal of Virological Methods* 49:353-360 (1994).

Kälin et al., "Evaluation of the Ligase Chain Reaction (LCR) for the Detection of Point Mutations," *Mutation Research* 283:119-123 (1992).

Day et al., "Nucleotide Analogs Facilitate Base Conversion with 3' Mismatch Primers," *Nucleic Acids Research* 27(8):1810-1818 (1999).

Marsh et al., "*Pyrococcus furiosus* DNA Ligase and the Ligase Chain Reaction," *Strategies in Molecular Biology* 5:73-76 (Date Unknown).

Nakazawa et al., "UV and Skin Cancer: Specific p53 Gene Mutation in Normal Skin as a Biologically Relevant Exposure Measurement," *Proc. Natl. Acad. Sci. USA* 91:360-364 (1994).

Rogers, "Nucleic Acid Amplification and Infectious Disease," *Human Pathology* 26(6):591-593 (1994).

Wilson et al., "Identification of *Erwinia stewartii* by a Ligase Chain Reaction Assay," *Applied and Environmental Microbiology* 60(1):278-284 (1994).

Bloch, "A Biochemical Perspective of the Polymerase Chain Reaction," *Biochemistry* 30(11):2735-2747 (1991).

Jonsson et al., "Nucleotide Sequence of the DNA Ligase Gene from *Thermus scotoductus* and Conserved Motifs in DNA Ligases" (1994).

Tong et al., "Biochemical Properties of a High Fidelity DNA Ligase from *Thermus* Species AK16D," *Nucleic Acids Research* 27(3):788-794 (1999).

Wallace et al., "Ligase Chain Reaction for the Detection of Specific DNA Sequences and Point Mutations," in *Technologies for Detection of DNA Damage and Mutations*, Pfeifer, G.P., ed., New York: Plenum Press, Chapter 23, pp. 307-322 (1996).

Reyes et al., "Ligase Chain Reaction Assay for Human Mutations: The Sickle Cell by LCR Assay," *Clinical Chemistry* 43(1): 40-44 (1997).

Dille et al., "Amplification of *Chlamydia trachomatis* DNA by Ligase Chain Reaction," *Journal of Clinical Microbiology* 31(3):729-731 (1993).

Birkenmeyer et al., "Preliminary Evaluation of the Ligase Chain Reaction for Specific Detection of *Neisseria gonorrhoeae*," *Journal of Clinical Microbiology* 30(12):3089-3094 (1992).

Bsat et al., "Food Safety Applications of Nucleic Acid-Based Assays," *Food Technology* pp. 142-145 (1994).

Winn-Deen et al., "Non-Radioactive Detection of *Mycobacterium tuberculosis* LCR Products in a Microtitre Plate Format," *Molecular and Cellular Probes* 7:179-186 (1993).

Weisberg et al., "Lyophilization as a Method to Store Samples of Whole Blood," *BioTechniques* 15(1):64-68 (1993).

Birkenmeyer et al., "DNA Probe Amplification Methods," *Journal of Virological Methods* 35:117-126 (1991).

Batt et al., "Detection of Bovine Leukocyte Adhesion Deficiency by Nonisotopic Ligase Chain Reaction," *Animal Genetics* 25:95-98 (1994).

Rolfs et al., "Alternative Methods to PCR," in *PCR: Clinical Diagnostics and Research*, Berlin: Springer-Verlag, Chapter 23, pp. 263-265 (1992).

Hames et al., eds., *Nucleic Acid Hybridisation. A Practical Approach*, Oxford, England: IRL Press, pp. 5-7 (1985).

"Nucleic Acid Hybridization—General Aspects," in *Nonradioactive In Situ Hybridization Application Manual*, Indianapolis, Indiana: Boehringer Mannheim Corporation, Chapter III (1992).

Howard et al., "Cloning the Ddel Restriction-Modification System Using a Two-Step Method," *Nucleic Acids Research* 14(20):7939-7951 (1986).

\* cited by examiner

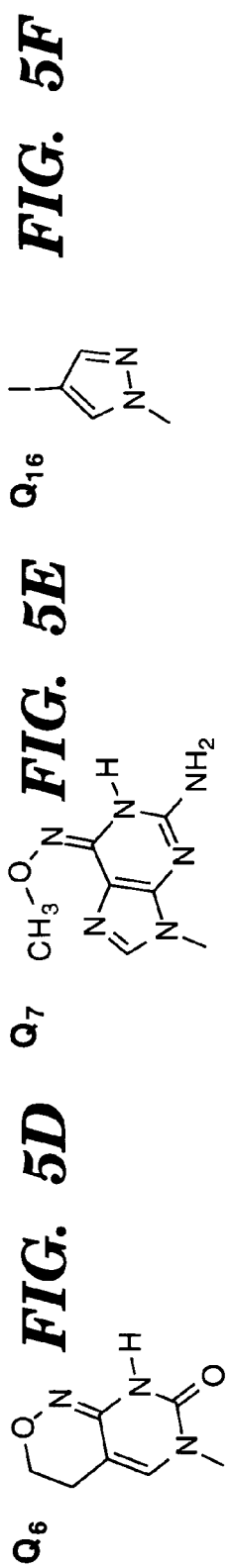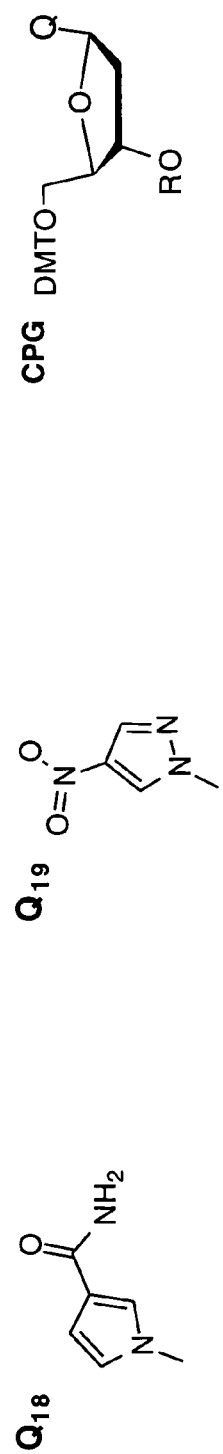
FIG. 5A  FIG. 5B  FIG. 5C  FIG. 5D  FIG. 5E  FIG. 5F  FIG. 5G  FIG. 5H  FIG. 5I

FIG. 6A

PRIMERS

```
Ztop          CTT GGA CGA GTT CAT ACG C p53zip248     CTT GGA CGA GTT CAT ACG C ACG CGT TCC TGC ATG GGC GGC ATG A p53-248X                                T TCT TCC TGC ATG GGC GGC ATG AAX→pol
                                        ||  ||| ||| ||| ||| ||| ||| |||
                                     3' CA AGG AGC TAC CCG TAC CCG TAC TTG GCC TCC GGG TAG GAG TGG TAG TAG TGT 5'  (-)
50 bp synthetic                         ||  ||| ||| ||| ||| ||| ||| ||| ||| ||| ||| ||| ||| ||| ||| ||| |||
duplex DNA                           5' GT TCC TCG ATG GGC ATG GGC ATG AAC CGG AGG CCC ATC CTC ACC ATC ATC ACA 3'  (+)
                                                                              ||| ||| ||| ||| ||| ||| |||
                                                                   pol←X TCC GGG TAG GAG TGG TAG TAG TCT T
p53-248XR
                                                                         ||| ||| ||| ||| ||| ||| ||| |||
p53zip248R                                                             C GGG TAG GAG TGG TAG TAG TGC ACC GCT GGG TCA AAC G Zbot                                                                                                 C ACC GCT GGG TCA AAC G
``` codon248 →

```
PRIMERS

Ztop            CTT GGA CGA GTT CAT ACG C
p53zip248T      CTT GGA CGA GTT CAT CAT ACG CGT TCC TGC ATG GGC GGC ATG AAT
                                                                          codon248→
p53-248Q_N                                  T TCT TCC ATG TGC TGC ATG GGC GGC ATG AAQ_N→pol
                                            = === === === === === === === === === ===
50 bp synthetic 3' CA AGG AGC TAC CCG TTG GCC TCC GGG TAG GAG TGG TAG TGT 5' (-)
duplex DNA      5' GT TCC ATG TGC ATG GGC AAC CGG AGG CCC ATC CTC ACC ATC ACA 3' (+)
                                            = === === === === === === === === === ===
p53-248 Q_N^R                      pol← Q_N TCC GGG TAG GAG TGG TAG TAG TCT T
p53zip248TR                             T TCC GGG TAG GAG TGG TAG TAG TGC ACC GCT GGG TCA AAC G
Zbot                                                                C ACC GCT GGG TCA AAC G
```

FIG. 6B

LDR PRIMERS

```
                                                 DISCRIMINATION                    COMMON
                                                                                                                     5'
P53LDR248FCA     F-AAAAAA GC ATG GGC ATG AAC A
P53LDR248FCG       F-AAAA GC ATG GGC ATG AAC G
P53LDR248FCT         F-AA GC ATG GGC ATG AAC T
P53LDR248FCC           F- GC ATG GGC ATG AAC C ┐...ligase
                                                 └──►
P53LDR248PGG                                        GG AGG CCC ATC CTC ACC ATC AT-block
                          ||  ||| ||| ||| |||    || ||| ||| ||| ||| ||| ||| ||
                 3' (- strand) ...GTA TGC GCA AGG ACG TAC CCG TAC TTG NCC TCC GGG TAG GAG TGG TAG TAG TGA ACC...
CONVERSION
PRODUCTS
```

FIG. 6C

CODON 248 CONVERTED TO A *TaqI* SITE

```
PRIMERS

Ztop              CTT GGA CGA GTT CAT ACG C
P53zip248short    CTT GGA CGA GTT CAT ACG C
P53-248short                          GT TCC ATG GGC GGC ATG A
                                      GT TCC ATG GGC GGC ATG A →pol
                                      ||  |||  |||  |||  |||  |
                                   CA AGG AGC TAC CCG CCG TAC TTG GCC TCC GGG TAG GAG TGG TAG TAG TGT ... 5'  (−)
p53 exon 7                      3'...
PCR product                     5'... GT TCC ATG GGC GGC ATG AAC CGG AGG CCC ATC CTC ACC ATC ATC ACA ... 3'  (+)
(MK not shown)                         ||  |||  |||  |||  |||  |||  |||  |||  |||  |||  |||  |||
                                                                    pol←GG TAG GAG TGG TAG TAG TG
p53-248shortR                                                            GG TAG GAG TGG TAG TAG TG
p53zip248shortR                                                        C GGG TAG GAG TGG TAG TAG TGC ACC GCT GGG TCA AAC G
Zbot                                                                   C     TAG GAG TGG TAG TAG TGC ACC GCT GGG TCA AAC G
```

MspI (CCGG)
                                                            codon 248
                                                                ↓

*FIG. 11A*

PRIMERS

```
                                                              MspI (CCGG)
                                                              codon 248
                                                                    →
Ztop         CTT GGA CGA GTT CAT CAT ACG C
P53zip248T   CTT GGA CGA GTT CAT CAT ACG CGT TCC TGC ATG GGC ATG AAT
P53Taq248T                                   GT  TCC TGC ATG GGC ATG AAT
P53Taq248Q6                                  GT  TCC TGC ATG GGC ATG AAQ₆ → pol
                                         TTCT     ||| ||| ||| ||| ||| |||
50 bp synthetic                       3' CA  AGG ACG TAC CCG TAC TTG GCC TCC GGG TAG GAG TGG TAG TAG TGT 5' (-)
duplex DNA, or                                                                                          
PCR product                           5' GT  TCC TGC ATG GGC ATG AAC CGG AGG ATC CTC ACC ATC ATC ACA 3' (+)
                                                                  ::
P53Taq248Q6R                                                 pol ← Q₆ TCC GGG TAG GAG TGG TAG TAG TCTT
p53Taq248TR                                                    T   TCC GGG TAG GAG TGG TAG TAG TG
p53zip248TR                                                    T   TCC GGG TAG GAG TGG TAG TAG TGC ACC GCT GGG TCA AAC G
Zbot                                                                                       C ACC GCT GGG TCA AAC G
```

FIG. 11B

LDR PRIMERS

| | DISCRIMINATION | COMMON |
|---|---|---|
| P53LDR248FTCL | F-AAAAAAAA GC ATG GGC ATG AAT C | |
| P53LDR248FCA | F-AAAAAA GC ATG GGC ATG AAC A | |
| P53LDR248FCG | F-AAAA GC ATG GGC ATG AAC G | |
| P53LDR248FCT | F-AA GC ATG GGC ATG AAC T | |
| P53LDR248FCC | F- GC ATG GGC ATG AAC C ...ligase | |
| P53LDR248PGG | | GG AGG CCC ATC CTC ACC ATC AT - block |

```
                                ||| ||| ||| ||| ||| ||| ||| |||       5'
                                                             ligase
                                GG AGG CCC ATC CTC ACC ATC AT - block
                   ||  ||| ||| ||| ||| ||| ||| ||| ||| ||| ||| ||| |||
3'  (- strand)
...GTA TGC GCA AGG ACG TAC CCG TAC TTG NGG TCC GGG TAG GAG TGG TAG TAG TGA ACC....
```

CONVERSION PRODUCTS

*FIG. 11C*

SEQUENCE LISTING

<160> NUMBER OF SEQ ID NOS: 36

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
tgtgatgatg gtgaggatgg gcctccggtt catgccgccc atcgaggaac                50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic

```
                              Oligonucleotide

<400> SEQUENCE: 2
gttcctgcat gggcggcatg aaccggaggc ccatcctcac catcatcaca            50

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: N_region
<222> LOCATION: (25)
<223> OTHER INFORMATION: Where N is A,C,T,G or Q(n) analog

<400> SEQUENCE: 3
ttcttcctgc atgggcggca tgaan                                       25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: N_region
<222> LOCATION: (26)
<223> OTHER INFORMATION: Where N is A,C,T,G or Q(n) analog

<400> SEQUENCE: 4
ttctgatgat ggtgaggatg ggcctn                                      26

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
cttggacgag ttcatacgcg ttcctgcatg ggcggcatga                       40

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
gcaaactggg tcgccacgtg atgatggtga ggatgggc                         38

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
cttggacgag ttcatacgc                                              19
```

```
<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
gcaaactggg tcgccac                                                    17

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
cttggacgag ttcatacgcg ttcctgcatg ggcggcatga at                        42

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
gcaaactggg tcgccacgtg atgatggtga ggatgggcct t                         41

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
aaaaaagcat gggcggcatg aaca                                            24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
aaaagcatgg gcggcatgaa cg                                              22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 13
aagcatgggc ggcatgaact                                                 20
```

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14
gcatgggcgg catgaacc                                                 18

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 15
ggaggcccat cctcaccatc at                                            22

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: N_region
<222> LOCATION: (30)
<223> OTHER INFORMATION: Where N is A,C,T,G

<400> SEQUENCE: 16
ccaagtgatg atggtgagga tgggcctccn gttcatgccg cccatgcagg aacgcgtatg   60

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 17
gttcctgcat gggcggcatg aactggaggc ccatcctcac catcatcaca             50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 18
gttcctgcat gggcggcatg aacgggaggc ccatcctcac catcatcaca             50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 19

-continued gttcctgcat gggcggcatg aacaggaggc ccatcctcac catcatcaca        50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
gttcctgcat gggcggcatg aatcgaaggc ccatcctcac catcatcaca        50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21
gttcctgcat gggcggcatg aagcgcaggc ccatcctcac catcatcaca        50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22
gttcctgcat gggcggcatg aaacgtaggc ccatcctcac catcatcaca        50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 23
gttcctgcat gggcggcatg aacatgaggc ccatcctcac catcatcaca        50

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 24
gttcctgcat gggcggcatg aacgcgaggc ccatcctcac catcatcaca        50

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 25
cttggacgag ttcatacgcg ttcctgcatg ggcggcatga ac        42

```
<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 26
cttggacgag ttcatacgcg ttcctgcatg ggcggcatga ag                         42

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 27
cttggacgag ttcatacgcg ttcctgcatg ggcggcatga aa                         42

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 28
gttcctgcat gggcggca                                                    18

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 29
gtgatgatgg tgaggatgg                                                   19

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 30
gttcctgcat gggcggcatg aat                                              23

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 31
gtgatgatgg tgaggatggg cctt                                             24
```

```
<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: N_region
<222> LOCATION: (25)
<223> OTHER INFORMATION: Where N is Q(6) analog

<400> SEQUENCE: 32
ttcttcctgc atgggcggca tgaan                                            25

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 33
aaaaaaaagc atgggcggca tgaatc                                           26

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: N_region
<222> LOCATION: (30)
<223> OTHER INFORMATION: Where N is A,C,T,G

<400> SEQUENCE: 34
ccaagtgatg atggtgagga tgggcctggn gttcatgccg cccatgcagg aacgcgtatg      60

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 35
gcctcatctt gggcctgtgt tatc                                             24

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 36
gtggatgggt agtagtatgg aagaaatc                                         28
```

COUPLED POLYMERASE CHAIN REACTION-RESTRICTION-ENDONUCLEASE DIGESTION-LIGASE DETECTION REACTION PROCESS

This application claims the benefit of U.S. Provisional Patent Application Ser. No. 60/125,251 filed Mar. 19, 1999.

This invention was developed with government funding under National Institutes of Health Grant Nos. GM-41337-06, GM-43552-05, GM-42722-07, and GM-51628-02. The U.S. Government may have certain rights.

FIELD OF THE INVENTION

The present invention is directed to a process involving coupled polymerase chain reaction ("PCR"), restriction endonuclease digestion ("RE"), and ligase detection reaction ("LDR").

BACKGROUND OF THE INVENTION

Cancer Detection

As the second leading cause of death in this country, almost 600,000 people will die from cancer per year making cancer one of the most alarming of all medical diagnosis. Lifetime risks for developing invasive cancers in men and women are 50 percent and 33 percent, respectively. Expectations are that more than 1.2 million new cases of cancer will be diagnosed in the United States in 1995. Healthcare expenses for cancer in 1994 were approximately $104 billion. However, the full impact of cancer on families and society is not measured only by the amount of money spent on its diagnosis and treatment. A significant number of people are stricken with cancer in their most productive years. Cancers accounted for 18 percent of premature deaths in 1985 and in 1991 more than 9,200 women in the U.S. died from breast cancer before the age of 55.

Currently, diagnosis of cancer is based on histological evaluation of tumor tissue by a pathologist. After a cancer is diagnosed, treatment is determined primarily by the extent or stage of the tumor. Tumor stage is defined by clinical, radiological, and laboratory methods. Standardized classification systems for the staging of tumors have been developed to clearly convey clinical information about cancer patients. Staging provides important prognostic information and forms the basis of clinical studies which allow the testing of new treatment strategies. A staging system was developed (TNM staging system), which classifies tumors according to the size of the primary tumor, the number of regional lymph nodes in which cancer is found, and the presence or absence of metastases to other parts of the body. Smaller cancers with no affected lymph nodes and no distant metastases are considered early stage cancers, which are often amenable to cure through surgical resection. A common measure of prognosis is the 5-year survival rate, the proportion of patients alive five years after the diagnosis of a cancer at a given stage. While 5-year survival rates for many cancers have improved over the last few decades, the fact that some early stage cancers recur within five years or later has led researchers to explore other additional prognostic markers including histological grade, cytometry results, hormone receptor status, and many other tumor markers. Most recently, investigators have explored the use of molecular alterations in cancers as prognostic indicators.

Genetic alterations found in cancers, such as point mutations and small deletions can act as markers of malignant cells.

Detection of Minority Nucleic Acid Sequences

A number of procedures have been disclosed to detect cancer using PCR. Sidransky, et al., "Identification of ras Oncogene Mutations in the Stool of Patients with Curable Colorectal Tumors," Science 256: 102–05 (1992) detects colon cancer by identification of K-ras mutations. This involves a PCR amplification of total DNA, cloning into a phage vector, plating out the phage, repeated probing with individual oligonucleotides specific to several different K-ras mutations, and counting the percentage of positive plaques on a given plate. This is a technically difficult procedure which takes three days to complete, whereby the ratio of mutant to wild-type DNA in the stool sample is determined. Brennan, et al., "Molecular Assessment of Histopathological Staging in Squamous-Cell Carcinoma of the Head and Neck," N. Engl. J. Med. 332(7): 429–35 (1995), finds p53 mutations by sequencing. This specific mutation is then probed for in margin tissue using PCR amplification of total DNA, cloning into a phage vector, plating out the phage, probing with an individual oligonucleotide specific to the mutation found by sequencing, and counting the percentage of positive plaques on a given plate. Berthelemy, et al., "Brief Communications—Identification of K-ras Mutations in Pancreatic Juice in the Early Diagnosis of Pancreatic Cancer," Ann. Int. Med. 123(3): 188–91 (1995) uses a PCR/restriction enzyme process to detect K-ras mutations in pancreatic secretions. This technique is deficient, however, in that mutations are not quantified. Similarly, Tada, et al., "Detection of ras Gene Mutations in Pancreatic Juice and Peripheral Blood of Patients with Pancreatic Adenocarcinoma," Cancer Res. 53: 2472–74 (1993) and Tada, et al., "Clinical Application of ras Gene Mutation for Diagnosis of Pancreatic Adenocarcinoma," Gastroent. 100: 233–38 (1991) subject such samples to allele-specific PCR to detect pancreatic cancer. This has the disadvantages of providing false positives due to polymerase extension off normal template, requiring electrophoretic separation of products to distinguish from primer dimers, being unable to multiplex closely-clustered sites due to interference of overlapping primers, being unable to detect single base or small insertions and deletions in small repeat sequences, and not being practically suitable for quantification of mutant DNA in a high background of normal DNA. Hayashi, et al., "Genetic Detection Identifies Occult Lymph Node Metastases Undetectable by the Histopathological Method," Cancer Res. 54: 3853–56 (1994) uses an allele-specific PCR technique to find K-ras or p53 mutations to identify occult lymph node metastases in colon cancers. A sensitivity of one tumor cell in one thousand of normal cells is claimed; however, obtaining quantitative values requires laborious cloning, plating, and probing procedures. In Mitsudomi, et al., "Mutations of ras Genes Distinguish a Subset of Non-small-cell Lung Cancer Cell Lines from Small-cell Lung Cancer Cell Lines," Oncogene 6: 1353–62 (1991), human lung cancer cell lines are screened for point mutations of the K-, H-, and N-ras genes using restriction fragment length polymorphisms created through mismatched primers during PCR amplification of genomic DNA. The disadvantages of such primer-mediated RFLP include the requirement of electrophoretic separation to distinguish mutant from normal DNA, limited applicability to sites that may be converted into a restriction site, the requirement for additional analysis to determine the nature of the mutation, and the difficulty in quantifying mutant DNA in a high background of normal DNA. Further, these procedures tend to be laborious and inaccurate.

Coupled PCR/ligation processes have been used for detection of minority nucleotide sequences in the presence of majority nucleotide sequences. A PCR/LDR process is used in Frenkel, "Specific, Sensitive, and Rapid Assay for Human Immunodeficiency Virus Type 1 pol Mutations Associated with Resistance to Zidovudine and Didanosine," *J. Clin. Microbiol.* 33(2): 342–47 (1995) to detect HIV mutants. This assay, however, cannot be used for multiplex detection. See also Abravaya, et al., "Detection of Point Mutations With a Modified Ligase Chain (Gap-LCR)," *Nucl. Acids Res.* 23(4): 675–82 (1995) and Balles, et al., "Facilitated Isolation of Rare Recombinants by Ligase Chain Reaction: Selection for Intragenic Crossover Events in the *Drosophila optomotor-blind* Gene," *Molec. Gen. Genet.* 245: 734–40 (1994).

Colorectal lesions have been detected by a process involving PCR amplification followed by an oligonucleotide ligation assay. See Jen, et al., "Molecular Determinants of Dysplasia in Colorectal Lesions," *Cancer Res.* 54: 5523–26 (1994) and Redston, et al., "Common Occurrence of APC and K-ras Gene Mutations in the Spectrum of Colitis-Associated Neoplasias," *Gastroenter.* 108: 383–92 (1995). This process was developed as an advance over Powell, et al., "Molecular Diagnosis of Familial Adenomatous Polyposis," N. *Engl. J. Med.* 329(27): 1982–87 (1993). These techniques tend to be limited and difficult to carry out.

Other procedures have been developed to detect minority nucleotide sequences. Lu, et al., "Quantitative Aspects of the Mutant Analysis by PCR and Restriction Enzyme Cleavage (MAPREC)" *PCR Methods and Appl.* 3: 176–80 (1993) detects virus revertants by PCR and restriction enzyme cleavage. The disadvantages of MAPREC include the requirement for electrophoretic separation to distinguish mutant from normal DNA, limited applicability to sites that may be converted into a restriction site, the requirement for additional analysis to determine the nature of the mutation, and difficulty in quantifying mutant DNA in a high background of normal DNA. In Kuppuswamy, et al., "Single Nucleotide Primer Extension to Detect Genetic Diseases: Experimental Application to Hemophilia G (Factor IX) and Cystic Fibrosis Genes," *Proc. Natl. Acad. Sci. USA* 88: 1143–47 (1991), a PCR process is carried out using two reaction mixtures for each fragment to be amplified with one mixture containing a primer and a labeled nucleotide corresponding to the normal coding sequence, while the other mixture contains a primer and a labeled nucleotide corresponding to the mutant sequence. The disadvantages of such mini sequencing (i.e. SNuPe) are that the mutations must be known, it is not possible to multiplex closely clustered sites due to interference of overlapping primers, it is not possible to detect single base or small insertions and deletions in small repeat sequences, and four separate reactions are required. A mutagenically separated PCR process is disclosed in Rust, et al., "Mutagenically Separated PCR (MS-PCR): a Highly Specific One Step Procedure for easy Mutation Detection" *Nucl. Acids Res.* 21(16): 3623–29 (1993) to distinguish normal and mutant alleles, using different length allele-specific primers. The disadvantages of MS-PCR include possibly providing false positives due to polymerase extension off normal template, requiring electrophoretic separation of products to distinguish from primer dimers, the inability to multiplex closely-clustered sites due to interference of overlapping primers, the inability to detect single base or small insertions and deletions in small repeat sequences, and not being ideally suited for quantification of mutant DNA in high background of normal DNA. In Suzuki, et al., "Detection of ras Gene Mutations in Human Lung Cancers by Single-Strand Conformation Polymorphism Analysis of Polymerase Chain Reaction Products," *Onco-gene* 5: 1037–43 (1990), mutations are detected in a process having a PCR phase followed by a phase involving single strand conformation polymorphism ("SSCP") of the amplified DNA fragments. The disadvantages of SSCP include the requirement for electrophoretic separation to distinguish mutant conformer from normal conformer, the failure to detect 30% of possible mutations, the requirement for additional analysis to determine the nature of the mutation, and the inability to distinguish mutant from silent polymorphisms.

Nucleotide Conversion Fidelity

Many of the approaches to detecting the presence of a given sequence or sequences in a polynucleotide sample involve amplification of the minority sequence(s) by polymerase chain reaction (PCR). U.S. Pat. No. 4,683,202 to Mullis, et al., and R. K. Saiki, et al., *Science* 230:1350 (1985). In this method, primers complementary to opposite end portions of the selected sequence(s) are used to promote, in conjunction with thermal cycling, successive rounds of primer-initiated replication. The amplified sequence(s) may be readily identified by a variety of techniques. This approach is particularly useful for detecting the presence of low-copy sequences in a polynucleotide-containing sample, e.g., for detecting pathogen sequences in a body-fluid sample. However, a nonselective PCR strategy will amplify both mutant and wild-type alleles with approximately equal efficiency, resulting in low abundance mutant alleles comprising only a small fraction of the final product. If the mutant sequence comprises less than 25% of the amplified product, it is unlikely that DNA sequencing will be able to detect the presence of such an allele. Although it is possible to accurately quantify low abundance mutations by first separating the PCR products by cloning and subsequently probing the clones with allele-specific oligonucleotides (ASOs) (Saiki et al., "Analysis of Enzymatically Amplified Beta-Globin and HLA-DQ Alpha DNA with Allele-Specific Oligonucleotide Probes," *Nature,* 324(6093):163–6 (1986); Sidransky et al., "Identification of Ras Oncogene Mutations in the Stool of Patients with Curable Colorectal Tumors," *Science,* 256:102–5 (1992); and Brennan et al., "Molecular Assessment of Histopathological Staging in Squamous-Cell Carcinoma of the Head And Neck," *N. Engl. J. Med.,* 332(7):429–35 (1995)), this approach is time consuming. In contrast, allele-specific PCR methods can rapidly and preferentially amplify mutant alleles. For example, multiple mismatch primers have been used to detect H-ras mutations at a sensitivity of 1 mutant in $10^5$ wild-type alleles (Cha et al., "Mismatch Amplification Mutation Assay (MAMA): Application to the C-H-Ras Gene," *PCR Methods Appl.,* 2(1):14–20 (1992)) and claims as high as 1 mutant in $10^6$ wild-type alleles have been reported (Haliassos et al., "Detection of Minority Point Mutations by Modified PCR Technique: A New Approach for a Sensitive Diagnosis of Tumor-Progression Markers," *Nucleic Acids Res.,* 17:8093–9 (1989); and Chen et al., "A Nonradioactive, Allele-Specific Polymerase Chain Reaction for Reproducible Detection of Rare Mutations in Large Amounts of Genomic DNA: Application to Human K-Ras," *Anal. Biochem.,* 244:191–4 (1997)). However, careful evaluation suggests these successes are limited to allele-specific primers discriminating through 3' purine-purine mismatches. For the more common transition mutations, the discriminating mismatch on the 3' primer end (i.e., G:T or C:A mismatch) will be removed in a small fraction of products by polymerase error during extension from the opposite primer on wild-type DNA. Thereafter, these error products are efficiently amplified and generate false-positive signal. One strategy to eliminate this polymerase error problem is to deplete wild-type DNA early in PCR.

Several investigators have explored selective removal of wild-type DNA by restriction endonuclease (RE) digestion in order to enrich for low abundance mutant sequences. These RFLP methods detect approximately 1 mutant in $10^6$ wild-type or better by combining the sensitivity of polymerase with the specificity of restriction endonucleases. One approach has used digestion of genomic DNA followed by PCR amplification of the uncut fragments (RFLP-PCR) to detect very low-level mutations within restriction sites in the H-ras and p53 genes (Sandy et al., "Genotypic Analysis of Mutations in Taq I Restriction Recognition Sites by Restriction Fragment Length Polymorphism/Polymerase Chain Reaction," *Proc. Natl. Acad. Sci. USA*, 89:890–4 (1992); and Pourzand et al., "Genotypic Mutation Analysis by RFLP/PCR," *Mutat. Res.*, 88(1):113–21 (1993)). Similar results have been obtained by digestion following PCR and subsequent amplification of the uncleaved DNA now enriched for mutant alleles (PCR-RFLP) (Kumar et al., "Oncogene Detection at the Single Cell Level," *Oncogene* 3(6):647–51 (1988); Kumar et al., "Designed Diagnostic Restriction Fragment Length Polymorphisms for The Detection of Point Mutations in Ras Oncogenes," *Oncogene Res.* 4(3):235–41 (1989); and Jacobson et al., "A Highly Sensitive Assay for Mutant Ras Genes and its Application to the Study of Presentation and Relapse Genotypes in Acute Leukemia," *Oncogene*, 9(2):553–63 (1994)). Although sensitive and rapid, RFLP detection methods are limited by the requirement that the location of the mutations must coincide with restriction endonuclease recognition sequences. To circumvent this limitation, primers that introduce a new restriction site have been employed in "primer-mediated" RFLP (Jacobson et al., "Rapid, Nonradioactive Screening for Activating Ras Oncogene Mutations Using PCR-Primer Introduced Restriction Analysis (PCR-PIRA)," *PCR Methods Appl.*, 1(4):299 (1992); Chen et al., "A Method to Detect Ras Point Mutations in Small Subpopulations of Cells," *Anal. Biochem.* 195(1):51–6 (1991); Di Giuseppe et al., "Detection of K-Ras Mutations in Mucinous Pancreatic Duct Hyperplasia from a Patient with a Family History of Pancreatic Carcinoma," *Am. J. Pathol.*, 144(5):889–95 (1994); Kahn et al., "Rapid and Sensitive Nonradioactive Detection of Mutant K-Ras Genes Via 'Enriched' PCR Amplification," *Oncogene*, 6:1079–83 (1991); Levi et al., "Multiple K-Ras Codon 12 Mutations in Cholangiocarcinomas Demonstrated with a Sensitive Polymerase Chain Reaction Technique," *Cancer Research*, 51(July):3497–502 (1991); and Mitsudomi et al., "Mutations of Ras Genes Distinguish a Subset of Non-Small-Cell Lung Cancer Cell Lines from Small-Cell Lung Cancer Cell Lines," *Oncogene*, 6(8):1353–62 (1991)). However, subsequent investigators have demonstrated that errors are produced at the very next base by polymerase extension from primers having 3' natural base mismatches (Hattori et al., "Mismatch PCR RFLP Detection of DRD2 Ser311Cys Polymorphism and Schizophrenia," *Biochem. Biophys. Res. Commun.*, 202(2):757–63 (1994); O'Dell et al., "PCR Induction of a TaqI Restriction Site at Any CpG Dinucleotide Using Two Mismatched Primers (CpG-PCR)," *Genome Res.*, 6(6):558–68 (1996); and Hodanova et al., "Incorrect Assignment of N370S Mutation Status by Mismatched PCR/RFLP Method in Two Gaucher Patients," *J. Inherit. Metab. Dis.*, 20(4):611–2 (1997)). Such templates fail to cleave during restriction digestion and amplify as false-positives that are indistinguishable from true positive products extended from mutant templates.

Use of nucleotide analogs may reduce errors resulting from polymerase extension and improve base conversion fidelity. Nucleotide analogs that are designed to base-pair with more than one of the four natural bases are termed "convertides." Base incorporation opposite different convertides has been tested (Hoops et al., "Template Directed Incorporation of Nucleotide Mixtures Using Azole-Nucleobase Analogs," *Nucleic Acids Res.*, 25(24):4866–71 (1997)). For each analog, PCR products were generated using Taq polymerase and primers containing an internal nucleotide analog. The products generated showed a characteristic distribution of the four bases incorporated opposite the analogs. Of significance, these products retained the original sequence at all natural base positions. Convertides readily form degenerate amplification products by virtue of their ability to assume different hydrogen bonding patterns through tautomeric shift (Brown et al., "Synthesis and Duplex Stability of Oligonucleotides Containing Adenine-Guanine Analogues," *Carbohydrate Research*, 216:129–39 (1991)), bond rotation (Bergstrom et al., *Nucleosides and Nucleotides*, 15(1–3):59–68 (1996)), or base stacking (Bergstrom et al., *Journal of the American Chemical Society*, 117:1201–9 (1995); and Zhang et al., "Exploratory Studies on Azole Carboxamides as Nucleobase Analogs: Thermal Denaturation Studies on Oligodeoxyribonucleotide Duplexes Containing Pyrrole-3-Carboxamide," *Nucleic Acids Res.*, 26:2208–15 (1998)). Thus, PCR primers containing convertides may be used to facilitate base conversion. In principle, using the 6H,8H-3,4-dihydropyrimido[4,5-c][1,2]oxazine-7-one analog $Q_6$), which is known to exhibit both the C-like and T-like tautomeric forms at the 3' end of the primer (Brown et al., "Synthesis and Duplex Stability of Oligonucleotides Containing Adenine-Guanine Analogues," *Carbohydrate Research*, 216:129–39 (1991)), a C-G base-pair may be converted to a T-A base pair (FIG. 1). Due to the better geometry, DNA polymerases may "read," or extend better, from a $Q_6$-G pair than a T-G mismatch (wobble base pair). Similarly, DNA polymerases may "write," or incorporate both G and A bases opposite $Q_6$ (Hill et al., "Polymerase Recognition of Synthetic Oligodeoxyribonucleotides Incorporating Degenerate Pyrimidine and Purine Bases," *Proc. Natl. Acad. Sci. USA*, 95(8):4258–63 (1998)), whereas A is always inserted opposite a T base. Thus, the $Q_6$ analog primer serves as an intermediary, providing a "preconversion" step before a natural base primer is added to selectively amplify the desired product from the degenerate pool. While nucleotide analogs have great potential, they have not been tested in high sensitivity assays. There is a need for a method that optimizes the fidelity of the analog conversion in the PCR process.

Optimization of PCR/RE/LDR

As discussed above, PCR used with a high fidelity conversion process would provide a valuable method for the amplification of mutant gene sequences. By designing primers with one or more mismatches, mutant DNA template can be efficiently extended, while poor extension is achieved on wild-type DNA template. However, once these primers extend with or without a mismatch, the products thereafter are perfect matches for the primer in subsequent PCR cycles. Thus, false positive signals are amplified in subsequent cycles. Moreover, PCR error can generate a base change in the template, which perfectly matches the primer. AS-PCR can detect pyrimidine↔purine transversions at sensitivities of 1 in $10^5$ (Newton et al., "Analysis of Any Point Mutation in DNA. The Amplification Refractory Mutation System (ARMS)," *Nucleic Acids Res.*, 17(7):2503–16 (1989); and Tada et al., "Detection of Ras Gene Mutations in Pancreatic Juice and Peripheral Blood of Patients with Pancreatic Adenocarcinoma," *Cancer Res.*, 53(11):2472–4 (1993)). Nevertheless, the majority of cancer-associated mutations are C↔T and A↔G transitions, as, for example, are over 80% of p53 point mutations (de Fromentel et al., *Genes Chromosomes Cancer*, 4(1):1–15 (1992)). A DNA diagnostic method is needed to accurately quantify this type of low abundance mutation.

The ligation detection reaction (LDR) in conjunction with PCR has been used to quantify small amounts of PCR extension product. LDR uses two adjacent primers and a thermostable ligase to distinguish all four bases potentially found at any position in a DNA sequence (Barany, F., "Genetic Disease Detection and DNA Amplification Using Cloned Thermostable Ligase," *Proc. Natl. Acad. Sci. USA*, 88:189–93 (1991); Barany, F., "The Ligase Chain Reaction in a PCR World," *PCR Methods Appl.*, 1:5–16 (1991); Day et al., "Detection of Steroid 21-Hydroxylase Alleles Using Gene-Specific PCR and a Multiplexed Ligation Detection Reaction," *Genomics*, 29:152–62 (1995); and Khanna et al., *Oncogene*, 18:27–38 (1999)). Thermostable ligase demonstrates the highest fidelity when the discriminating base is located at the 3' end of the upstream primer (Luo et al., "Improving the Fidelity of *Thermus Thermophilus* DNA Ligase," *Nucleic Acids Res.*, 24(15):3071–8 (1996)). PCR/LDR (PCR of a sequence from genomic DNA followed by LDR) can detect mutations with a sensitivity of approximately 1 mutant allele in 4,000 normal alleles (Khanna et al., *Oncogene*, 18:27–38 (1999)). Sensitivity of approximately 1 in $10^6$ has been achieved by combining PCR with restriction endonuclease digestion of wild-type DNA (Sandy et al., *Proc. Natl. Acad. Sci. USA*, 89:890–4 (1992); and Pourzand et al., "Genotypic Mutation Analysis by RFLP/PCR," *Mutat. Res.*, 288(1):113–21 (1993)). Mutations occurring within the restriction site prevent cleavage of the mutant allele, while wild-type alleles bearing canonical restriction site sequence are depleted. As a result, subsequent PCR cycles preferentially amplify mutant DNA. If a mutation site is not within an endonuclease recognition site present in wild-type DNA, a restriction site must be introduced. This is typically done by PCR using a primer or primers with mismatched bases. Mutations cannot be detected in any portion of the restriction site spanned by the primers, since those bases are introduced directly through the primers. In a random DNA sequence, over 20% of bases are contained within a preexisting four-base restriction site and 60% of bases are within a four-base subsequence that can be converted into a restriction site by a single base change. In these small sites, 3' terminal base mismatch primers must frequently be used. While conceptually straightforward, 3' mismatch extension has proven to be difficult (Newton et al., "Analysis of Any Point Mutation in DNA. The Amplification Refractory Mutation System (ARMS)," *Nucleic Acids Res.*, 17(7):2503–16 (1989); Kwok et al., "Effects of Primer-Template Mismatches on the Polymerase Chain Reaction: Human Immunodeficiency Virus Type 1 Model Studies," *Nucleic Acids Res*, 18(4):999–1005 (1990); O'Dell et al., *Genome Res.* 6(6):558–68 (1996); and Day et al., *Nucleic Acids Res.*, (1999)). The introduction of interrupted palindromic restriction sites has been more successful using internal mismatch primers spanning one half-site through the intervening bases up to the other half-site (Kumar et al., "Oncogene Detection at the Single Cell Level," *Oncogene* 3(6):647–51 (1988); and Anderson et al., "Prevalence of RAS Oncogene Mutation in Head and Neck Carcinomas," *J. Otolaryngol.*, 21(5):321–6 (1992)). Several perfectly matched bases stabilize the 3' end of the mismatch primer. However, this approach may be used only if the second half-site is present naturally in wild-type DNA. Mutations in the second half-site prevent digestion. Only mutations occurring at bases within the recognition sequence are detectable by RFLP methods. Mutations occurring at bases outside a preexisting restriction site in wild-type DNA may be detected by introducing a new restriction site containing that base.

Restriction endonucleases recognizing interrupted palindromes are less abundant than endonucleases recognizing contiguous four- and six-base sites. Multiple base changes would often be required to introduce an interrupted palindrome restriction site to identify mutations at any base.

More recently, methods of identifying known target sequences by probe ligation methods have been reported. U.S. Pat. No. 4,883,750 to N. M. Whiteley, et al.; D. Y. Wu, et al., *Genomics* 4:560 (1989), U. Landegren, et al., *Science* 241:1077 (1988), and E. Winn-Deen, et al., *Clin. Chem.* 37:1522 (1991). In one approach, known as oligonucleotide ligation assay ("OLA"), two probes or probe elements, that span a target region of interest, are hybridized to the target region. Where the probe elements base pair with adjacent target bases, the confronting ends of the probe elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction. When two complementary pairs of probe elements are utilized, the process is referred to as the ligase chain reaction, which achieves exponential amplification of target sequences. F. Barany, "Genetic Disease Detection and DNA Amplification Using Cloned Thermostable Ligase," *Proc. Nat'l Acad. Sci. USA*, 88:189–93 (1991) and F. Barany, "The Ligase Chain Reaction (LCR) in a PCR World," *PCR Methods and Applications*, 1:5–16 (1991); Barany, U.S. patent application filed Mar. 19, 1999, Ser. No. 60/125,251. Techniques, such as PCR/LDR, that rely on mutant enrichment require optimization of reaction conditions in order to minimize random PCR errors. These errors would be indistinguishable from mutations originally present in clinical samples. One source of error-minimization may be found in optimization of the buffer conditions for PCR. Standard PCR buffers contain Tris, however the $pK_a$ of Tris is strongly dependent on temperature. A PCR reaction containing Tris pH 8.3 (measured at 23° C.) is approximately pH 7 near 65° C. (the extension temperature), and drops to approximately pH 6 near 95° C. (the template melting temperature). PCR error can result from template degradation and polymerase misincorporation. Template degradation occurs during periods of high temperature and low pH in each PCR cycle and limits product size in "long" PCR (Barnes, "PCR Amplification of up to 35-Kb DNA with High Fidelity and High Yield from Lambda Bacteriophage Templates," *Proc. Natl. Acad. Sci. USA*, 91(6):2216–20 (1994); Cheng et al., "Effective Amplification of Long Targets from Cloned Inserts and Human Genomic DNA," *Proc. Natl. Acad. Sci. USA*, 91(12):5695–9 (1994); and Sang et al., "Generation of Site-Directed Mutagenesis by Extralong, High-Fidelity Polymerase Chain Reaction," *Anal. Biochem.*, 233(1):142–4 (1996)). Raising the buffer pH in long PCR (using Tris 9.1) reduces the amount of template cleavage and increases PCR efficiency (Barnes, "PCR Amplification of up to 35-Kb DNA with High Fidelity and High Yield from Lambda Bacteriophage Templates," *Proc. Natl. Acad. Sci. USA,* 91(6):2216–20 (1994)). Although the efficiency of long PCR increases with higher pH, the level of mutations within these PCR products may also increase since high pH decreases the fidelity of Taq and Pfu polymerases (Eckert et al., "High Fidelity DNA Synthesis by the *Thermus Aquaticus* DNA Polymerase," *Nucleic Acids Res.,* 18(13):3739–44 (1990); Eckert et al., "DNA Polymerase Fidelity and the Polymerase Chain Reaction," *PCR Methods Appl.,* 1(1):17–24 (1991); and Cline et al., "PCR Fidelity of Pfu DNA Polymerase and Other Thermostable DNA Polymerases," *Nucleic Acids Res.,* 24(18):3546–51 (1996)). Use of alternative PCR buffers with lower |ΔpKa| can improve polymerase fidelity and still reduce template damage by maintaining more neutral pH over a wider temperature range (Eckert et al., "DNA Polymerase Fidelity and the Polymerase Chain Reaction," *PCR Methods Appl.,* 1(1):17–24 (1991); and Brail et al., "Improved Polymerase Fidelity in PCR-SSCPA," *Mutat. Res.,* 303(4):171–5 (1993)). The addition of glycerol or formamide may reduce mutations arising from template damage during PCR cycling and may help avoid misextension from mispaired primers (Bottema et al., "PCR Amplification of Specific Alleles: Rapid Detection Of Known Mutations and Polymorphisms," *Mutat. Res.,* 288(1):93–102 (1993); and Cha et al., "Mismatch Amplification Mutation Assay (MAMA): Application to the C-H-Ras Gene," *PCR Methods Appl.,* 2(1):14–20 (1992)).

Thus, there is a need to improve buffer reaction conditions currently used in PCR, in order to minimize the opportunity for mismatches caused by PCR error. Increased analog conversion fidelity, alone, will not solve the need for an improved method of mutant DNA detection. In addition, there is a need to optimize PCR reaction conditions to decrease random PCR error, and finally, a method is needed that provides sensitive detection for the PCR extension products.

SUMMARY OF THE INVENTION

The present invention relates to a method for identifying one or more low abundance sequences differing by one or more single-base changes, insertions, or deletions, from a high abundance sequence, in a plurality of target nucleotide sequences. This method involves a first polymerase chain reaction phase, a second polymerase chain reaction phase, and a restriction endonuclease digest reaction phase, followed by a third polymerase chain reaction phase and a ligase detection reaction phase.

The starting sample of the present invention is a sample potentially containing one or more low abundance target nucleotide sequences with at least one sequence difference each from the high abundant target sequences present in the sample.

In the first polymerase chain reaction phase, a primary oligonucleotide primer set is provided. The primary oligonucleotide primer set has a first oligonucleotide primer containing a target-specific portion, and a second oligonucleotide primer containing a target-specific portion. The primary oligonucleotide primers are suitable for hybridization on complementary strands of a corresponding high and low abundance target nucleotide sequences to permit formation of a polymerase chain reaction product. However, the primers each have a mismatch which interferes with formation of such a polymerase chain reaction product when hybridized to any other nucleotide sequence present in the sample. The primary oligonucleotide primers, the sample, and a polymerase are blended to form a primary polymerase chain reaction mixture.

The primary polymerase chain reaction mixture is subjected to two or more polymerase chain reaction cycles involving a denaturation treatment, a hybridization treatment, and an extension treatment. The denaturing treatment separates hybridized nucleic acid sequences. The hybridization treatment causes the target-specific portions of the primary oligonucleotide primers to hybridize to the target nucleotide sequences. The extension treatment causes the hybridized primary oligonucleotide primers to be extended to form primary extension products complementary to the target nucleotide sequence to which the primary oligonucleotide primer is hybridized.

Next, there is a second polymerase chain reaction phase. This phase involves providing a secondary oligonucleotide primer set having a first oligonucleotide primer with a target-specific portion and a 5' upstream secondary primer-specific portion and a second oligonucleotide primer with a target-specific portion and a 5' upstream secondary primer-specific portion. The secondary oligonucleotide primers in a particular set are suitable for hybridization on complementary strands of the primary extension products to permit formation of a secondary polymerase chain reaction product which contains or creates a restriction endonuclease recognition site when amplifying the high abundance target, but does not contain or create a restriction endonuclease recognition site when amplifying the one or more low abundance targets. The primary extension products, the secondary oligonucleotide primers, and the polymerase are blended to form a secondary polymerase chain reaction mixture.

The secondary polymerase chain reaction mixture is subjected to two or more polymerase chain reaction cycles comprising a denaturation treatment, a hybridization treatment, and an extension treatment. The denaturation treatment involves separation of hybridized nucleic acid sequences. In the hybridization treatment, the secondary oligonucleotide primers hybridize to the primary extension products. The extension treatment causes the hybridized primary extension products to form secondary extension products complementary to the primary extension products. The high abundance secondary extension products contain a restriction site but the low abundance secondary extension products do not.

The next phase involves blending a restriction endonuclease with the secondary extension products to form an endonuclease digestion reaction mixture. The restriction endonuclease is one that cleaves, with specificity, the restriction endonuclease recognition site within or created when amplifying the high abundance target, but not the low abundance target in the secondary extension products. The restriction endonuclease digestion selectively destroys the high abundance secondary extension products.

Next, there is a third polymerase chain reaction phase. This involves providing a tertiary oligonucleotide primer set having a first tertiary primer containing the same sequence as the 5' upstream portion of the first oligonucleotide primer of the secondary oligonucleotide primer set and a second tertiary primer containing the same sequence as the 5' upstream portion of a second oligonucleotide primer of the secondary oligonucleotide primer set. The set of tertiary oligonucleotide primers may be used to amplify all of the secondary extension products. The secondary extension products are blended with the tertiary oligonucleotide primer set, and a polymerase to form a tertiary polymerase chain reaction mixture.

The tertiary polymerase chain reaction mixture is subjected to two or more polymerase chain reaction cycles comprising a denaturation treatment, a hybridization treatment, and an extension treatment. The denaturation treatment causes the hybridized nucleic acid sequences to be separated, while the hybridization treatment involves hybridization of the tertiary oligonucleotide primers to hybridize to the secondary extension products. During the extension treatment, the hybridized tertiary oligonucleotide primers are extended to form tertiary extension products complementary to the uncleaved secondary extension products.

Next, the tertiary extension products are subjected to a ligase detection reaction. This involves providing a plurality of oligonucleotide probe sets, each set having a first oligonucleotide probe, having a tertiary extension product-specific portion and a detectable reporter label, and a second oligonucleotide probe, having a tertiary extension product-specific portion. The oligonucleotide probes in a particular LDR probe set are suitable for ligation when hybridized adjacent to one another on a complementary tertiary extension product-specific portion. However, there is a mismatch which interferes with such ligation when hybridized to any other nucleotide sequence present in the sample.

The tertiary extension products, the plurality of oligonucleotide probe sets, and a ligase are blended to form a ligase detection reaction mixture.

The ligase detection reaction mixture is subjected to one or more ligase detection reaction cycles having a denaturation treatment, and a hybridization treatment. The denaturation treatment involves separation of hybridized oligonucleotides from the tertiary extension products. In the hybridization treatment, the oligonucleotide probe sets hybridize at adjacent positions in a base-specific manner to their respective tertiary extension products, if present. As a result, adjacent probes ligate to one another to form a ligation product sequence containing the detectable reporter label and the tertiary extension product-specific portions connected together. The oligonucleotide probe sets may hybridize to nucleotide sequences other than their respective complementary tertiary extension products but do not ligate together due to a presence of one or more mismatches and individually separate during the denaturation treatment. Following the ligase detection reaction cycles, the reporter labels of the ligation product sequences are detected which indicates the presence of one or more low abundance target nucleotide sequences in the sample.

The present invention also relates to a kit for identifying one or more low abundance sequences differing by one or more single-base changes, insertions, or deletions, from a high abundance sequence in a plurality of target nucleotide sequences. This kit provides a primary oligonucleotide primer set, a secondary oligonucleotide primer set, a tertiary oligonucleotide primer set, and a plurality of oligonucleotide probe sets.

The primary oligonucleotide primer set provided in the kit has (a) a first oligonucleotide primer containing a target-specific portion, and (b) a second oligonucleotide primer containing a target-specific portion. The primary oligonucleotide primers are suitable for hybridization on complementary strands of a corresponding high and low abundance target nucleotide sequences to permit formation of a primary extension product. However, the primers have a mismatch which interferes with formation of such a polymerase chain reaction product when hybridized to any other nucleotide sequence present in the sample.

The secondary oligonucleotide primer set provided in the kit has (a) a first oligonucleotide primer, containing a target-specific portion and a 5' upstream secondary primer-specific portion, and (b) a second oligonucleotide primer, containing a target-specific portion and a 5' upstream secondary primer-specific portion. The secondary oligonucleotide primers are suitable for hybridization on complementary strands of the primary extension products to permit formation of a secondary extension product which contains or creates a restriction endonuclease recognition site when amplifying the high abundance target, but does not contain or create a restriction endonuclease recognition site when amplifying the one or more low abundance targets.

The tertiary oligonucleotide primer set provided in the kit have (a) a first tertiary primer containing the same sequence as the 5' upstream portion of the first oligonucleotide primer of the secondary oligonucleotide primer set, and (b) a second tertiary primer containing the same sequence as the 5' upstream portion of a second oligonucleotide primer of the secondary oligonucleotide primer set. The set of tertiary oligonucleotide primers may be used to amplify all of the secondary extension products.

The kit also provides a plurality of oligonucleotide probe sets. Each set has (a) a first oligonucleotide probe, containing a tertiary extension product-specific portion and a detectable reporter label, and (b) a second oligonucleotide probe, containing a tertiary extension product-specific portion. The oligonucleotide probes in a particular set are suitable for ligation together when hybridized adjacent to one another on a complementary tertiary extension product-specific portion. However, the probes have a mismatch which interferes with such ligation when hybridized to any other nucleotide sequence present in the sample.

There is not currently available a biological technique that is sensitive enough to detect and identify one or more low abundance sequences differing by one or more single-base changes, insertions, or deletions, from a high abundance sequence, in a plurality of target nucleotide sequences, without the potential for many errors during the amplification and detection stages. The present invention is directed to overcoming these and other deficiencies in the art, by providing a method which optimizes the conditions for selective amplification of low abundance DNA targets through polymerase chain reaction and restriction endonuclease digestion, and a method of nucleotide detection, that combined, creates a highly sensitive method for the amplification and detection of low abundance nucleotides sequences such as mutant genes. This procedure is useful for clinical and research applications.

Figure 1A:
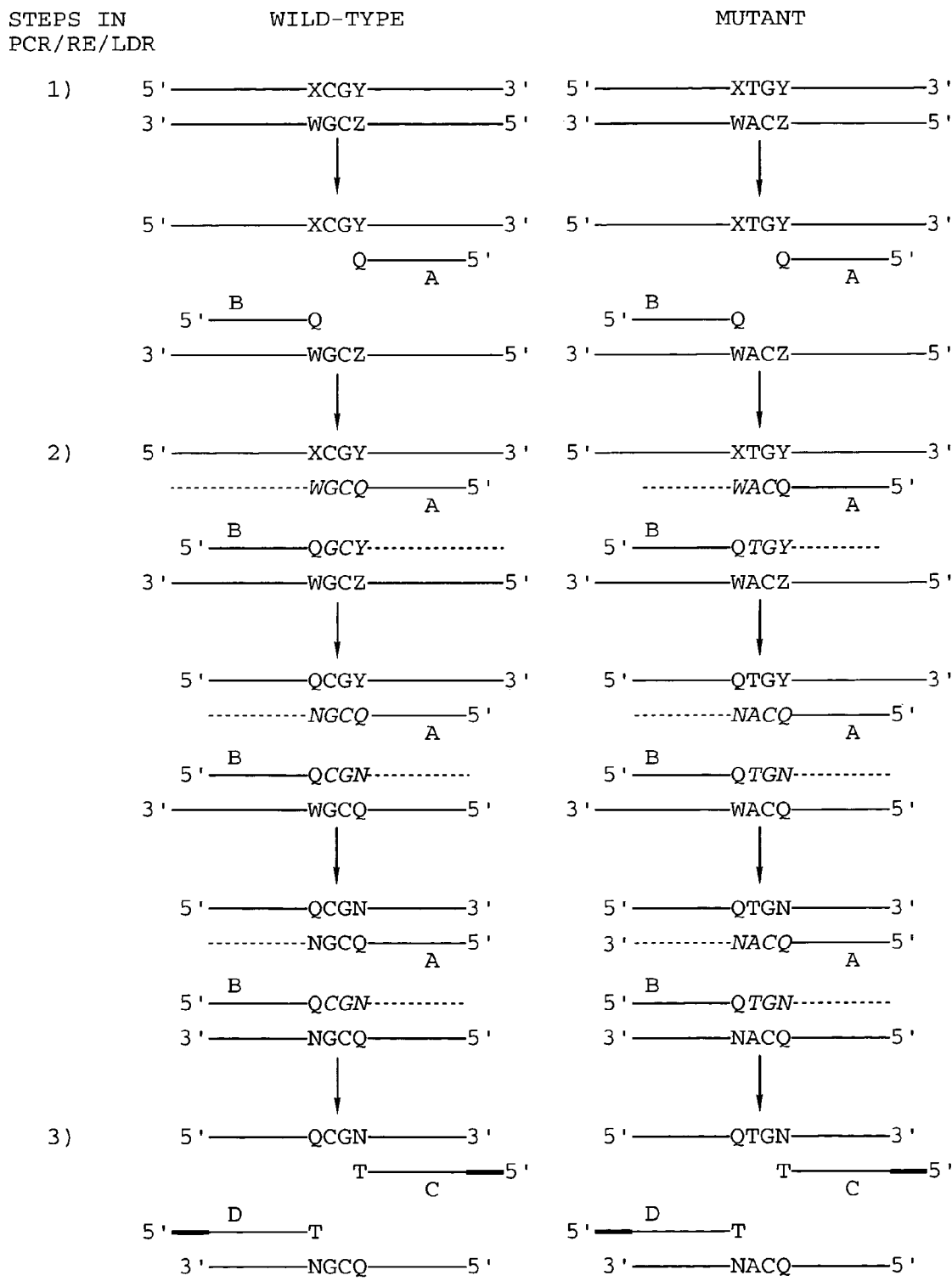
FIGS. 1A–C are a schematic drawing of the coupled polymerase chain reaction-restriction endonuclease digestion-ligase detection reaction process of the present invention.

During PCR, the reverse primer anneals to the $Q_6$ PCR product and is extended by polymerase to synthesize the opposite strand. When polymerase reaches the $Q_6$ analog in the template, polymerase writes A (or G, not shown) opposite the analog and continues synthesis of the strand. After a few cycles, a pool of products is made with degenerate sequence opposite the analogs. A natural base primer is then added to selectively amplify the products having the desired base change.

FIGS. 5A–I shows the nucleotide analogs used in PCR primers. In the final deprotected oligonucleotide, the name of the nucleoside containing the base analog shown are as follows: $Q_1$, 1-(2'-deoxy-β-D-ribofuranosyl)imidazole-4-carboxamide (FIG. 5A); $Q_2$, 1-(2'-deoxy-β-D-ribofuranosyl)-3-nitropyrrole (FIG. 5B); $Q_5$, 2'-deoxyinosine (FIG. 5C); $Q_6$, 6-(2'-deoxy-β-D-ribofuranosyl)-6H,8H-3,4-dihydropyrimido[4,5-c][1,2]oxazine-7-one (FIG. 5D); $Q_7$, 2-amino-7-(2'-deoxy-β-D-ribofuranosyl)-6-methoxyaminopurine (FIG. 5E); $Q_{16}$, 1-(21-deoxy-β-D-ribofuranosyl)-4-iodopyrazole (FIG. 5F); $Q_{18}$, 1-(2'-deoxy-β-D-ribofuranosyl)pyrrole-3-carboxamide (FIG. 5G); $Q_{19}$, 1-(2'-deoxy-β-D-ribofuranosyl)-4-nitropyrazole (FIG. 5H). Base analogs (Q) are attached to the 1' position of deoxyribofuranose. The nucleoside analogs are attached to the controlled pore glass (CPG) column via a succinyl linker (R=linker to CPG). The oligonucleotide is synthesized from the 5' hydroxyl after removal of the dimethoxytrityl (DMT) protecting group, placing the analog at the 3' end. After cleavage from the CPG column and deprotection, the oligonucleotide is extended by polymerase from the 3' base analog hydroxyl group (R=H) (FIG. 5I).

FIGS. 6A–C show the primers used in mismatch extension and 3' nucleotide analog conversion. Complementary (–strand) sequences are shown in reverse orientation (3–5'), e.g., reverse strand primers (names ending in "R"). In FIG. 6A, one of nine different synthetic 50 bp duplex templates (–strand, SEQ. ID. No. 1; +strand, SEQ. ID. No. 2) is shown melted with primers aligned to complementary sequence. Primer extension was performed using 3' natural base and nucleotide analog primers p53-248X (SEQ. ID. No. 3) and p53-248XR (SEQ. ID. No. 4). Some extension products were reamplified using truncated zipcode primers p53zip248 (SEQ. ID. No. 5) and p53zip248R (SEQ. ID. No. 6) and sequenced using one of the zipcode primers Ztop (SEQ. ID. No. 7) or Zbot (SEQ. ID. No. 8). In FIG. 6B, preconversion was performed on nine different 50 bp synthetic duplex templates (only one template, SEQ. ID. Nos. 1 and 2 is shown) using 3' nucleotide analog primers, e.g., p53-248$Q_6$ (SEQ. ID. No. 3) and p53-248$Q_6$R (SEQ. ID. No. 4). Conversion, with or without preconversion, was performed using primers containing 3' natural base, e.g. primers p53zip248T (SEQ. ID. No. 9) and p53zip248TR (SEQ. ID. No. 10). These conversion products were reamplified using zipcode primers and identified by LDR. In FIG. 6C, LDR probe sets were designed to identify specific base changes in conversion products. LDR probes anneal in competition with each other to conversion products. Perfectly complementary upstream and downstream LDR probes with no overlap or gap ligate with high specificity. Discriminating probes had different length 5' tails to allow specific product separation on an acrylamide gel. A set of probes used to identify PCR error products in nonconversion of wild-type template is shown in FIG. 6C: p53LDR248FCA (SEQ. ID. No. 11), p53LDR248FCG (SEQ. ID. No. 12), p53LDR248FCT (SEQ. ID. No. 13), p53LDR248FCC (SEQ. ID. No. 14), and p53LDR248PGG (SEQ. ID. No. 15), and potential conversion product(s) (SEQ. ID. No. 16).

Figure 7A:
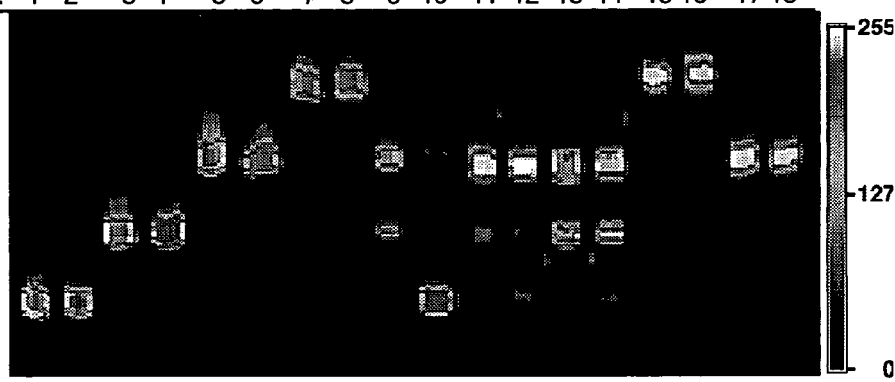
Figure 7B:
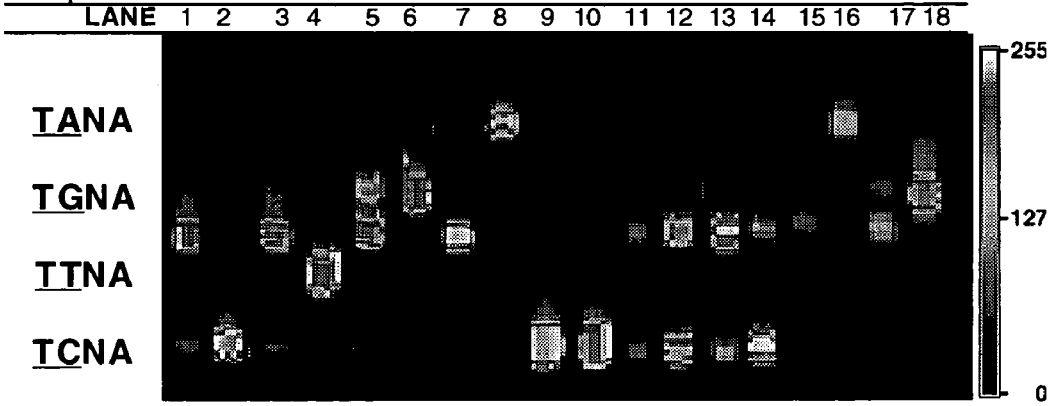

FIGS. 7A–B show results of a conversion by natural base and $Q_6$ convertide. Conversion products from nine templates were detected by PCR/LDR. Each template was a 50-base pair synthetic duplex DNA of identical sequence except for the central four bases which have the sequence indicated. As shown in FIGS. 7A–B, template CCGG refers to SEQ. ID. No. 2 (as shown in FIGS. 6A–B), template CTGG refers to SEQ. ID. No. 17, template CGGG refers to SEQ. ID. No. 18, template CAGG refers to SEQ. ID. No. 19, template TCGA refers to SEQ. ID. No. 20, template GCGC refers to SEQ. ID. No. 21, template ACGT refers to SEQ. ID. No. 22, template CATG refers to SEQ. ID. No. 23, and template CGCG refers to SEQ. ID. No. 24. Conversion occurred within these four bases. The expected conversion products produced by starting with the conversion primers having the indicated 3' natural base or convertide are shown. FIG. 7A shows the conversion of the first base to C using primer p53zip248C (SEQ. ID. No. 25) with and without $Q_6$ preconversion. FIG. 7B shows the conversion of the first base to T using primer p53zip248T (SEQ. ID. No. 9) with and without $Q_6$ preconversion.

Figure 8A:
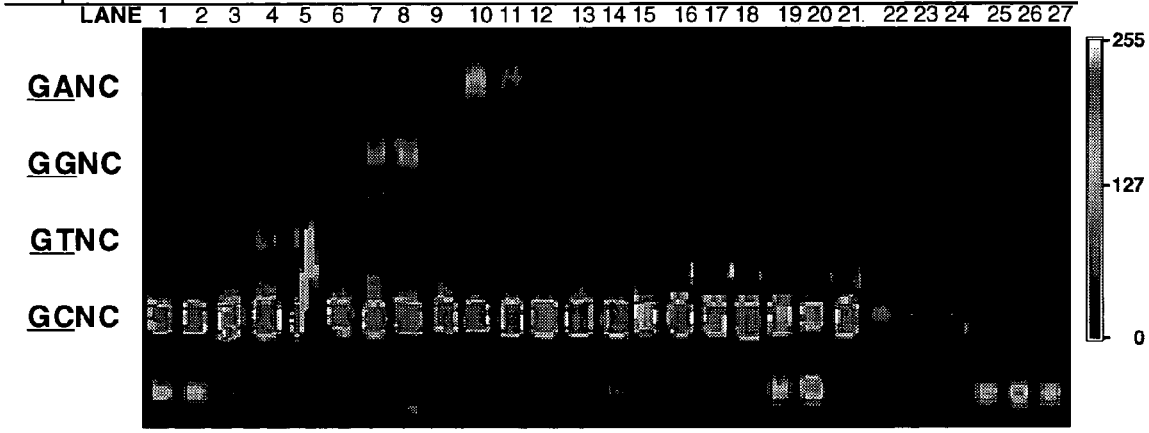
Figure 8B:
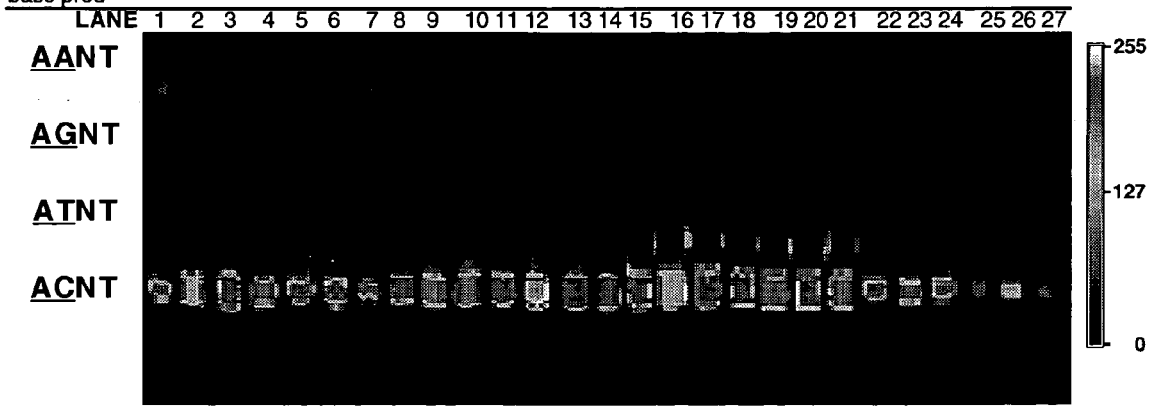

FIGS. 8A–B shows conversion by natural base, $Q_5$, and $Q_7$ convertides. Conversion products from nine templates, corresponding to SEQ. ID. Nos. 2 and 17–24, were detected by PCR/LDR. Each template was a 50-base pair synthetic duplex DNA of identical sequence except for the central four bases which have the sequence indicated. Conversion occurred within these four bases. The expected conversion products produced by starting with the conversion primers having the indicated 3' natural base or convertide are shown. FIG. 8A shows conversion of the first base to G using primer p53zip248G (SEQ. ID. No. 26) with and without $Q_5$ or $Q_7$ preconversion. FIG. 8B shows conversion of the first base to A using primer p53zip248A (SEQ. ID. No. 27) with and without $Q_5$ or $Q_7$ preconversion.

Figure 9A:
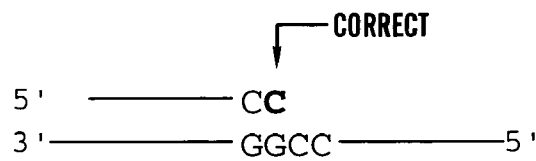
Figure 9E:
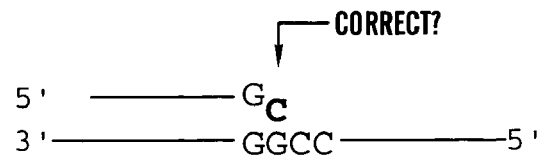
Figure 9B:
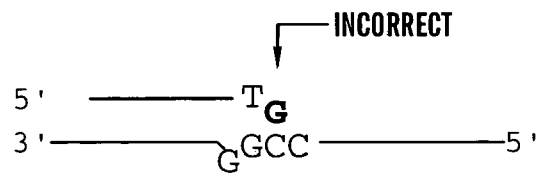
Figure 9F:
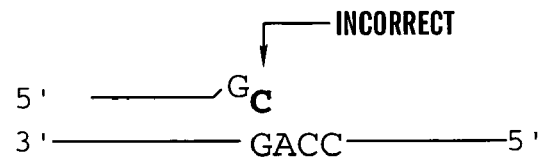
Figure 9C:
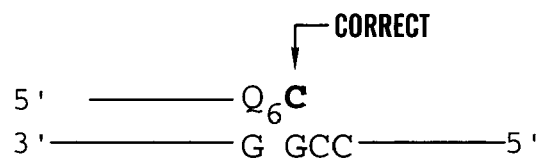
Figure 9G:
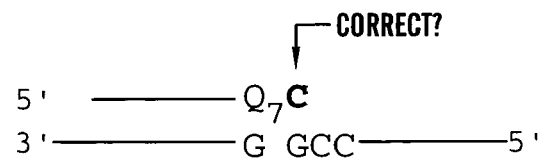
Figure 9D:
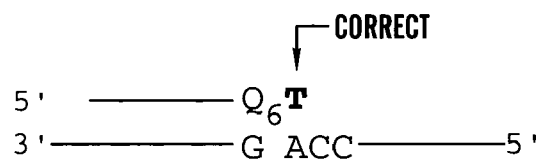
Figure 9H:
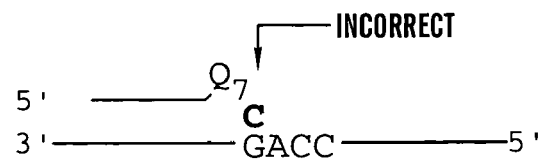

FIGS. 9A–H show the fidelity of polymerase extension. Primer slippage accounts for many of the observed products of extension (FIG. 7 and FIG. 8). In FIG. 9A, perfectly complementary primer gives correct product. For FIG. 9B, a T:G mismatch at the second base explains TGGA (or TGCA) product. In FIG. 9C, extension from a $Q_6$:G pairing with no slippage on the minus strand of the CCGG template (followed by 3' T conversion primers) resulted in the expected TCGA product. FIG. 9D shows extension from a $Q_6$:G pairing with no slippage on the minus strand of the CTGG template and several other templates (followed by 3' T conversion primers) resulted in the expected products. In FIG. 9E, GG mismatch extension apparently gave the expected GC product on one template, but perhaps only fortuitously (see FIG. 9F). For FIG. 9F, all extensions from GG mismatches gave GC extension products, consistent with a GT mismatch formed by slippage at the preceding base. In FIG. 9G, $Q_5$:G and $Q_7$:G extension products apparently gave the expected GC product on one template, but perhaps only fortuitously (see FIG. 9H). In FIG. 9H, all extensions from $Q_5$:G and $Q_7$:G mismatches (followed by 3' G conversion primers) gave GC extension products consistent with a $Q_5$:T or $Q_7$:T mismatch at the preceding base.

Figure 10A:
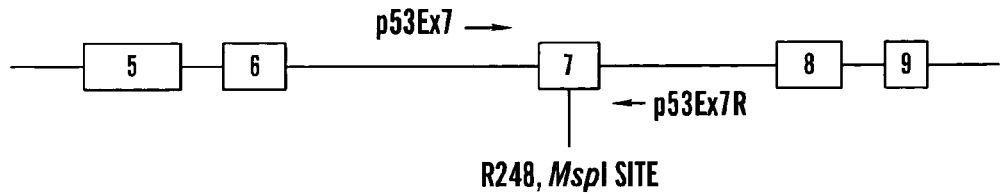
Figure 10B:
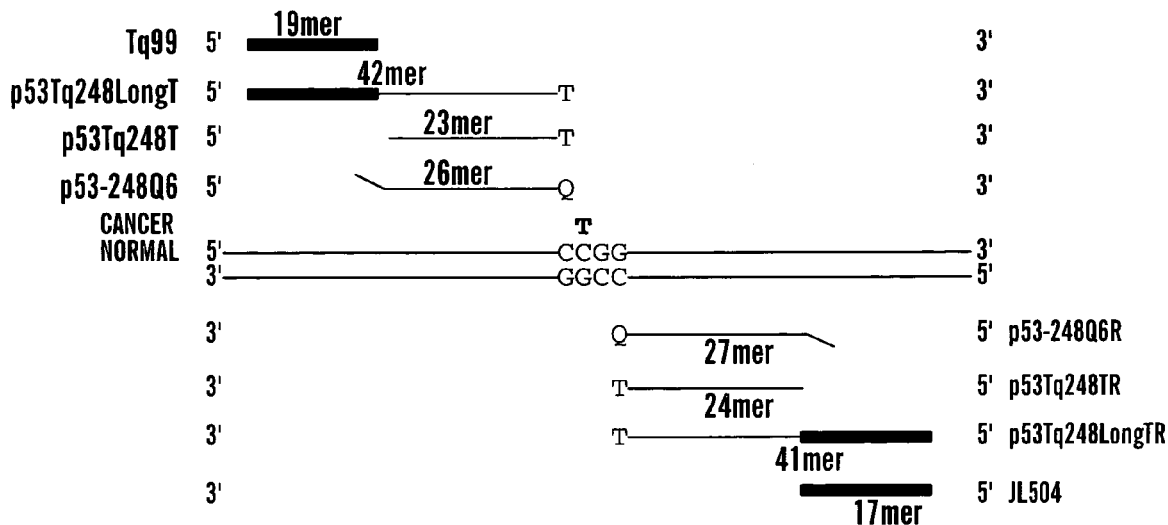
Figure 10C:
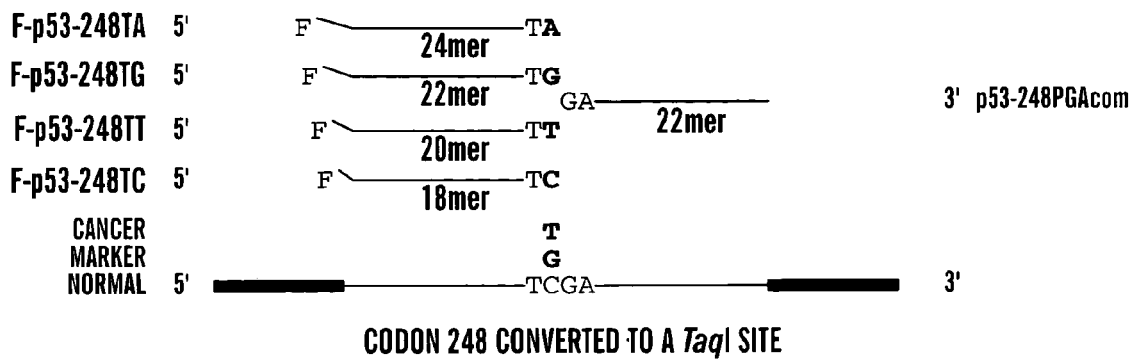

FIGS. 10A–C is a schematic of the amplification of p53 exon 7 from genomic DNA (FIG. 10A), and conversion of the normal MspI site to a TaqI site. First, the template is subjected to PCR amplification of the p53 Exon 7 (FIG. 10B). Next, a PCR conversion step is carried out, resulting in the conversion of codon 248 to a the to create a (TCGA) TaqI restriction site (FIG. 10B).

FIGS. 11A–C show the PCR primers used to determine polymerase fidelity by PCR/RE/LDR at a preexisting restriction site to avoid conversion error. The method used is as described in FIG. 6 for conversion steps. However, in the fidelity experiments shown in FIG. 11, the buffer components were modified, to test for optimal buffer conditions within the conversion process. FIG. 11A shows a PCR fidelity assay. A synthetic 50-base pair duplex marker template (MK) and wild-type p53 exon 7 PCR product (−strand, SEQ. ID. No. 1; +strand, SEQ. ID. No. 2) are mixed at known ratios in parallel reactions. Perfect match primers p53-248short (SEQ. ID. No. 28) and p53-248shortR (SEQ. ID. No. 29) amplify the wild-type CCGG and marker CGGG. Then, longer zipcode containing primers p53zip248short (SEQ. ID. No. 5) and p53zip248shortR (SEQ. ID. No. 6) were added. Finally, wild-type was repeatedly digested and reamplified with zipcode primers Ztop (SEQ. ID. No. 7) and Zbot (SEQ. ID. No. 8). In FIG. 11B, preconversion was performed using primers containing 3' convertide; e.g., p53-248$Q_6$ (SEQ. ID. No. 3). Conversion of the MspI site to a TaqI site with or without preconversion was performed using 3' natural base primers p53zip248T (SEQ. ID. No. 9) and p53zip248TR (SEQ. ID. No. 10). Long primers were added as above and conversion products further amplified. Wild-type products were digested with the restriction endonuclease appropriate for the new site. Mutant products were preferentially amplified with zipcode primers. Other primers in FIG. 11B include p53Taq248T (SEQ. ID. No. 30), p53Taq248TR (SEQ. ID. No. 31), p53Taq248$Q_6$ (SEQ. ID. No. 32), and p53Taq248$Q_6$R (SEQ. ID. No. 4). In FIG. 11C, LDR probe sets were designed to query the template sequence around the point of ligation. Perfectly hybridized upstream and downstream LDR probes with no overlap or gap are preferentially ligated with high specificity. Discriminating probes have different length 5' tails to allow specific product separation on an acrylamide gel. Probes shown (SEQ. ID. Nos. 11–14, as described in FIG. 6C) were used for identification of mutations occurring in the second base of the MspI site (no conversion). An extra probe, p53LDR248FTCL (SEQ. ID. No. 33), was used to compare C—T transitions at the first base and second base of the MspI site. A comparable set of discriminating and common probes were used to identify mutations at the second base of the TaqI site in conversion products (SEQ. ID. No. 34) had a T at the 3' penultimate base in the discrimination primers and A at the 5' penultimate base in the common probe.

Figure 12A:
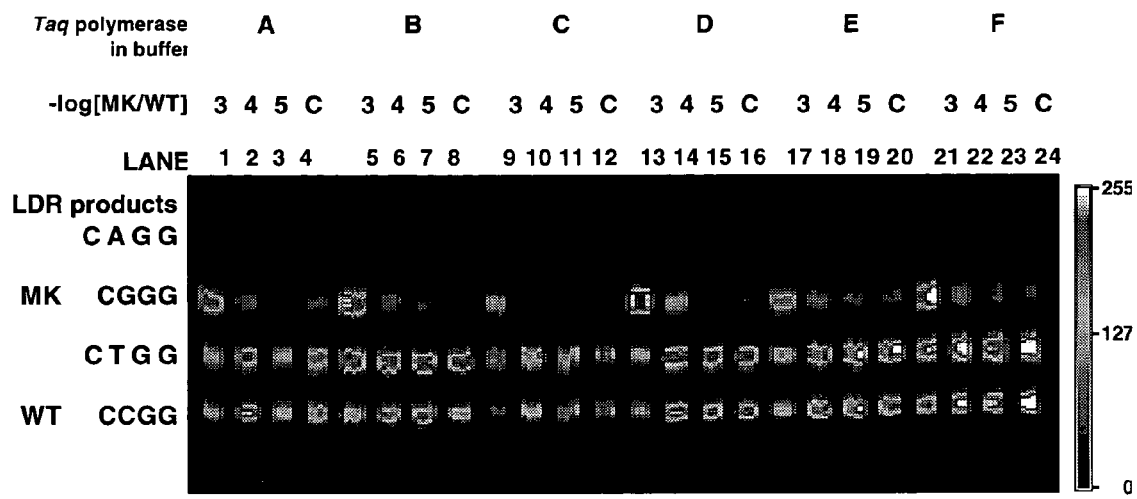
Figure 12B:
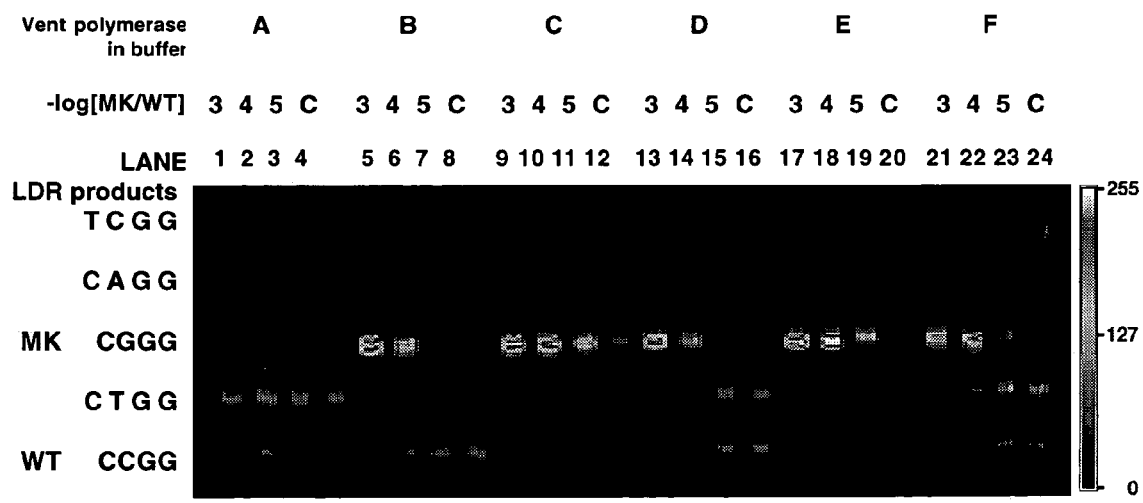

FIGS. 12A–B show the buffer and enzyme dependent PCR errors detected by the PCR/RE/LDR experiments shown in FIG. 11. The indicated polymerase/buffer combinations were used to amplify p53 exon 7 from genomic DNA. The same buffers were used in reactions with perfect match primers to reamplify the MspI site. In FIG. 12A, Taq polymerase (T) was used in various test PCR buffers, while in FIG. 12B, Vent polymerase (V) was used in various test buffers. Vent polymerase did not amplify p53 exon 7 from genomic DNA in TsK, buffer A, buffer. In this case only, two different enzyme/buffer sets were used for preamplification and "conversion" (not actual conversion, since perfect match primers were used). The AmpliTaq T/TsK exon 7 genomic DNA PCR product was substituted in the Vent V/TsK, buffer A, reamplification. "C" indicates no MK was added (control reaction).

Figure 13:
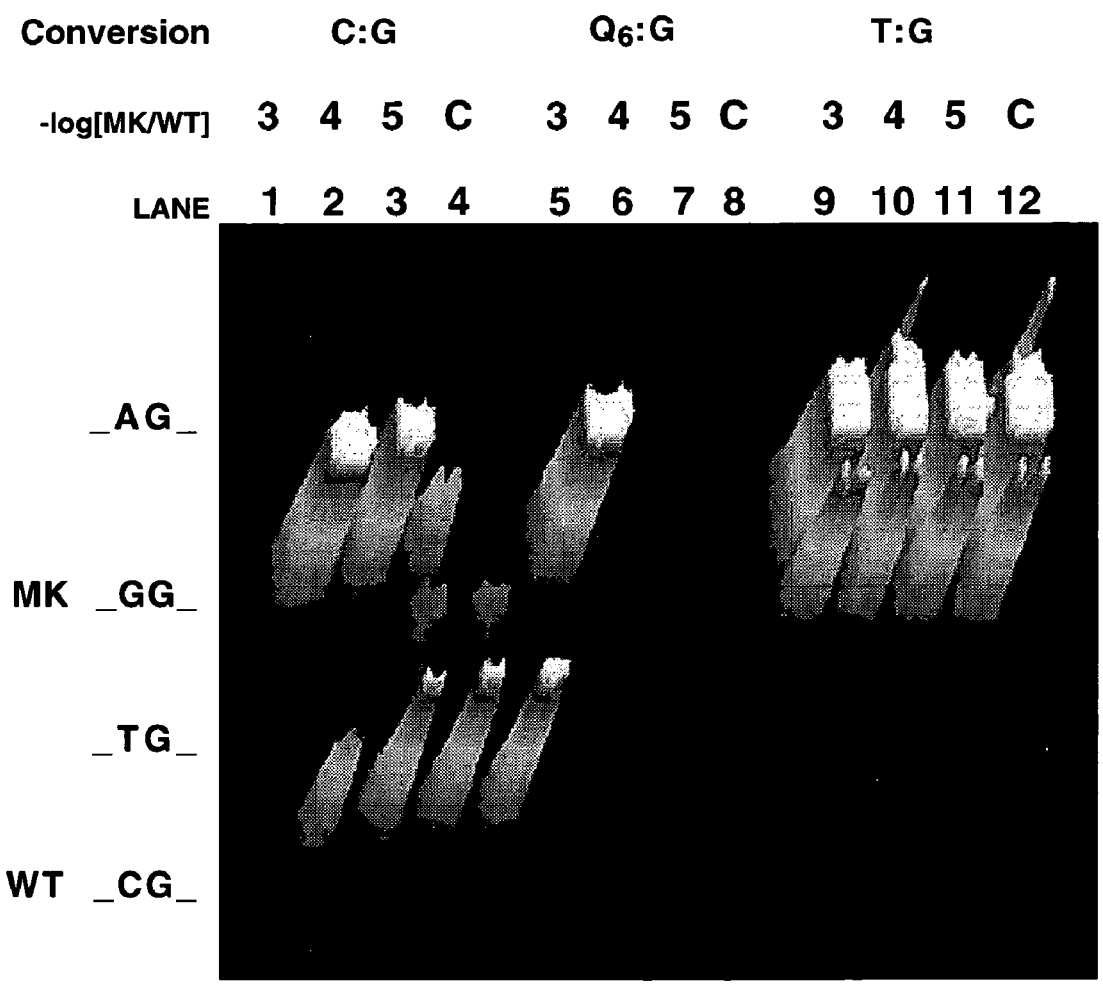

FIG. 13 shows the results of a comparison of conversion fidelity. The relative intensities of conversion reaction products is indicated by color and the height of each peak in a 3-D plot. Marker (MK) DNA (with CGGG replacing the MspI site) was added at known ratios to wild-type (WT) in parallel reactions. The −log(MK:WT) indicates relative fraction of MK present, e.g., −log(MK:WT)=3 means the ratio of MK to WT was 1:1000. "C" indicates no MK was added (control reaction). Nonconversion control reactions (C:G) were performed using perfect match 3' C primers. Conversion of the MspI site (CCGG) to a TaqI site (TCGA) was performed using natural base 3' T primers with and without preconversion using 3' $Q_6$ nucleotide analog primers ($Q_6$:G and T:G reactions, respectively). LDR products from MspI nonconversion contain CNGG, and products from TaqI conversion contain TNGA, but only the central bases (second and third bases) are indicated as _NG_. The LDR products were designed to separate on acrylamide gels by two base differences in size. Some undetermined bands of intermediate size were also observed. Lanes 1–4 were digested with MspI, while lanes 5–12 were digested with TaqI during PCR/RE/LDR.

DETAILED DESCRIPTION OF THE INVENTION

The present invention relates to a method for identifying one or more low abundance sequences differing by one or more single-base changes, insertions, or deletions, from a high abundance sequence, in a plurality of target nucleotide sequences. This method involves a first polymerase chain reaction phase, a second polymerase chain reaction phase, and a restriction endonuclease digestion reaction phase, followed by a third polymerase chain reaction phase and a ligase detection reaction phase.

The starting sample of the present invention is a sample potentially containing one or more low abundance target nucleotide sequences with at least one sequence difference each from the high abundance target sequences present in the sample.

In the first polymerase chain reaction phase, a primary oligonucleotide primer set is provided. The primary oligonucleotide primer set has a first oligonucleotide primer containing a target-specific portion, and a second oligonucleotide primer containing a target-specific portion. The primary oligonucleotide primers are suitable for hybridization on complementary strands of a corresponding high and low abundance target nucleotide sequences to permit formation of a polymerase chain reaction product. However, the primers each have a mismatch which interferes with formation of such a polymerase chain reaction product when hybridized to any other nucleotide sequence present in the sample. The primary oligonucleotide primers, the sample, and a polymerase are blended to form a primary polymerase chain reaction mixture.

The primary polymerase chain reaction mixture is subjected to two or more polymerase chain reaction cycles involving a denaturation treatment, a hybridization treatment, and an extension treatment. The denaturation treatment separates hybridized nucleic acid sequences. The hybridization treatment causes the target-specific portions of the primary oligonucleotide primers to hybridize to the target nucleotide sequences. The extension treatment causes the hybridized primary oligonucleotide primers to be extended to form primary extension products complementary to the target nucleotide sequence to which the primary oligonucleotide primer is hybridized.

The efficiency and accuracy of converting the high abundance primary polymerase chain reaction product into a secondary polymerase chain reaction product containing a restriction endonuclease site may be improved by performing a step (referred to a "preconversion") prior to providing the secondary oligonucleotide primer set. This step consists of providing a pre-secondary oligonucleotide primer set having (a) a first oligonucleotide primer, with a target-specific portion, and (b) a second oligonucleotide primer, with a target-specific portion. The target-specific portions are identical or substantially identical to the secondary oligonucleotide primer set but at least one primer contains one or more nucleotide analogs. The oligonucleotides in a particular pre-secondary primer set are suitable for hybridization on complementary strands of the primary extension products. The primary extension product is denatured, and the primary extension products are blended with a polymerase and the pre-secondary oligonucleotide primers to form a pre-secondary polymerase chain reaction mixture. The mixture is subjected to two or more PCR cycles to permit the formation of a pre-secondary polymerase chain reaction product. This product contains one or more nucleotide analogs and opposite strand base changes, which facilitates the conversion of the primary polymerase chain reaction product sequence into a restriction endonuclease recognition site in the subsequent secondary polymerase chain reaction.

Next, there is a second polymerase chain reaction phase. This phase involves providing a secondary oligonucleotide primer set having a first oligonucleotide primer with a target-specific portion and a 5' upstream secondary primer-specific portion and a second oligonucleotide primer with a target-specific portion and a 5' upstream secondary primer-specific portion. The secondary oligonucleotide primers in a particular set are suitable for hybridization on complementary strands of the primary extension products to permit formation of a secondary polymerase chain reaction product which contains or creates a restriction endonuclease recognition site when amplifying the high abundance target, but does not contain or create a restriction endonuclease recognition site when amplifying the one or more low abundance targets. The primary extension products, the secondary oligonucleotide primers, and the polymerase are blended to form a secondary polymerase chain reaction mixture.

The secondary polymerase chain reaction mixture is subjected to two or more polymerase chain reaction cycles comprising a denaturation treatment, a hybridization treatment, and an extension treatment. The denaturation treatment involves separation of hybridized nucleic acid sequences. In the hybridization treatment, the secondary oligonucleotide primers hybridize to the primary extension products. The extension treatment causes the hybridized primary extension products to form secondary extension products complementary to the primary extension products. The high abundance secondary extension products contain a restriction site but the low abundance secondary extension products do not.

The next phase involves blending a restriction endonuclease with the secondary extension products to form an endonuclease digestion reaction mixture. The restriction endonuclease is one that recognizes and cleaves the restriction endonuclease recognition site within or created when amplifying the high abundance target, but not the low abundance target in the secondary extension products. The restriction endonuclease digestion selectively destroys the high abundance secondary extension products.

Next, there is a third polymerase chain reaction phase. This involves providing a tertiary oligonucleotide primer set having a first tertiary primer containing the same sequence as the 5' upstream portion of the first oligonucleotide primer of the secondary oligonucleotide primer set and a second tertiary primer containing the same sequence as the 5' upstream portion of a second oligonucleotide primer of the secondary oligonucleotide primer set. The set of tertiary oligonucleotide primers may be used to amplify all of the secondary extension products. The secondary extension products are blended with the tertiary oligonucleotide primer set, and a polymerase to form a tertiary polymerase chain reaction mixture.

The tertiary polymerase chain reaction mixture is subjected to two or more polymerase chain reaction cycles comprising a denaturation treatment, a hybridization treatment, and an extension treatment. The denaturation treatment causes the hybridized nucleic acid sequences to be separated, while the hybridization treatment involves hybridization of the tertiary oligonucleotide primers to hybridize to the secondary extension products. During the extension treatment, the hybridized tertiary oligonucleotide primers are extended to form tertiary extension products complementary to the secondary extension products.

Next, the tertiary extension products are subjected to a ligase detection reaction. This involves providing a plurality of oligonucleotide probe sets, each set having a first oligonucleotide probe, having a tertiary extension product-specific portion and a detectable reporter label, and a second oligonucleotide probe, having a tertiary extension product-specific portion. The oligonucleotide probes in a particular set are suitable for ligation together when hybridized adjacent to one another on a complementary tertiary extension product-specific portion. However, there is a mismatch which interferes with such ligation when hybridized to any other nucleotide sequence present in the sample.

The tertiary extension products, the plurality of oligonucleotide probe sets, and a ligase are blended to form a ligase detection reaction mixture.

The ligase detection reaction mixture is subjected to one or more ligase detection reaction cycles having a denaturation treatment, and a hybridization treatment. The denaturation treatment involves separation of hybridized oligonucleotides from the tertiary extension products. In the hybridization treatment, the oligonucleotide probe sets hybridize at adjacent positions in a base-specific manner to their respective tertiary extension products, if present. As a result, adjacent probes ligate to one another to form a ligation product sequence containing the detectable reporter label and the tertiary extension product-specific portions connected together. The oligonucleotide probe sets may hybridize to nucleotide sequences other than their respective complementary tertiary extension products but do not ligate together due to a presence of one or more mismatches and individually separate during the denaturation treatment. Following the ligase detection reaction cycles, the reporter labels of the ligation product sequences are detected which indicates the presence of one or more low abundance target nucleotide sequences in the sample.

Figure 1B:
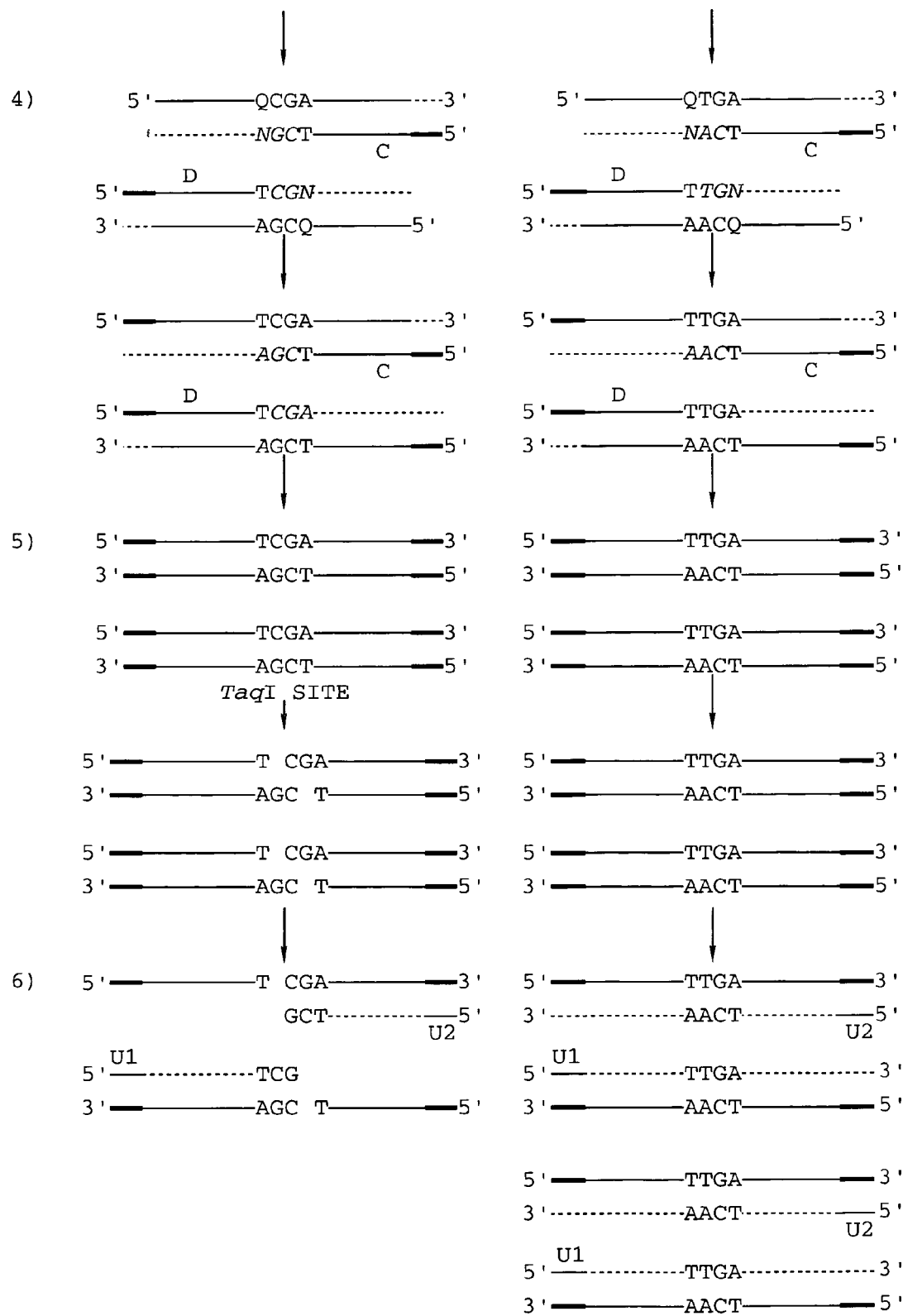
Figure 1C:
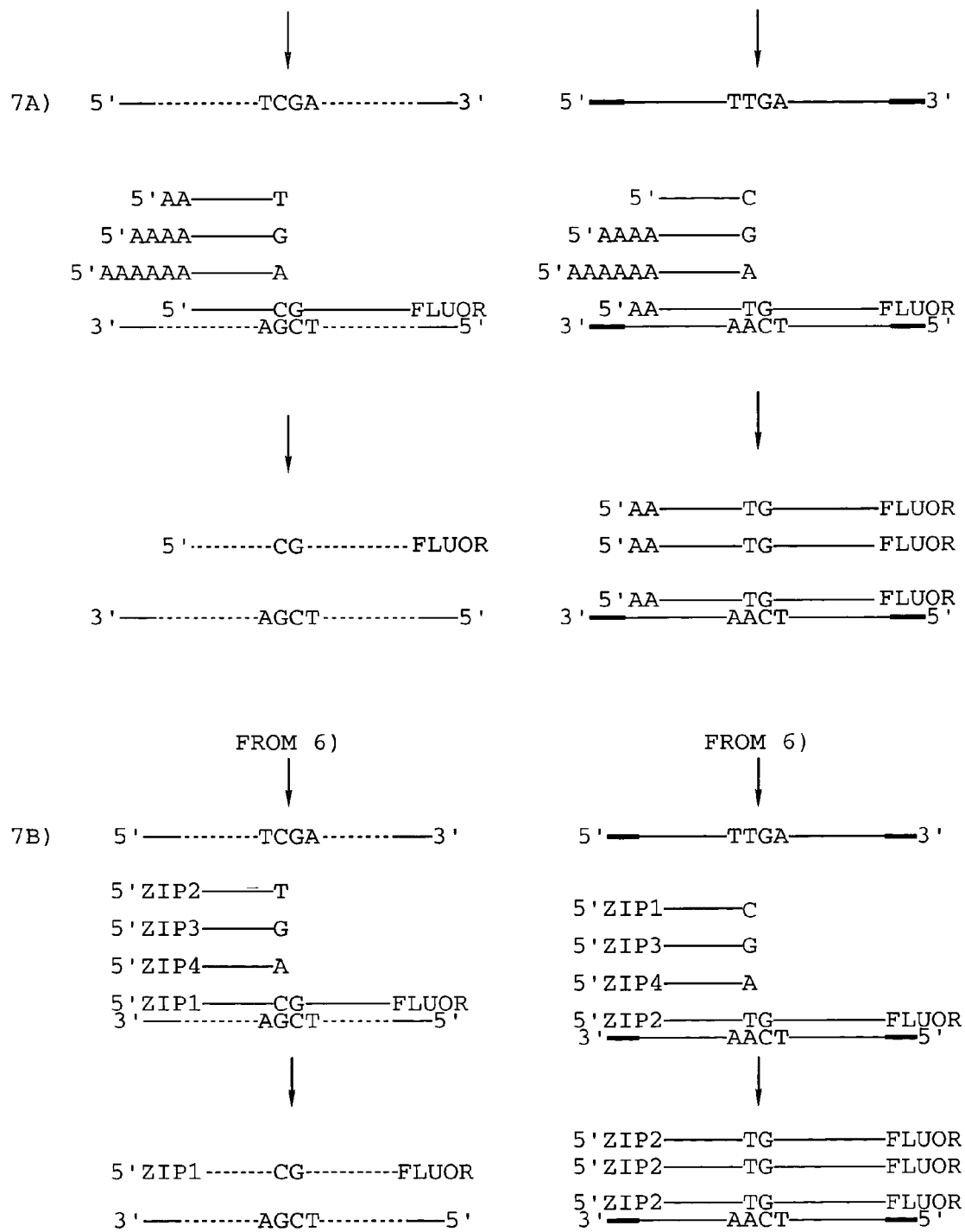

FIGS. 1A–C are a schematic diagram of the amplification and detection of mutant DNA by PCR/RE/LDR according to the method of the present invention. The process begins with a sample containing a normal, or wild-type sequence in high abundance, and, possibly, a mutant of that sequence, such as a cancer gene, in low abundance. Comparing the mutant and wild type sequences in FIGS. 1A–C, it is apparent that they differ with respect to only one base. In the wild-type sequence, the distinguishing base is a "C," while the mutant sequence has a "T" at the corresponding location.

First, the sample is subjected to a primary PCR step, which creates a modified target sequence. In the primary PCR procedure shown in Steps 1 and 2 of FIG. 1, wild-type and mutant DNA undergo denaturation at 94° C., to create single-stranded DNA templates. As shown in Step 1 of FIG.

1, primers A and B, each containing 3' terminal nucleotide analogue are annealed to the single stranded DNA templates. Facilitated by a polymerase, the analogue primers undergo an extension procedure as shown in Step 2 of FIG. 1. This process of denaturing double stranded nucleic acids, hybridizing primers to the resulting single stranded nucleic acids, and extending the primers is repeated, in accordance with conventional PCR procedures, to produce, in quantity, extension products in the form of modified target sequences containing the nucleotide analogue. The polymerase chain reaction process is fully described in H. Erlich, et al., "Recent Advances in the Polymerase Chain Reaction," *Science* 252: 1643–50 (1991); M. Innis, et al., *PCR Protocols: A Guide to Methods and Applications*, Academic Press: New York (1990); and R. Saiki, et al., "Primer-directed Enzymatic Amplification of DNA with a Thermostable DNA Polymerase," *Science* 239: 487–91 (1988), which are hereby incorporated by reference. Further details for use of PCR in accordance with the present invention are provided in the Examples below.

As shown in Step 1 of FIG. 1, the wild-type and mutant sequences have complementary X:W and Y:Z base pairs proximate to the distinguishing bases of these sequences. When these sequences are denatured in the primary PCR procedure, primers A and B are configured to hybridize to those sequences such that Q bonds to the Y and W bases. In subsequent cycles of the primary PCR step, polymerase encounters a Q analog in what is now a template strand. The polymerase can "read" the analog as one of several bases and it will "write" opposite the Q one of several different bases which in effect are "complementary" to the analog. Because different bases can be incorporated at such positions, the products are degenerate, ideally having G, A, T and C present in the same positions opposite Q analogs in the pool of products. These degenerate bases are indicated by "N." As shown in Step 2 of FIG. 1, the mismatch, formed in both the wild-type and mutant sequence, is signified as base "N".

Nucleotide analogs suitable for the present invention include, but are not limited to, the following: Q1, 1-(2'-deoxy-β-D-ribofuranosyl)imidazole-4-carboxamide; Q2, 1-(2'-deoxy-β-D-ribofuranosyl)-3-nitropyrrole; Q5, 2'-deoxyinosine; Q6, 6-(2'-deoxy-β-D-ribofuranosyl)-6H,8H-3,4-dihydropyrimido[4,5-c][1,2]oxazine-7-one; Q7, 2-amino-7-(2'-deoxy-β-D-ribofuranosyl)-6-methoxyaminopurine; Q16, 1-(2'-deoxy-β-D-ribofuranosyl)-4-iodopyrazole; Q18, 1-(2'-deoxy-β-D-ribofuranosyl)pyrrole-3-carboxamide; Q19, 1-(2'-deoxy-β-D-ribofuranosyl)-4-nitropyrazole.

Next, as shown in Step 3 of FIG. 1, a secondary PCR phase is carried out. The oligonucleotide primer set of the secondary PCR phase has a first oligonucleotide primer with a target-specific portion and a 5' upstream secondary primer-specific portion, and a second oligonucleotide primer with a target-specific portion and a 5' upstream secondary primer-specific portion. These are represented by primers "C" and "D" in Step 3 of FIG. 1. During the secondary PCR phase, the target specific portions of the secondary PCR primers will hybridize to complementary strands of the primary extension products. As shown in Step 3 of FIG. 1, these hybridized primers are then extended using polymerase to form secondary PCR extension products, as shown in Step 3 of FIG. 1. The secondary PCR phase is repeated for 2–20 PCR cycles, involving denaturation of double stranded nucleic acids, primer hybridization, and primer extension, until the primary PCR extension product is sufficiently amplified.

Due to the "T" v. "C" difference in the mutant sequence versus the wild-type sequence, respectively, as shown in FIGS. 1A–C, the secondary extension products can be treated with the appropriate restriction endonuclease (RE) that recognizes the RE site in the secondary extension products derived from the wild-type sequence. However, the secondary PCR extension product formed from the mutant nucleic acid sequence does not contain a restriction endonuclease site. In the embodiment of FIGS. 1A–C, the restriction endonuclease recognition site incorporated in the secondary extension products derived from the wild-type sequence is a TaqI recognition site, 5'—TCGA—3'. TaqI cleaves specifically within this recognition site, between the T and the C, in each strand of the double stranded DNA secondary extension product. However, other restriction endonuclease sites and their corresponding restriction endonucleases could instead be utilized.

Once the restriction site is incorporated into the high abundance target, the appropriate restriction endonuclease is added, under conditions that allow the digestion of the restriction site nucleotide sequence. Restriction endonucleases, derived from bacteria, are enzymes that cut DNA within a nucleotide chain. Each restriction endonuclease recognizes specific short oligonucleotides from four to eight residues long in a DNA sequence. Under appropriate conditions the RE cleaves the each strand at a phosphodiester bond within the recognition site. A restriction endonuclease cuts a pure DNA sample into consistently reproducible fragments that can easily be separated by gel electrophoresis. Several hundred restriction endonucleases have been identified and are commercially available. See Darnell et al., "Manipulating Macromolecules," *Molecular Cell Biology*, Second Edition, New York, N.Y.: W. H. Freeman and Company, pp. 189–225 (1990), which is hereby incorporated by reference. Any RE can be used in accordance with the method of the present invention. The choice of RE to be used is made based upon the information available for the DNA in the starting sample. The RE sites that occur within a gene are readily available through resources such as GenBank; the manufacturer, if the DNA has been obtained commercially, or will have been identified as part of the study of the gene, prior to the use of the method of the present invention. Primer design for the PCR phases of the invention is based upon the knowledge of the restriction sites in a gene. RE site identification can be readily determined by DNA mapping and DNA cloning. Watson et al., "In Vitro Mutagenesis," *Recombinant DNA*, Second Edition, New York, N.Y.: W. H. Freeman and Company, pp. 191–194 (1983), which is hereby incorporated by reference. Optimal conditions for complete cleavage by a restriction endonuclease are specific. Digestion should be carried out per manufacturer's recommendations for a particular RE, or as described in Sambrook et al., *Molecular Cloning: A Laboratory Manual*, Second Edition, Cold Spring Harbor Press, N.Y. (1989), which is hereby incorporated by reference.

After treatment of the secondary extension product with a restriction endonuclease, a tertiary PCR process is carried out. As shown in Step 6 of FIG. 1, this involves providing a tertiary oligonucleotide primer set having a first tertiary primer that is a universal primer (U1), containing the same sequence as the 5' upstream portion of the first oligonucleotide primer of the secondary oligonucleotide primer set, and a second tertiary primer containing the same sequence as the 5' upstream portion of a second oligonucleotide primer of the secondary oligonucleotide primer set. The set of tertiary oligonucleotide primers are used in amplifying the restriction endonuclease-digested secondary extension products. The secondary extension products are blended with the tertiary oligonucleotide primer set, and a polymerase to form a tertiary polymerase chain reaction mixture.

The tertiary polymerase chain reaction mixture is subjected to polymerase chain reaction conditions involving denaturation of double stranded nucleic acids, hybridization of tertiary oligonucleotide primers to the resulting single stranded nucleic acids, and extension of the hybridized primer. This procedure is repeated through a sufficient number of cycles involving these steps in order to produce an appropriate amount of tertiary PCR extension products. Since the secondary PCR extension products have been treated with a restriction endonuclease, the tertiary PCR extension products derived from the wild-type nucleic acid sequence are short as a result of their being cleaved proximate to the nucleotide corresponding to the distinguishing base. On the other hand, the tertiary PCR extension products derived from the mutant nucleic acid sequence are larger and not cleaved proximate to the nucleotide corresponding to the distinguishing base. See FIG. 1, Step 6. As a result, the tertiary extension products derived from the mutant nucleic acid sequence are readily distinguished from those derived from wild-type nucleic acid sequence in the subsequent LDR step.

A second restriction endonuclease digest may also be carried out following the tertiary PCR phase, to remove any high abundance targets that may have been amplified due to PCR error or incomplete digestion in the first RE step.

Following the tertiary PCR extension procedure, the resulting tertiary extension products are subjected to an LDR procedure according to either Step 7A or Step 7B of FIG. 1. In either of these alternatives, the LDR procedure begins by first denaturing the tertiary PCR extension products to produce single-stranded DNA (ssDNA). The discrimination probes are distinguished by having a different nucleotide on the 3' ends and a different number of adenine bases on their 5' ends. As a result, ligation products produced from each of the discrimination probes are identified by detection of the fluorescent label and distinguished from one another on a gel by their differing electrophoretic mobility.

In Step 7A of FIG. 1, the LDR probe set contains 4 alternative discrimination probes and a common probe, which can ligate to any of the four discrimination probes. The common probe contains a fluorescent tag on its 3' end. The tertiary extension products, these oligonucleotide probes, and a thermostable ligase are combined to form a ligase detection reaction mixture and subjected to a series of ligase detection reaction cycles.

The ligase detection reaction is described generally in WO 90/17239 to Barany et al., "Cloning, Overexpression and Nucleotide Sequence of a Thermostable DNA Ligase-encoding Gene," *Gene*, 109:1–11 (1991), and F. Barany, "Genetic Disease Detection and DNA Amplification Using Cloned Thermostable Ligase," *Proc. Natl. Acad. Sci. USA*, 88:189–193 (1991), and U.S. Pat. Nos. 5,494,810, 5,830,711 and 6,027,889 to Barany, the disclosures of which are hereby incorporated by reference. In accordance with the present invention, the ligase detection reaction can use 2 sets of complementary oligonucleotides. This is known as the ligase chain reaction, which is described in the immediately preceding references, which are hereby incorporated by reference. Alternatively, the ligase detection reaction can involve a single cycle that is known as the oligonucleotide ligation assay. See Landegren, et al., "A Ligase-Mediated Gene Detection Technique," *Science* 241:1077–80 (1988); Landegren, et al., "DNA Diagnostics—Molecular Techniques and Automation," *Science* 242:229–37 (1988); and U.S. Pat. No. 4,988,617 to Landegren, et al., which are hereby incorporated by reference.

During ligase detection reaction phases, the denaturation treatment is carried out at a temperature of 80–105° C., while hybridization takes place at 50–85° C. Each cycle comprises a denaturation treatment and a thermal hybridization treatment which in total is from about one to five minutes long. Typically, the ligation detection reaction involves repeatedly denaturing and hybridizing for 2 to 50 cycles. The total time for the ligase detection reaction phase is 1 to 250 minutes.

The preferred thermostable ligase is that derived from *Thermus aquaticus*. This enzyme can be isolated from that organism. M. Takahashi, et al., "Thermophilic DNA Ligase," *J. Biol. Chem.* 259:10041–47 (1984), which is hereby incorporated by reference. Alternatively, it can be prepared recombinantly. Procedures for such isolation as well as the recombinant production of *Thermus aquaticus* ligase (as well as *Thermus themophilus* ligase) are disclosed in WO 90/17239 to Barany, et al., F. Barany, et al., "Cloning, Overexpression and Nucleotide Sequence of a Thermostable DNA-Ligase Encoding Gene," *Gene* 109:1–11 (1991), and U.S. Pat. Nos. 5,494,810 and 5,830,711 to Barany, which are hereby incorporated by reference. These references contain complete sequence information for this ligase as well as the encoding DNA. Other suitable ligases include *E. coli* ligase, T4 ligase, and *Pyrococcus* ligase.

The ligation detection reaction mixture may include a carrier DNA, such as salmon sperm DNA.

The hybridization step in the ligase detection reaction, which is preferably a thermal hybridization treatment, discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected.

The oligonucleotide probe sets, as noted above, may have a reporter label suitable for detection. Useful labels include chromophores, fluorescent moieties, enzymes, antigens, heavy metals, magnetic probes, dyes, phosphorescent groups, radioactive materials, chemiluminescent moieties, and electrochemical detecting moieties. Also appropriate would be the use of molecular weight tags for discrimination by mass spectroscopy, such as a matrix assisted laser desorption ionization—time of flight mass spectroscopy (MALDI-TOF) array system.

The oligonucleotide probe sets can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, and mixtures thereof.

The oligonucleotides of the oligonucleotide probe sets each have a hybridization or melting temperature (i.e. $T_m$) of 66–70° C. These oligonucleotides are 20–28 nucleotides long.

As shown in Step 7A of FIG. 1, the ligation products derived from the mutant nucleic acid sequence are formed from the discrimination probe having 2 adenine bases on its 5' end. The other discrimination probes will not be ligated to the common probe as a result of the mutant nucleic acid sequence being present.

On the other hand, for the most part, no ligation products using the above-described probe sets, will be formed from the wild-type sequence. This occurs because the endonuclease digestion causes tertiary extension products derived from the wild-type nucleic acid sequence to be cleaved, and, as a result, both the common and discrimination probes of that probe set will not hybridize to such tertiary extension product in a manner permitting them to be ligated together. However, to the extent the endonuclease digestion of the secondary extension products derived from the wild-type sequence is incomplete, a small residual amount of uncleaved tertiary extension product derived from the wild-type sequence may be present in the ligase detection reaction mixture. This will cause ligation products to be produced from the discrimination probe having no adenines at its 5' end.

Figure 2:
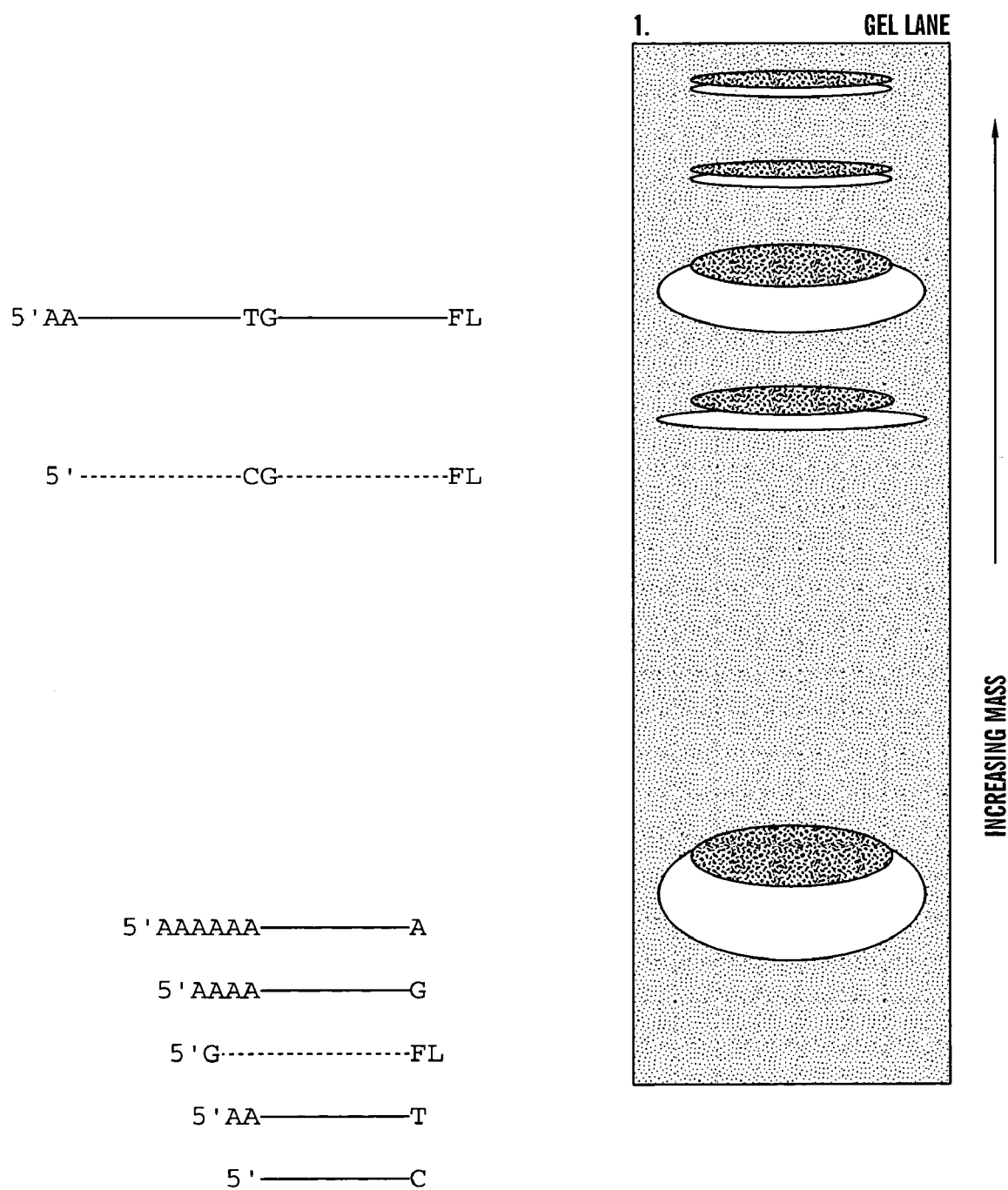
FIG. 2 shows the detection of ligation products resulting from the process of FIGS. 1A–C, using gel electrophoresis.

FIG. 2 shows the gel electrophoresis detection of products formed from the ligase detection reaction procedure of FIG. 1, Step 7A. As shown in FIG. 2, unligated probes have great electrophoretic mobility and form a band at the bottom of the gel. Ligation products derived from any small amount of tertiary extension products derived from the wild-type sequence have the next greatest electrophoretic mobility and form a band at an intermediate location on the gel. Ligation products derived from the mutant sequence have less electrophoretic mobility than the wild-type ligation products, and form a thick band slightly above that of the wild-type ligation products. If no mutant sequence is present in the sample, no such gel band will be formed. The top two bands are trace ligation products with low electrophoretic mobility. These high molecular weight bands are artifacts, presumably arising from polymerase error and template decomposition during PCR. The composition of the PCR buffer can strongly affect the fraction of these PCR error products present in the sample after amplification.

The use of capillary and gel electrophoresis to detect DNA products based on differences in their electrophoretic mobility is well known. See e.g., Grossman, et al., "High-density Multiplex Detection of Nucleic Acid Sequences: Oligonucleotide Ligation Assay and Sequence-coded Separation," *Nucl. Acids Res.* 22(21): 4527–34 (1994), which is hereby incorporated by reference.

As an alternative to the ligase detection reaction procedure shown in FIG. 1, Step 7B, the discrimination probes can be provided with different address-specific portions (i.e. ZIP1, ZIP2, ZIP3, and ZIP4) at their 5' ends. This enables the ligation products to be detected on an addressable array having different capture oligonucleotide probes which are complementary to the address-specific portions on the discrimination probes. As a result, each ligation product is directed to a different address of a DNA microarray during a hybridization procedure subsequent to the ligase detection reaction phase. The hybridized ligation products all have the same label but are distinguished from one another by the location on which the ligation products are immobilized. Alternatively, different labels can be on the discrimination base, while the address-specific portion is on the common probe. In this embodiment, different ligation products will be immobilized on the array at locations with the same capture probe; however, the different ligation products will be distinguished by different labels.

Figure 3:
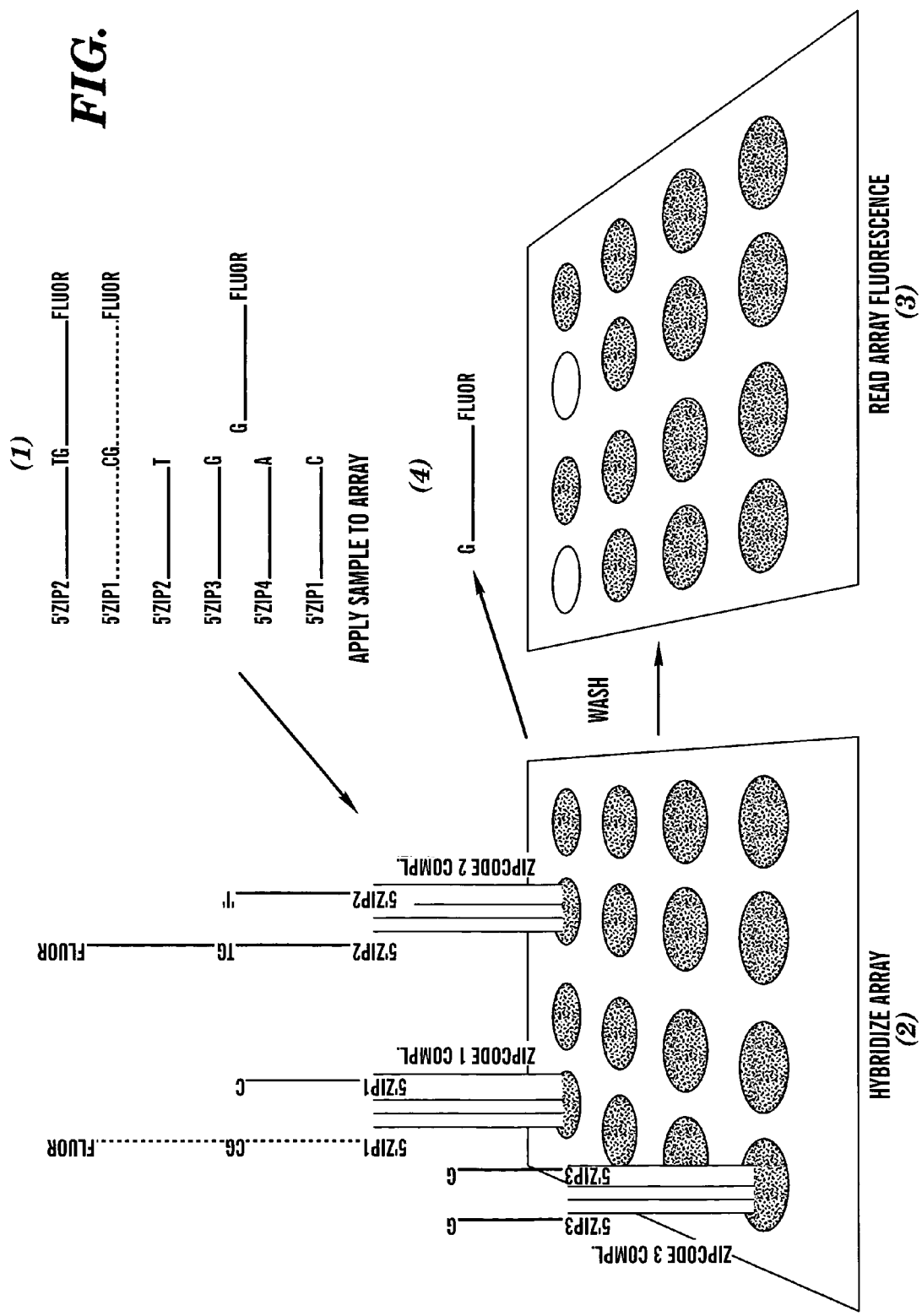
FIG. 3 shows the detection of ligation products resulting from the process of FIGS. 1A–C using an addressable array.

FIG. 3 shows the detection of ligation products resulting from the process of FIG. 1, Step 7B using an addressable array. In this case, as shown in FIG. 1, Step 7B, the common probe has a label and the discrimination probes have the address-specific portion. In FIG. 3, the ligation products are caused to contact the addressable array under conditions effective to permit address-specific portions of the ligation products to hybridize to capture oligonucleotides on the array. As shown in FIG. 3, Steps 2 and 3, discrimination probes (e.g., probes having address-specific portions ZIP4 (not shown) and ZIP3 (shown)) which do not form ligation products are immobilized on the array but are not detected due to the absence of a label. Unligated common probes do not hybridize to the array and are subsequently washed away (e.g., at 65° C.–80° C. and low salt) so they produce no signal. Any small amount of ligation products derived from the wild-type nucleic acid sequence (due to incomplete upstream endonuclease digestion) are immobilized (together with any of the corresponding unligated discrimination probe) at the capture oligonucleotide complementary to address-specific portion ZIP1. Similarly, any ligation products derived from the mutant sequence are immobilized (together with any of the corresponding unligated probe) at the capture oligonucleotide complementary to address-specific portion ZIP2. The presence of mutant sequence and/or wild-type sequence is detected in this embodiment by the existence of a fluorescent signal at respective different locations on the array. Heterozygosity is indicated by equal signals at the capture oligonucleotides complementary to address-specific portions ZIP1 and ZIP2. The signals may be quantified using a fluorescent imager. This format uses a unique address for each allele and may be preferred for achieving very accurate detection of low levels of signal (30 to 100 attomoles of LDR product).

The use of a solid support with an array of capture oligonucleotides is fully disclosed in pending provisional U.S. Patent Application Ser. No. 60/011,359, which is hereby incorporated by reference. This method involves providing a solid support having an array of positions each suitable for attachment of an oligonucleotide. A linker or support (preferably non-hydrolyzable), suitable for coupling an oligonucleotide to the solid support at each of the array positions, is attached to the solid support. An array of oligonucleotides on a solid support is formed by a series of cycles of activating selected array positions for attachment of either single or a multiple nucleotides at the activated array positions.

When using such arrays, the oligonucleotide probes used in the above-described coupled PCR and LDR phases, respectively, have an addressable array-specific portion. After the PCR and LDR phases are completed, the addressable array-specific portions for the products of such processes remain single stranded and are caused to hybridize to the capture oligonucleotides during a capture phase. C. Newton, et al., "The Production of PCR Products With 5' Single-Stranded Tails Using Primers That Incorporate Novel Phosphoramidite Intermediates," *Nucl. Acids Res.* 21(5): 1155–62 (1993), which is hereby incorporated by reference.

During the capture phase of the process, the mixture is contacted with the solid support at a temperature of 45–90° C. and for a time period of up to 60 minutes. Adding cations, volume exclusion or chaotropic agents may accelerate hybridizations. When an array consists of dozens to hundreds of addresses, it is important that the correct ligation product sequences have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array is washed sequentially with a low stringency wash buffer and then a high stringency wash buffer.

It is important to select capture oligonucleotides and addressable nucleotide sequences which will hybridize in a stable fashion. This requires that the oligonucleotide sets and the capture oligonucleotides be configured so that the oligonucleotide sets hybridize to the target nucleotide sequences at a temperature less than that which the capture oligonucleotides hybridize to the addressable array-specific portions. Unless the oligonucleotides are designed in this fashion, false positive signals may result due to capture of adjacent unreacted oligonucleotides from the same oligonucleotide set which are hybridized to the target.

The capture oligonucleotides can be in the form of ribonucleotides, deoxyribonucleotides, modified ribonucleotides, modified deoxyribonucleotides, peptide nucleotide analogues, modified peptide nucleotide analogues, modified phosphate-sugar backbone oligonucleotides, nucleotide analogues, and mixtures thereof.

It may be desirable to destroy chemically or enzymatically unconverted all unligated LDR oligonucleotide probes that contain addressable nucleotide array-specific portions prior to capture of the ligation products on a DNA array. Such unconverted probes will otherwise compete with ligation products for binding at the addresses on the array of the solid support which contain complementary sequences. Destruction can be accomplished by utilizing an exonuclease, such as exonuclease III (L-H Guo and R. Wu, *Methods in Enzymology* 100:60–96 (1985), which is hereby incorporated by reference) in combination with LDR probes that are blocked at the ends and not involved with ligation of probes to one another. The blocking moiety could be a reporter group or a phosphorothioate group. T. T. Nikiforow, et al., "The Use of Phosphorothioate Primers and Exonuclease Hydrolysis for the Preparation of Single-stranded PCR Products and their Detection by Solid-phase Hybridization," *PCR Methods and Applications*, 3:p. 285–291 (1994), which is hereby incorporated by reference. After the LDR process, unligated probes are selectively destroyed by incubation of the reaction mixture with the exonuclease. The ligated probes are protected due to the elimination of free 3' ends which are required for initiation of the exonuclease reaction. This approach results in an increase in the signal-to-noise ratio, especially where the LDR reaction forms only a small amount of product. Since unligated oligonucleotides compete for capture by the capture oligonucleotide, such competition with the ligated oligonucleotides lowers the signal. An additional advantage of this approach is that unhybridized label-containing sequences are degraded and, therefore, are less able to cause a target-independent background signal, because they can be removed more easily from the DNA array by washing.

A wide variety of infectious diseases can be detected by the method of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia, B-Hemolytic strep., Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia,* and *Actinomycetes.*

Fungal infectious agents, which can be detected by the present invention, include *Cryptococcus neoformans, Blastomyces dermatitidis, Histoplasma capsulatum, Coccidioides immitis, Paracoccidioides brasiliensis, Candida albicans, Aspergillus fumigatus, Phycomycetes (Rhizopus), Sporothrix schenckii, Chromomycosis,* and *Maduromycosis.*

Viral infectious agents, which can be detected by the present invention, include human immunodeficiency virus, human T-cell lymphocytotrophic virus, hepatitis viruses (e.g., Hepatitis B virus and Hepatitis C virus), Epstein-Barr virus, cytomegalovirus, human papillomaviruses, orthomyxo viruses, paramyxo viruses, adenoviruses, corona viruses, rhabdo viruses, polioviruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichomonas* spp., *Balantidium coli, Wuchereria bancrofti, Toxoplasma* spp., *Enterobius vermicularis, Ascaris lumbricoides, Trichuris trichiura, Dracunculus medinesis, trematodes, Diphyllobothrium latum, Taenia* spp., *Pneumocystis carinii,* and *Necator americanus.*

The present invention is also useful for detection of drug resistance by infectious agents. For example, vancomycin-resistant *Enterococcus faecium,* methicillin-resistant *Staphylococcus aureus,* penicillin-resistant *Streptococcus pneumoniae,* multi-drug resistant *Mycobacterium tuberculosis,* and AZT-resistant human immunodeficiency virus can all be identified with the present invention.

Genetic diseases can also be detected by the method of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Kinefelter Syndrome, Huntington Disease, autoimmune diseases, lipidosis, obesity defects, hemophilia, inborn errors of metabolism, and diabetes.

Cancers that can be detected by the method of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/Ab1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

The present invention is useful in detecting the presence of one or more of a low abundance sequence, that differs from a high abundance sequence by one or more single-base changes, insertions, deletions, or translocations when the low abundance sequence is present in the same sample in less than a 1:1,000 molar ratio, preferably, in less than a 1:10,000 molar ratio, and, most preferably, in less than a 1:100,000 molar ratio, to the amount of the high abundance sequence.

Another aspect of the present invention is its capability to quantify the amount of target nucleotide sequence in a sample. This can be achieved by establishing an internal standard (i.e. where the standard establishing material is amplified and detected with the sample).

For quantification using an internal standard, a known amount of one or more marker target nucleotide sequences is added to the sample. In addition, a plurality of marker-specific oligonucleotide probe sets are added along with the ligase, the previously discussed oligonucleotide probe sets, and the tertiary extension products to a mixture. The marker-specific oligonucleotide probe sets have (1) a first oligonucleotide probe with a target-specific portion complementary to the marker target nucleotide sequence, and (2) a second oligonucleotide probe with a target-specific portion complementary to the marker target nucleotide sequence and a detectable reporter label. The oligonucleotide probes in a particular marker-specific oligonucleotide set are suitable for ligation together when hybridized adjacent to one another on a corresponding marker target nucleotide sequence. However, there is a mismatch which interferes with such ligation when hybridized to any other nucleotide sequence present in the sample or added marker sequences. The presence of ligation product sequences is identified by detection of reporter labels. The amount of target nucleotide sequences in the sample is then determined by comparing the amount of ligation product sequence generated from known amounts of marker target nucleotide sequences with the amount of other ligation product sequences.

The present invention also relates to a kit for identifying one or more low abundance sequences differing by one or more single-base changes, insertions, or deletions, from a high abundance sequence in a plurality of target nucleotide sequences. This kit provides a primary oligonucleotide primer set, a secondary oligonucleotide primer set, a tertiary oligonucleotide primer set, and a plurality of oligonucleotide probe sets.

The primary oligonucleotide primer set provided in the kit has (a) a first oligonucleotide primer containing a target-specific portion, and (b) a second oligonucleotide primer containing a target-specific portion. The primary oligonucleotide primers are suitable for hybridization on complementary strands of a corresponding high and low abundance target nucleotide sequences to permit formation of a primary extension product. However, the primers have a mismatch which interferes with formation of such a polymerase chain reaction product when hybridized to any other nucleotide sequence present in the sample.

The secondary oligonucleotide primer set provided in the kit has (a) a first oligonucleotide primer, containing a target-specific portion and a 5' upstream secondary primer-specific portion, and (b) a second oligonucleotide primer, containing a target-specific portion and a 5' upstream secondary primer-specific portion. The secondary oligonucleotide primers are suitable for hybridization on complementary strands of the primary extension products to permit formation of a secondary extension product which contains or creates a restriction endonuclease recognition site when amplifying the high abundance target, but does not contain or create a restriction endonuclease recognition site when amplifying the one or more low abundance targets.

The tertiary oligonucleotide primer set provided in the kit have (a) a first tertiary primer containing the same sequence as the 5' upstream portion of the first oligonucleotide primer of the secondary oligonucleotide primer set, and (b) a second tertiary primer containing the same sequence as the 5' upstream portion of a second oligonucleotide primer of the secondary oligonucleotide primer set. The set of tertiary oligonucleotide primers may be used to amplify all of the secondary extension products.

The kit also provides a plurality of oligonucleotide probe sets. Each set has (a) a first oligonucleotide probe, containing a tertiary extension product-specific portion and a detectable reporter label, and (b) a second oligonucleotide probe, containing a tertiary extension product-specific portion. The oligonucleotide probes in a particular set are suitable for ligation together when hybridized adjacent to one another on a complementary tertiary extension product-specific portion. However, the probes have a mismatch which interferes with such ligation when hybridized to any other nucleotide sequence present in the sample.

The kit may also contain a polymerase, an endonuclease restriction enzyme, and/or a ligase, as described above.

EXAMPLES

Optimizing Analog Additions under PCR Conditions

Example 1

Oligonucleotide Synthesis for Analog Efficiency

Oligonucleotides were synthesized at the 0.2 $\mu$mole scale by cyanoethyl phosphoramidite chemistry on an Applied Biosystems 394 DNA synthesizer. Standard 500 Å CPG columns and reagents (Applied Biosystems) were used with the following exceptions: oligonucleotides 50 bases in length were synthesized using wide-pore 1000 Å CPG columns (Applied Biosystems); oligonucleotides with fluorescent dye FAM at the 5' terminus were synthesized using FAM phosphoramidite (Applied Biosystems) with a 15 minute coupling step; oligonucleotides with 5' phosphate were synthesized using phosphorylation reagent (Glen Research), with a 15 minute coupling step; oligonucleotides with 3' blocking group were synthesized using Y-Spacer CPG columns (Glen Research). Oligonucleotides with the 3' nucleotide analogs 2'-deoxyinosine $Q_5$), 6-(2'-deoxy-β-D-ribofuranosyl)-6H, 8H-3,4-dihydropyrimido[4,5-c][1,2]oxazine-7-one ($Q_6$), and 2-amino-7-(2'-deoxy-β-D-ribofuranosyl)-6-methoxyaminopurine $Q_7$) were synthesized using 2'-deoxyinosine-CPG, dP-CPG and dK-CPG, respectively (Glen Research), as shown in FIG. 5. The oligonucleotide primers containing $Q_1$, $Q_2$ and $Q_{18}$ at the Y-position were synthesized from $Q_1$, $Q_2$, and $Q_{18}$ derived-CPG synthesized from $Q_1$ (Johnson et al., "The Synthesis and Stability of Oligodeoxyribonucleotides Containing the Deoxyadenosine Mimic 1-(2'-Deoxy-Beta-D-Ribofuranosyl)Imidazole-4-Carboxamide," *Nucleic Acid Res.*, 25:559–67 (1997)), $Q_2$ (Bergstrom et al., *Journal of the American Chemical Society*, 117:1201–9 (1995)) and $Q_{18}$ (Zhang et al., "Exploratory Studies on Azole Carboxamides as Nucleobase Analogs: Thermal Denaturation Studies on Oligodeoxyribonucleotide Duplexes Containing Pyrrole-3-Carboxamide," *Nucleic Acids Res.*, 26:2208–15 (1998)) by the method of Pon et al. (Pon et al., "Derivatization of Controlled Pore Glass Beads for Solid Phase Oligonucleotide Synthesis," *BioTechniques*, 6:768–75 (1988)).

Example 2

PCR Polymerases and Buffers

The DNA polymerases used were AmpliTaq, AmpliTaq—Stoeffel Fragment, AmpliTaq—Fluorescent Sequencing (Applied Biosystems), Vent and Vent(exo⁻) (New England Biolabs), and Expand polymerase mix (Taq and Pfu polymerase mixture, in Expand High Fidelity kit, Boehringer Mannheim). The commercially available PCR buffers used were supplied in the AmpliTaq and Expand High Fidelity kits. An alternative buffer CiNF, buffer G(f), is described elsewhere (Day et al., *Nucleic Acids Res*, (1999)). Briefly, CiNF reactions contain 20 mM citrate pH 7.6, 200 μg/ml bovine serum albumin, 2.5 mM MgCl2, 200 μM dNTP (each) and either 16 mM $(NH_4)_2SO_4$, or 50 mM potassium acetate, 10% formamide, primers, and template DNA. All PCR and LDR reactions described below were performed under paraffin oil.

Example 3

Mismatch Extension Efficiency

Primers containing natural bases and nucleotide analogs were used in PCR to compare and measure the efficiency of product formation from synthetic duplex p53 exon 7 templates having MspI (CCGG), TaqI (TCGA), HhaI (GCGC), or TaiI (ACGT) sites at the MspI position containing codon 248. The primers hybridized to wild-type sequence on either side of the MspI site with the 3' ends of the primers extending one base into the site on each side, see FIG. 6A. Eight different analogs and the four natural bases were tested in parallel reactions on each of the four synthetic templates. PCR was performed using Stoeffel Taq or Taq-Fluorescent Sequencing polymerases with the buffer supplied by manufacturer for each polymerase. 10 pmol of each primer and 20 fmol of duplex template were used, and 0.2 mM each dNTP and 4 mM $MgCl_2$. Parallel reactions underwent 10, 20, 30, 40, and 50 PCR cycles of 94° C. for 15 sec, 65° C. for 1 min. Efficiency and yield were determined from samples run on 6% agarose gels and stained with ethidium bromide.

Example 4

Mismatch Conversion Product Sequencing

Products most efficiently amplified by each analog were diluted 1000-fold in water. The diluted DNA products were reamplified for 20 cycles of 94° C. for 15 sec, 65° C. for 2 min. using the same polymerase and buffer as in the previous PCR, but with the addition of 10 pmol of "zipcode" containing primers p53zip248 (SEQ. ID. No. 5) and p53zip248R (SEQ. ID. No. 6), shown in FIG. 6A. Zipcode sequences are oligonucleotides with no known sequence similarity to DNA sequences in any organism. Amplification with zipcode primers is intended to specifically amplify the zipcode containing products of the previous PCR; i.e., only converted DNA (containing zipcodes) and not the nearly identical unconverted DNA (lacking zipcodes) will be amplified. Conversion products were run on 8% agarose gels and bands of the expected size excised. DNA was extracted from the gel slices by centrifugation in a 235C microcentrifuge (Fisher) for 30 min through 0.45 μm HVLP filter (Millipore). The conversion product was dried and resuspended in ABI Dye Terminator Cycle Sequencing reaction mix with one of the zipcode primers according to kit instructions (Applied Biosystems). An equal volume (3 μl each) of sequencing reaction was combined with dye mix consisting of 83% formamide (Eastman), 4 mM EDTA and 8 mg/ml Blue Dextran (Sigma). Samples were electrophoresed on a 7M urea, 10% acrylamide gel (19:1 bis, 0.6×TBE in gel and running buffer) in an ABI 373 DNA Sequencer. Data were analyzed using ABI 373A DNA Sequencer Data Analysis software version 1.2.0.

Example 5

Conversion Product Identification, with and without a Preconversion Step

Conversion fidelity was tested using nine different synthetic templates, with and without preconversion using three primers containing $Q_5$, $Q_6$, and $Q_7$ (see Example 1). Preconversion PCR was performed with 3' analog primers prior to adding the desired natural base primers, in an effort to avoid mismatch primer extension. The 50-basepair duplex DNA templates contained the wild-type p53 sequence surrounding codon 248, shown in FIG. 6B, except for the bases corresponding to the MspI site (CCGG). The following sequences were substituted at the MspI position: 1) CCGG (wild-type, SEQ. ID. No. 2), 2) CTGG (SEQ. ID. No. 17), 3) CGGG (SEQ. ID. No. 18), 4) CAGG (SEQ. ID. No. 19), 5) TCGA (SEQ. ID. No. 20), 6) GCGC (SEQ. ID. No. 21), 7) ACGT (SEQ. ID. No. 22), 8) CAGT (SEQ. ID. No. 23), and 9) GCGC (SEQ. ID. No. 24). A pre-secondary PCR reaction ("preconversion") was performed with hot start using 50 finol/μl p53-248$Q_N$ (SEQ. ID. No. 3) and p53-248$Q_N$R (SEQ. ID. No. 4) primers, and Vent (exo-) in CiNF buffer, buffer G(f), and 10 fmol/μl of duplex template. Preconversion used 2 PCR cycles of 94° C. 15 sec, 55° C. 1 min, 60° C. 1 min. Product was stored at 4° C. Conversion reactions were started with 1 μl of preconversion reaction containing the same polymerase and buffer, but no additional template. Each reaction required 10 pmol of each primer, using one of the four pairs p53zip248N and p53zip248NR (N=C, SEQ. ID. No. 25; T, SEQ. ID. No. 9; G, SEQ. ID. No. 26; or A, SEQ. ID. No. 27). Parallel conversion reactions with no preconversion were initiated with a hot start by adding 10 fmol of synthetic duplex template instead of preconversion reaction aliquot. PCR cycles were as follows: 5 cycles of 94° C. 15 sec, 55° C.+1° per cycle 1 min, 60° C. 1 min; then 20 cycles of 94° C. 15 sec, and 60° C. 2 min. A final extension was performed at 60° C. for 5 min. Polymerase was inactivated by freezing and thawing twice. Products were diluted 10× in water and reamplified by adding 1 μl to 20 μl of Expand polymerase and buffer mix. PCR was performed for 20 cycles (30 cycles for low yield reactions) of 94° C. 15 sec, 65° C. 2 min using 12 pmol of zipcode primers Ztop (SEQ. ID. No. 7) and Zbot (SEQ. ID. No. 8) (FIG. 6). LDR was performed as described below to identify the conversion products generated.

Example 6

Ligase Detection Reaction

Ligase detection reactions were performed in standard LDR buffer (25 mM Tris pH 7.6, 12 mM MgCl$_2$, 65 µg/ml bovine serum albumin, 100 mM KCl, and 10 mM DTT). Each 20 µl reaction contained approximately 500 fmol of dsDNA (1 µl of sample), 500 fmol of each discriminating probe (SEQ. ID. Nos. 11–14), and 750 fmol of common probe (SEQ. ID. No. 15), as shown in FIG. 6C. Sets of discriminating and common probes were synthesized to perform LDR on the expected conversion products and varied at the bases (B$_t$) corresponding to the MspI position sense strand (B$_1$B$_2$B$_3$B$_4$=CCGG for wild-type). The discrimination probes had wild-type sequence and terminate in -B$_1$B$_2$(-OH 3'). The discrimination probes were synthesized as a set of four probes each with C, T, G and A in turn at B$_2$. The common LDR probes had (5'PO$_4$-)B$_3$B$_4$- followed by wild-type sequence, and hybridized to the template with its 5' base adjacent to the 3' base of a discrimination probe. Discrimination probes varied the 3' terminal base to identify error products at B$_2$ of the MspI position. For simplicity, only B$_2$ was monitored. LDR probes matched the expected conversion products; for example, conversion of -CCGG- template to -ACGT- required discrimination probes ending in -AC, -AT, -AG, and -AA, and a common probe with 5' pGT-. Discrimination probes had 5' tails of different length and a FAM label for fluorescence detection. The tail length allowed physical separation of different LDR products on an acrylamide gel, and thus identification of the LDR products.

LDR reactions were preincubated for 1.5 min at 94° C. prior to the addition of 5 nmol Tth ligase, followed by 10 LDR cycles of 94° C. 15 sec, 65° C. 2 min, and a final hold briefly at 94° C. Reactions were cold quenched and stored at −70° C. The LDR products were separated on 10% acrylamide gels containing 7M urea, with 0.6×TBE (1×TBE: 90 mM Tris base, 90 mM Borate, 2 mM EDTA) in the gel and running buffer. Data were collected using an ABI 373 DNA sequencer with Genescan 672 software.

Example 7

Image Processing

Gel pictures were produced by the ABI 672 Analysis software. Dye specific images were opened in Adobe Photoshop 3.0, cropped, resized, and converted to grayscale. The grayscale images were opened in NIH Image 1.59, inverted, and 1D vertical background was subtracted. The background-subtracted images were reinverted and rendered in pseudocolor by Photoshop to make intensity differences easier to compare. Except for color replacement, only linear image processing was performed to preserve relative intensities.

Initial experiments were designed to determine the efficiency of generating PCR products when using probes containing 3' terminal nucleotide analogs (see above Examples). Eight different analogs were designed to pair with more than one of the four natural bases in order to convert one base to another base at a specific position in a sequence. Primer pairs containing either a nucleotide analog or one of the four natural bases at their 3' ends were used to amplify four different templates (FIG. 6A). Each nucleotide analog and natural base was mispaired (or paired) in turn with all four natural bases on the opposite strand, and amplification was attempted with either Taq Stoeffel Fragment or Taq Fluorescent Sequencing polymerases. The relative amplification efficiency was determined by the number of cycles required to generate visible product on an ethidium bromide stained agarose gel, as shown in Table 1. The 50-base pair synthetic duplex DNA templates containing p53 sequence spanning codon 248 are distinguished by the four bases replacing the MspI site, which are shown.

TABLE 1

| primer | TCGA template reads A | | CCGG template reads G | | GCGC template reads C | | ACGT template reads T | |
|---|---|---|---|---|---|---|---|---|
| 3' base | write | (eff.) | write | (eff.) | write | (eff.) | write | (eff.) |
| T | A | (+++) | A | (++) |  | (++) |  | (++) |
| C |  | (++) | G | (+++) |  | (++) |  | (++) |
| G |  | (++) |  | (++) | C | (+++) |  | (+++) |
| A |  | (+) |  | (+) | T | (+++) | T | (+++) |
| Q$_1$ | A,T | (±) |  | (±)$^1$ |  | (−) |  | (+++)$^1$ |
| Q$_2$ |  | (±)$^1$ |  | (±)$^1$ |  | (−) | T | (++)$^1$ |
| Q$_5$ |  | (++) |  | (++) |  | (+++) | C | (+++) |
| Q$_6$ | A,G | (+++) |  | (+++) |  | (++) |  | (++) |
| Q$_7$ |  | (+) |  | (+) |  | (+++) | T | (+++) |
| Q$_{16}$ | A,T | (+)$^1$ |  | (−) |  | (−) |  | (−) |
| Q$_{18}$ |  | (+)$^1$ |  | (±)$^1$ |  | (±)$^1$ | T,A | (+++) |
| Q$_{19}$ | A | (++)$^1$ |  | (−) |  | (±)$^1$ |  | (±)$^1$ |

$^1$Low product yield.
Table 1. Extension efficiency and conversion with 3' natural base and nucleotide analog primers. Four different templates were used to test primer extension from a 3' base or analog paired in turn with A, G, C and T. Relative efficiency was determined by the number of cycles required to generate visible product with Taq Stoeffel Fragment polymerase: 10 cycles, (++) 20 cycles, (+) 30 cycles, (±) 40 to 50 cycles, (−) no product. Two of the natural base mismatchprimer products were sequenced. Generally, the most efficiently amplified template for each analog was reamplified with truncated primers and sequenced to determine which bases are written opposite each analog. In one case (Q$_1$) a lower efficiency extension product with higher yield was selected for sequencing. Mixed base writing preference for some analogs is indicated, with most frequent product listed first.

Figure 4:
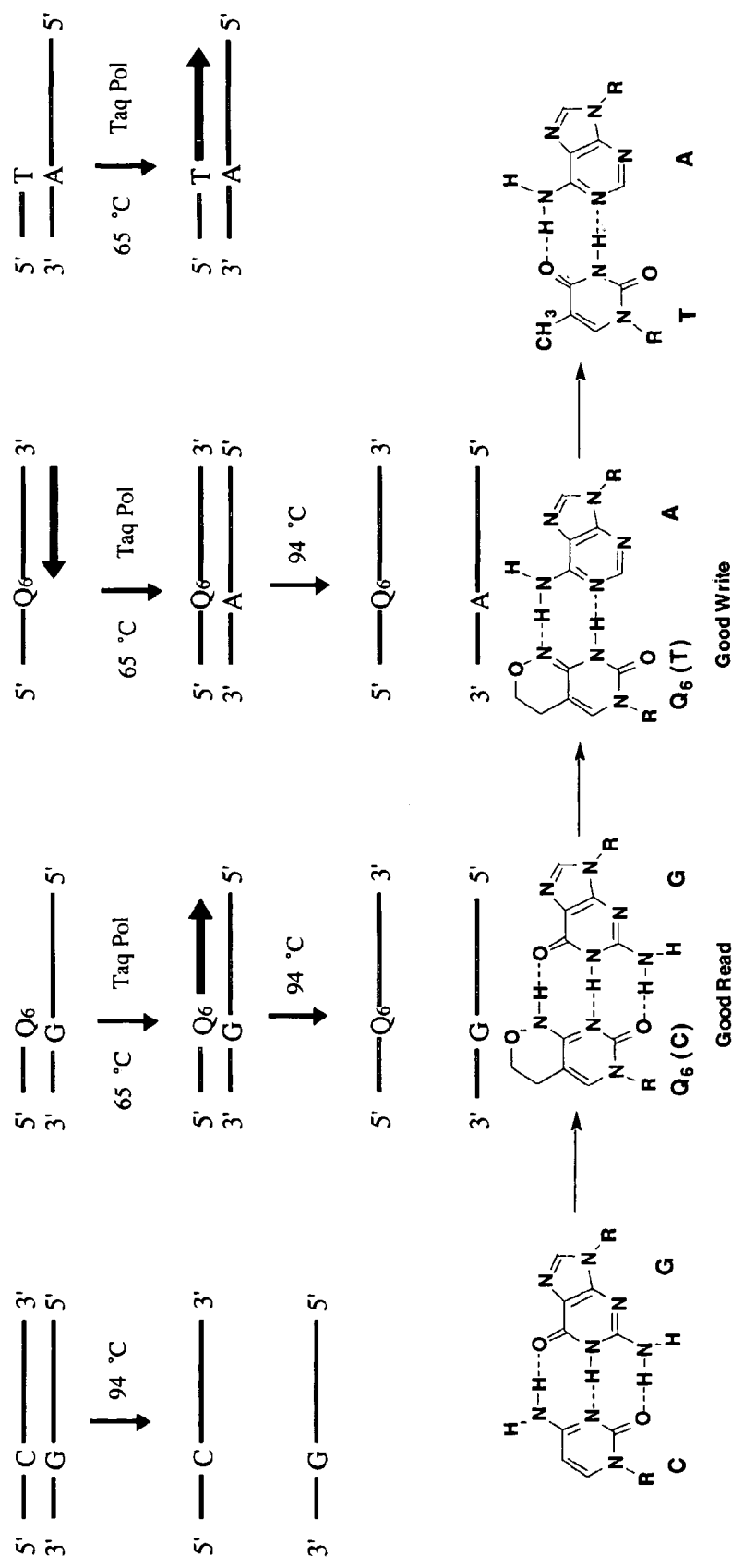
FIG. 4 shows a conversion facilitated by nucleotide analog preconversion. A C:G base pair in a sequence is targeted for conversion to a T:A basepair. Rather than using a 3' natural base mismatch primer to attempt direct conversion, a nucleotide analog ($Q_6$) primer is used for preconversion. The $Q_6$ analog reads the G base well and allows polymerase to efficiently extend from the 3' $Q_6$ primer.

Both Taq Stoeffel Fragment and Taq Fluorescent Sequencing polymerases generated comparable amounts of product. Perfectly matched natural base primers generated visible product after 10 cycles, however some analog primers generated no product after 50 cycles. The analogs that did amplify with high efficiency were those that were best able to "read" the opposite strand sequence, see FIG. 4.

One product for each analog (as well as the natural base controls) were reamplified and sequenced to determine polymerase preference in inserting nucleotide bases opposite the analog, shown in Table 1. The Q$_1$, Q$_5$, Q$_6$, Q$_{16}$, and Q$_{18}$ primers generated detectable true conversion product, however only Q$_5$ primers generated almost exclusively true conversion product. No single analog functioned as a "universal base" (Hill et al., "Polymerase Recognition of Synthetic Oligodeoxyribonucleotides Incorporating Degenerate Pyrimidine and Purine Bases," *Proc. Natl. Acad. Sci. USA*, 95(8):4258–63 (1998)) capable of generalized conversion. Unexpectedly, some products contained sequences that were difficult to read across the middle four bases, suggesting single base insertions or deletions occurred during PCR extension. This was especially prevalent in products generated from mismatched natural bases (see below).

To test the ability of convertides to reduce mismatch extension errors, the effects of preconversion PCR cycles on fidelity were assessed. PCR products generated from template amplified with only natural base conversion primers were compared to products resulting from two initial PCR cycles using convertides followed by selective amplification using specific natural base primers. Preconversion PCR was performed with primer pairs containing $Q_5$, $Q_6$, and $Q_7$ analogs, since these convertides had been shown to be the most efficiently extended. To improve overall PCR fidelity and 3' mismatch primer extension, CiNF buffer, buffer G(f), was used (Day et al., *Nucleic Acids Res*, (1999)). Nine different synthetic duplex templates (SEQ. ID. Nos. 17–24) containing mutated MspI sites were amplified with or without preconversion using 3' analog preconversion primers. Both natural base conversion primers and 3' analog preconversion primers were designed to manipulate the outside bases CCGG of the MspI position, shown in FIGS. 6A–B. Some conversions were intended to serve as controls. In these cases, the original bases in the template were either restored after analog preconversion or never changed with full-length perfect match primers. All steps were performed identically between preconversion and non-preconversion reactions, except that preconversion reactions used as template the product of 2 cycles of convertide PCR for succeeding rounds of amplification, while synthetic duplex served as the starting material for PCR with no preconversion. In both cases, 3' natural base primers were used to selectively amplify the desired endproduct. These primers contained non-hybridizing zipcode sequences on their 5' ends, which ultimately served as primer binding sites for the final 20–30 cycles of PCR, shown in FIG. 6B. Conversion products were quantified by LDR, FIG. 6C.

FIG. 7 shows the products of the experiment. Overall, natural base mismatch conversion generated greater than 80% incorrect conversion products, shown in FIG. 7A, lane 9, FIG. 7B, lane 1, 3, 5, 7, 15 and 17), but preconversion could improve the fidelity and/or the yield of some conversions. In general, transversions were difficult to achieve even with preconversion. G→C and A→C conversion generated very little of the expected product with either the natural base or $Q_6$ primers (FIG. 7A, lanes 11–14). Use of $Q_6$ preconversion improved the yield of G→T and A→T conversion products (compare natural base conversion in FIG. 7B lanes 11, 13 with $Q_6$ preconversion in lanes 12 and 14). In the case of transitions, C→T conversion produced unexpected one-base shortened artifacts with natural base mismatch primers on the CXGG templates (FIG. 7B, lanes 1, 3, 5, 7, 15, and 17), but the correct products were generated when using $Q_6$ preconversion, as seen in FIG. 7B lanes 2, 4, 6, 8, 16, and 18). In addition, $Q_6$ primers did improve the yield of the expected T→C conversion product, shown in FIG. 7A lanes 9 and 10. The controls performed as expected: all C→C and T→T nonconversion reactions worked correctly without convertides, seen in FIG. 7A lanes 1, 3, 5, 7, 15, and 17, and 5B, lane 9, and the corresponding $Q_6$ preconversion products were restored to the original sequence, shown in FIG. 7A lanes 2, 4, 6, 8, 16, and 18, and FIG. 7B, lane 10). In summary, $Q_6$ preconversion reduced or eliminated artifacts produced by natural base C→T and T→C conversion and facilitated transitions in general. Transversions were only partially successful: G→T and A→T conversions could be improved with preconversion, but G→C and A→C conversion could not be achieved.

Apparently correct conversions were observed with attempted C→G and C→A transversions, however, carefully designed control templates revealed that these "conversions" were artifactual. C→G and C→A conversion appeared to be successful for templates containing a central CpG dinucleotide (FIGS. 8A and 8B, lanes 1–3, 13–21). However, the same final conversion products were observed with other templates lacking the central CpG dinucleotide, now clearly incorrect. For example, a GCGC product resulted during G conversion in reactions where the expected product should have contained T, G or A in the second position (FIG. 8A lanes 4–12). Also, an ACGT product resulted during a conversion where the expected product should have inserted a non-C base in the second position (FIG. 8B lanes 4–12, and 22–27). The mismatch primers used to alter the outer bases of the recognition site did not reach the central dinucleotide, yet these bases were altered. It is doubtful the "successful" conversions occurred through the intended mechanism, and thus represent fortuitous artifact. The yield of LDR product was low for two palindromic templates despite efficient PCR (lanes 22–27 in both FIG. 8A and FIG. 8B). These conversion reaction products presumably contain a large fraction of insertions or deletions, which cannot be detected by the current set of LDR probes. In summary, C→G conversion was partially accomplished by both $Q_5$ (FIG. 8A, lanes 5, 8, 11, and 23) and the natural base G (FIG. 8A, lanes 4, 7, 10, and 22); however, preconversion does not appear to improve conversion. C→G conversion exhibits sequence dependence.

The results of the preconversion study indicate that errors in natural base conversion were prevalent, but the use of $Q_5$, $Q_6$ and $Q_7$ convertides in preconversion reduced polymerase error in certain cases. In terms of conversion reactions, transitions were easier to accomplish than transversions. This is in agreement with previous findings: Newton et al. observed more errors in extension of primers with 3' terminal C-T, A-A, and T-T mismatches (transversions) than with purine-pyrimidine mismatches (transitions) (Newton et al., "Analysis of Any Point Mutation in DNA. The Amplification Refractory Mutation System (ARMS)," *Nucleic Acids Res.* 17(7):2503–16 (1989)). Here, pyrimidine-pyrimidine conversion usually generated the expected product, especially when using convertides. In cases of purine-pyrimidine, and pyrimidine-purine conversion, incorrect products were often generated. A summary of results is shown in Table 2, below. Formation of incorrect conversion products can be explained in part by a transient base-pair slippage of the primer 3' nucleotide (or analog) to a misaligned position on the template, as shown in FIG. 9. As a result, the sequence following the mismatch is not complementary to the original template. Consistent with this hypothesis is the observation of unreadable sequence immediately following the analog in initial sequencing experiments. Palindromic products, especially CpG dinucleotides, are themselves prone to slippage and extension. Palindromic products were frequently produced from non-palindromic templates. These artifacts were reduced by the presence of 10% formamide in the PCR buffer, presumably through destabilization of misaligned structures. Finally, nucleotide analogs produced fewer artifacts than natural bases. Different analogs produced different kinds and quantities of artifacts, perhaps according to their relative ability to base pair and stabilize a slippage misalignment. Thus, if polymerase extension is slow from an analog poorly base-paired with the template, extension from a strong transient base pair generated by slippage could exceed the rate of extension from a weakly base-paired 3' terminal base.

TABLE 2

| Starting Template[a] | First base converted to | | | |
|---|---|---|---|---|
| | | C | T | G | A |
| 1 | CCGG | C | $Q_6$ | $Q_7$ (FP) | $Q_5$ (FP) |
| 2 | CTGG | C | $Q_6$ | X (err C) | X (err C) |
| 3 | CGGG | C | $Q_6$ | $Q_5$ (err C) | X (err C) |
| 4 | CAGG | C | $Q_6$ | G (err C) | X (err C) |
| 5 | TCGA | $Q_6$ | T or $Q_6$ | $Q_7$ (FP) | $Q_5$ (FP) |
| 6 | GCGC | X (err G) | $Q_6$ | G | $Q_5$ or $Q_7$ |
| 7 | ACGT | X (err G) | $Q_6$ weak | $Q_7$ | A or $Q_7$ |
| 8 | CATG | C | X | $Q_5$ (err C) | X (err C) |
| 9 | CGCG | C | $Q_6$ | X | $Q_7$ (err C) |

[a]The 50 bp synthetic duplex DNA templates containing p53 sequence spanning codon 248 are distinguished by the four bases replacing the MspI site, which are shown.
Table 2: For the most effective conversions, see FIGS. 5 and 6. Nine duplex DNA templates were used in conversion reactions. Each contained sequence identical to p53 surrounding codon 248, except the MspI site was replaced by a different four base sequence ($B_1B_2B_3B_4$). $B_1$ and $B_4$- (opposite strand) were simultaneously converted in turn to C, T, G and A either directly by PCRusing natural base primers, or by preconversion PCR with nucleotide analog primers followed by PCR with natural base primers. In nonconversion control reactions the "conversion" product is identical to the original template. A natural base is used to indicate control reactions, and cases in which preconversion did not improve conversion. Preconversion was performed using $Q_6$ to facilitate conversion to C and T, and using $Q_5$ and $Q_7$ to facilitate conversions to G and A. Conversion primers determine $B_1$ and $B_4$; LDR was performed to detect unintended base changes in $B_2$ (which ideally is unchanged after conversion). Conversion improved by preconversion is indicated by the nucleotide analog used. Preconversion equally as effective in control reactions as natural base primers is also indicated by the analog used. Low conversion fidelity results inlarge $B_2$ error. Major $B_2$ error products are identified (e.g. err C indicates C at $B_2$), and the absence of correct product indicated no conversion method was successful (X = no correct product). Apparently correct product probably formed through a fortuitous mechanism is indicated (FP = false positive).

As discussed earlier, PCR-RFLP has been widely used to detect rare mutations. A limitation of this technique is reliance on serendipity to yield mutations that can be modified to create restriction sites in either the wild-type or the mutant template. A second limitation imposed on this approach is the need to avoid using 3' terminal mismatch primers, since extension from these primers is known to be error-prone. To date, the majority of successful attempts have used interrupted palindromic restriction sites to avoid using 3' terminal mismatch primers. Mutations in the cancer causing K-ras and H-ras were detected at a sensitivity of 1 in $10^5$ using PCR/RFLP with interrupted palindromic enzymes XmnI (Kumar et al., "Oncogene Detection at the Single Cell Level," Oncogene 3(6):647–51 (1988)), AlwNI (Anderson et al., "Prevalence of RAS Oncogene Mutation in Head and Neck Carcinomas," J. Otolaryngol., 21(5):321–6 (1992)), and BstNI or MvaI (Urban et al., "Detection of C-Ki-Ras Mutation by PCR/RFLP Analysis and Diagnosis of Pancreatic Adenocarcinomas," J. Natl. Cancer Inst., 85(24):2008–12 (1993); and Ronai et al., "Quantitative Enriched PCR (QEPCR), a Highly Sensitive Method for Detection of K-Ras Oncogene Mutation," Hum. Mutat., 10(4):322–5 (1997)). These PCR-RFLP experiments and others (Hattori et al., "Mismatch PCR RFLP Detection of DRD2 Ser311Cys Polymorphism and Schizophrenia," Biochem. Biophys. Res. Commun., 202(2):757–63 (1994); Beutler et al., "The Facile Detection of the Nt 1226 Mutation of Glucocerebrosidase by 'Mismatched' PCR," Clin. Chim. Acta., 194(2–3):161–6 (1990); Hingorani et al., "A Simple Molecular Assay for the C1166 Variant of the Angiotensin II Type 1 Receptor Gene," Biochem. Biophys. Res. Commun., 213(2):725–9 (1995); Kuwata et al., J Allergy Clin Immunol, 96(6 Pt 2):1051–60 (1995); Nishiwaki et al., "Mutational Screening of APP Gene in Patients with Early-Onset Alzheimer Disease Utilizing Mismatched PCR-RFLP," Clin. Genet., 49(3):119–23 (1996); and Ishihara et al., "Analysis of Allelic Variation of the TAP2 Gene in Sarcoidosis," Tissue Antigens, 49(2):107–10 (1997)) avoid 3' terminal mismatches, however most cancer mutations are in sequences that cannot be converted to interrupted palindromes, for example at CpG dinucleotides. A larger fraction of mutations would be made into targets for detection if contiguous recognition sequences could be introduced with as few errors as interrupted palindromic recognition sequences. Currently, contiguous restriction sites are introduced by terminal 3' mismatch primer extension, which is prone to errors. O'Dell et al. tested a general method for introducing different restriction sites at CpG dinucleotides using mismatch PCR(O'Dell et al., "PCR Induction of a TaqI Restriction Site at Any CpG Dinucleotide Using Two Mismatched Primers (CpG-PCR)," Genome Res., 6(6):558–68 (1996)). The outer bases of four different CpG dinucleotides in the human LDL receptor gene were altered to create TaqI (TCGA), MspI (CCGG) or RhaI (GCGC) sites. In these targets, TaqI sites were successfully generated by 3' T mismatch primers. The method was able to detect homozygous and heterozygous individuals; however, the ratio of products representing each allele was not equal, as is expected in germline mutations. Several cases have been shown here where T mismatch conversion failed to create a TaqI site. Thus the method is sequence dependent. O'Dell et al. found that C and G mismatch conversion failed. These results agree with O'Dell's conclusion that stronger base pairing leads to mispriming, possibly through stabilization of primer slippage on the template. Gotoda et al., "Detection of Three Separate DNA Polymorphisms in the Human Lipoprotein Lipase Gene by Gene Amplification and Restriction Endonuclease Digestion," J. Lipid Res. 33(7): 1067–72 (1992), claim to have successfully used PCR-RFLP to introduce a MaeII site (ACGT) by extension of a 3' C-A mismatch to produce a T→C transition (Gotoda et al., "Detection of Three Separate DNA Polymorphisms in the Human Lipoprotein Lipase Gene by Gene Amplification and Restriction Endonuclease Digestion," J. Lipid Res. 33(7): 1067–72 (1992)). Athma et al. used PCR extension of a 3' terminal mismatch primer to create a restriction site for discriminating between two alleles (Athma et al., "Single Base Polymorphism Linked to the Ataxia-Telangiectasia Locus is Detected by Mismatch PCR," Biochem. Biophys. Res. Commun., 210(3):982–6 (1995)). A G-T mismatch produced an MvaI site (CC A/T GG) through an A→G transition. Successful A→G conversions have been performed in accordance with the method of the present invention, using a natural base mismatch, but difficulties with T→C conversion by natural base primers has been encountered. Transitions can be accomplished more readily than transversions, but the yield of correct product can be sequence dependent. Others have also found that PCR-RFLP can produce false-positive results (Hodanova et al., "Incorrect Assignment of N370S Mutation Status by Mismatched PCR/RFLP Method in Two Gaucher Patients," J. Inherit. Metab. Dis., 20(4):611–2 (1997)). The use herein of ligase detection reaction allows the determination of the precise amounts of misextension products generated.

The fidelity of polymerase extension from primers containing 3' natural bases and nucleotide analogs has been measured. Results indicate that natural base mismatch primer extension cannot be used as a general technique to create restriction sites in any given sequence for RFLP analysis. Primer slippage appears to be an important mechanism for producing error in mismatch primer extension. This source of error may have a dramatic impact on some allele-specific PCR and other methods of high sensitivity mutation detection. With further development and testing of nucleotide analogs to facilitate conversion, mismatch primer extension may become a technique that can efficiently introduce desired mutations with few artifacts. It has been found some nucleotide analogs improve mismatch primer extension (see Table 3, below). Further improvement of 3' mismatch extension will be required to minimize the high degree of context dependent error seen in transversions and lead to improved levels of sensitivity and broader scope of PCR/RFLP based mutation detection.

TABLE 3

| Starting Base | Conversion to | | | |
|---|---|---|---|---|
| | C | T | G | A |
| C | C | $Q_6$ | | |
| T | $Q_6$ | T | | |
| G | | | G | A or $Q_7$ |
| A | | $Q_5$ or $Q_7$ | | A |

Table 3. Summary of conversion strategy. A $Q_n$ convertite indicates preconversion is required using the indicated convertide prior to final conversion using natural base primers. In some cases, an additional convertide or using only the natural base will result in the desired conversion.

Example 9

Oligonucleotide Synthesis for PCR/RE/LDR

Oligonucleotides were synthesized at the 0.2 μmole scale by cyanoethyl phosphoramidite chemistry on an Applied Biosystems 394 DNA synthesizer. Standard 500 Å CPG columns and reagents (Applied Biosystems) were used with the following exceptions: oligonucleotides 50 bases in length were synthesized using wide-pore 1000 Å CPG columns (Applied Biosystems); oligonucleotides with fluorescent dye FAM at the 5' terminus were synthesized using FAM phosphoramidite (Applied Biosystems) with a 15 minute coupling step; oligonucleotides with 5' phosphate were synthesized using phosphorylation reagent (Glen Research) with a 15 minute coupling step. Oligonucleotides with 3' blocking group were synthesized using 3'-Spacer CPG columns (Glen Research). Oligonucleotides with the 3' nucleotide analog 6-(2-deoxy-B-D-ribofuranosyl)- 6H,8H-3,4-dihydropyrimido[4,5-c][1,2]oxazine-7-one ($Q_6$) were synthesized using dP-CpG (Glen Research).

Example 10

PCR Polymerases and Buffers for PCR/RE/LDR

The polymerases used were AmpliTaq (Applied Biosystems), Vent and Vent(exo-) (New England Biolabs), and Expand polymerase mix (Taq and PwoI polymerase mixture, in Expand High Fidelity kit, Boehringer Mannheim). The commercially available PCR buffers used were supplied in the AmpliTaq and Expand kits. Tris pH 9.1 (pH values were measured using 1 M stock solutions at 23° C.), tricine pH 8.7, EPPS(N-[2-hydroxyethyl]piperazine-N'-3-propane-sulfonic acid) pH 8.4, and citrate pH 7.6 (Sigma) were used for alternative PCR buffers. Unless otherwise noted, each 20 μl reaction contained 20 mM Tris, tricine, or citrate, 200 pg/ml bovine serum albumin, 2.5 mM MgCl2, 200 μM dNTP (each) and either 16 mM $(NH_4)_2SO_4$, or 50 mM potassium acetate. Formamide at 10% concentration was used as indicated (see Example 11, below). PCR buffers were made as 10% stocks requiring the addition of formamide as needed, dNTPs, and the oligonucleotide primers and template DNA.

Example 11

Enzyme Buffer Notation

Test PCR buffers are named to indicate the presence of one or more components: Tris/potassium acetate=buffer A; Tris/ammonium sulfate=buffer B; Tricine/ammonium sulfate=buffer D; EPPS/potassium sulfate=buffer E; EPPS/ammonium sulfate=buffer F; and Citrate/ammonium sulfate=buffer G. Component concentrations are described above.

Example 12

Amplification of p53 exon 7 from Genomic DNA

Part of p53 exon 7 surrounding codon 248 was amplified as shown in FIG. 10. The upstream primer has nucleotide sequence corresponding to SEQ. ID. NO. 35, as follows:
    5'-GCCTCATCTTGGGCCTGTGTTATC-3' hybridized within the preceding intron, and the downstream primer, with a nucleotide sequence corresponding to SEQ. ID. NO. 36, as follows:
    5'-GTGGATGGGTAGTAGTATGGAAGAAATC-3' hybridized within exon 7. All PCR, restriction endonuclease digestion and ligation steps described throughout were performed using a GeneAmp PCR System 2400 (Perkin-Elmer). Several buffers and enzymes were used as indicated in Examples 10 and 11. The p53 exon 7 amplification from genomic DNA was performed starting with a 20 μl reaction mixture containing 50 ng of DNA, 2.5 mM of each dNTP, and 12.5 pmol of each primer in 1× buffer without polymerase. The reaction mixture was covered with paraffin oil and preincubated for at least 1.5 min at 94° C. in order to perform hot start by adding 1 μl of polymerase diluted in 1× buffer to introduce the required units of polymerase. The exon 7 segment was amplified for 40 cycles of 94° C. 15 sec, 65° C. 2 min, with an additional 5 min at 65° C. at the end of the last cycle. PCR amplifications departing from this procedure were performed as indicated.

Example 13

PCR/RE/LDR: Fidelity Assay

Templates were amplified with conversion primer pairs bracketing the central two basepairs of the MspI site (CCGG) at codon 248 (FIG. 11B). Tubes were prepared containing 10 fmol per reaction of either PCR amplified p53 exon 7 or wild-type synthetic duplex template, PCR buffer, and primers. In parallel reactions, a synthetic 50 bp duplex marker template (MK), with the sequence CGGG replacing the MspI site at codon 248, was added at $10^{-3}$, $10^{-4}$, $10^{-5}$ and 0 molar ratio to wild-type template. Reactions were preincubated for at least 1.5 min at 94° C. with all components present in CiNF buffer, buffer G(f), except Vent (exo-) polymerase. A "hot start" was performed by adding 1 μl of polymerase at 94° C. When preconversion was performed, 2 cycles of 94° C. 15 sec, 55° C. 1 min, 60° C. 1 min were executed with 500 fmol each of the primers p53-248$Q_6$ and p53-248$Q_6$R. Afterwards, 1 pmol of p53Taq248T (SEQ. ID. No. 30) and p53Taq248TR (SEQ. ID. No. 31) primers were added. When preconversion was not performed, the reactions contained 1 pmol each of the primers p53Taq248T and p53Taq248TR or the control primers p53Msp248C and p53Msp248CR. After reactions with and without preconversion were performed, conversion PCR was carried out as follows: 5 cycles of 94° C. 15 sec, 55° C.+1°/cyc 1 min (temperature ramp), 60° C. 1 min; then, 20 cycles of 94° C. 15 sec, 60° C. 2 min; then, a final 60° C. 5 min extension. After 3 cycles of the temperature ramp 10 pmol of long zipcode conversion primers p53zip248T (SEQ. ID. No. 9) and p53zip248TR (SEQ. ID. No. 10), or p53zip248C (SEQ. ID. No. 25) and p53zip248CR, were added. After conversion, the wild-type DNA was digested periodically during 20 cycles of "zipcode" PCR (described below). Polymerase was inactivated by freezing and thawing twice. Finally, LDR was performed to detect the conversion products without contribution from the original template (except in nonconversion control reactions).

Example 14

PCR/RE/LDR: "Zipcode" PCR

Wild-type sequences or wild-type conversion products were removed by restriction digestion. The appropriate restriction endonuclease was added to the reaction tube and supplemented with additional $MgCl_2$ as required to allow efficient digestion. MspI digestion was performed at 37° C. for 15 min using no additional $MgCl_2$, except when using citrate buffer. TaqI digestion was performed at 65° C. for 30 min at 6 mM $Mg^{2+}$ by adding 1 μl of enzyme diluted in 140 mM $MgCl_2$. The undigested conversion products were reamplified from 1 μl of a 10× dilution added to a 20 μl PCR reaction containing 10 pmol of the "zipcode" primers Ztop (SEQ. ID. No. 7) and Zbot (SEQ. ID. No. 8) (FIG. 6B). These zipcode primers each contain a DNA sequence that is not similar in sequence to any genomic sequences present in the sample, thus only the products of previous PCR using primers containing the zipcode sequences will be efficiently amplified. Conversion products were amplified using Expand polymerase mix and buffer (see Example 10) After an initial RE digest, zipcode PCR reamplification followed by redigestion was performed as follows: reactions were preincubated at 94° C. for at least 1.5 min then initiated with a hot start by adding 0.1 μl of RE digested sample (1 μl of a 10× dilution) to a 20 μl reaction; 10 cycles of 94° C. 15 sec, 65° C. 2 min. Zipcode PCR amplification products were redigested as described above.

Example 15

PCR/RE/LDR: Ligase Detection Reaction

Ligase detection reactions were performed in standard LDR buffer (25 mM Tris pH 7.6, 12 mM $MgCl_2$, 65 μg/ml bovine serum albumin, 100 mM KCl, and 10 mM DTT). Each 20 μl reaction contained approximately 500 fmol of dsDNA (1 μl of PCR sample), 500 fmol of each discriminating probe (SEQ. ID. Nos. 11–14), and 750 fmol of common probe (SEQ. ID. No. 15), shown in FIG. 11C. Sets of discrimination and common probes were synthesized to detect the expected conversion products; i.e., converted to CNGG or TNGA at the MspI position. The common probe was synthesized using 3'-Spacer C3 CPG columns and the 5' end was phosphorylated on the column using phosphorylation reagent. Discrimination probes of each set varied at the 3' terminal base to query the base in that location, i.e., the second base of the MspI position. Discrimination probes had 5' tails of different length and a FAM label for fluorescence detection. The tail size identified the probe and allowed physical separation of different LDR products on an acrylamide gel.

The LDR reaction was preincubated for 1.5 min at 94° C. prior to the addition of 5 nmol Tth ligase enzyme under a layer of mineral oil. 10 LDR cycles of 94° C. 15 sec, 65° C. 2 min. were used. The reactions were then held at 94° C. until cold quenched on ice and stored at −70° C. The LDR products were separated on 10% acrylamide gels containing 7M urea with 0.6×TBE (1×TBE contains 90 mM Tris base, 90 mM Borate, 2 mM EDTA) used in the gel and for the running buffer. Data were collected using an ABI 373 automated DNA sequencer and Applied Biosystems Genescan 672 software (GS Collection and GS Analysis).

Example 16

Image Processing for PCR/RE/LDR

Raw gel pictures were produced by the ABI GS Analysis software. Dye specific pictures were opened in Adobe Photoshop 3.0, cropped, resized, and converted to grayscale. The grayscale images were opened in NIH Image 1.59, inverted and 1D vertical background was subtracted. Optionally, NIH Image could render a 3-D plot from a corrected 2-D picture. Background corrected pictures were reinverted and rendered in pseudocolor by Photoshop by replacing the color table to make subtle intensity differences easier to compare. Except for color replacement, only linear image processing was performed in order to preserve relative intensities.

Example 17

PCR/RE/LDR Optimization

In FIG. 10, PCR/RE/LDR was developed to detect and identify low abundance mutations occurring within the MspI site (CCGG) at codon 248 in the p53 gene. An initial PCR amplifies exon 7 from genomic DNA, shown in FIG. 10A. This product serves as the template for a second PCR that amplifies the central CpG dinucleotide in the MspI site. To generate a restriction site in sequence lacking a preexisting site, mismatch primers are used to alter one or more bases flanking the CpG dinucleotide. This results in a conversion PCR that creates a restriction site (NCGN→TCGA) TaqI site, for example, as in FIG. 10B. In a generalized method for introducing contiguous Type II restriction sites, conversion PCR primers by necessity have 3' terminal mismatches. To avoid unfavorable natural base mismatches that may result in insertion of an erroneous base at the next site (O'Dell et al., *Genome Res.*, 6(6):558–68 (1996); and Eiken et al., "Application of Natural and Amplification Created Restriction Sites for the Diagnosis of PKU Mutations," *Nucleic Acids Res.*, 19(7): 1427–30 (1991)), preconversion with 3' nucleotide analog primers is performed. However, extension with 3' analog primers produces a pool of degenerate products (Day et al., *Nucleic Acids Res.*, (1999)). Thus, after this preconversion step, natural base primers are used to selectively amplify the desired products.

Mismatch conversion error relative to PCR error was assessed by performing parallel nonconversion control reactions and true conversion reactions with and without preconversion. Nonconversion reaction products retained the MspI site (CCGG) (see FIG. 10A), while conversion introduces a TaqI site (TCGA) (see FIG. 10B). All PCR/RE/LDR steps were performed under similar conditions, varying only the primers and restriction endonuclease (MspI or TaqI). In both cases, noncleavable DNA is preferentially amplified. When wild-type DNA is selectively removed by digestion, it is necessary to determine the proportion of DNA with incorrect sequence produced relative to the initial quantity of DNA in the sample, which is nearly 100% wild-type. Parallel reactions were performed in which known fractions of marker (MK) DNA were present. The MK DNA contained a single base change in the MspI site (CGGG), rendering it uncleavable by MspI. C→G transversions are unlikely to occur through polymerase error. The MK standard curve allows quantification of mutations detected by LDR. FIG. 10C shows the LDR quantification of mutant sequencing using a marker. PCR conditions were tested to minimize PCR error (observed in the nonconversion reactions) and mismatch extension errors (additional errors observed in the conversion reactions).

Various proofreading and nonproofreading polymerases were tested, as different polymerase properties are required during target amplification from genomic DNA, conversion, and reamplification steps in PCR/RE/LDR. Since it is essential throughout PCR/RE/LDR to minimize any alteration of the bases assayed by LDR, proofreading polymerases might seem the logical choice for maintaining the highest fidelity (Keohavong et al., *PCR Meth. Appl.,* 2:288–92 (1993)); however, they may interfere with conversion by mismatch primer extension. Hence, PCR conditions must be found which maximize the fidelity of nonproofreading polymerases (Keohavong et al., *Proc. Natl. Acad. Sci. USA,* 86)23):9253–7 (1989)).

Initially, PCR/RE/LDR was used as a high sensitivity assay to determine PCR conditions that maintain the highest fidelity throughout the procedure. Two main sources of error were expected: 1) polymerase misincorporation, and 2) DNA template degradation. Raising the PCR buffer pH improves long PCR, probably by decreasing depurination which leads to strand cleavage (Barnes, "PCR Amplification of up to 35-Kb DNA with High Fidelity and High Yield from Lambda Bacteriophage Templates," *Proc. Natl. Acad. Sci. USA,* 91(6):2216–20 (1994); Cheng et al., "Effective Amplification of Long Targets from Cloned Inserts and Human Genomic DNA," *Proc. Natl. Acad. Sci. USA,* 91(12):5695–9 (1994); and Sang et al., "Generation of Site-Directed Mutagenesis by Extralong, High-Fidelity Polymerase Chain Reaction," *Anal. Biochem.,* 233(1):142–4 (1996)). While higher pH may decrease template damage, higher pH is also known to adversely affect polymerase fidelity (Eckert et al., "High Fidelity DNA Synthesis by the *Thermus Aquaticus* DNA Polymerase," *Nucleic Acids Res.,* 18(13):3739-44 (1990); Eckert et al., "DNA Polymerase Fidelity and the Polymerase Chain Reaction," *PCR Methods Appl.,* 1(1): 17–24 (1991); and Cline et al., "PCR Fidelity of Pfu DNA Polymerase and Other Thermostable DNA Polymerases," *Nucleic Acids Res.,* 24(18):3546–51 (1996)). Therefore, other buffers were also tested: tricine, EPPS, and citrate buffers, which have $pK_a$s in the range of 7 to 8 and $|\Delta pK_a|$ lower than Tris. Tris cannot meet the dual constraints of a slightly alkaline pH at high temperature to maintain template integrity and neutral pH at the extension temperature to maintain polymerase fidelity, although most PCR fidelity and long PCR studies use Tris. Some investigators have explored the use of alternative buffers with lower $|\Delta pK_a|$ (Eckert et al., "High Fidelity DNA Synthesis by the *Thermus Aquaticus* DNA Polymerase," *Nucleic Acids Res.,* 18(13): 3739–44 (1990); Eckert et al., "DNA Polymerase Fidelity and the Polymerase Chain Reaction," *PCR Methods Appl.,* 1(1):17–24 (1991); and Brail et al., "Improved Polymerase Fidelity in PCR-SSCPA," *Mutat. Res.,* 303(4):171–5 (1993)). Buffer-specific effects on PCR were tested for purposes of optimizing the buffer conditions of the present invention by making PCR buffers containing identical components except for the buffering compound. Making one set of test PCR buffers with ammonium sulfate and another with potassium acetate tested salt effects. The $\Delta pK_a$ of each buffer was determined in pure solution and in 1×PCR buffer mixtures (data not shown). Results of these tests agreed with published $\Delta pK_a$ values of pure buffers (Good, "Amine Buffers Useful for Biological Research," in Fasman, ed., *Handbook of Biochemistry and Molecular Biology*, Cleveland, Ohio: CRC Press, Inc., pp. 367–369 (1976); and Blanchard, "Buffers for Enzymes," *Meth. Enzymol.,* 104: 404–14 (1984)) corrected by a small constant (0.005 pH units/° C.), possibly due to a temperature-dependence of the pH probe itself. The pH of the each test PCR buffer was adjusted to produce approximately neutral pH at 65° C. However, the 1×PCR buffers had somewhat different $\Delta pK_a$s compared to the pure buffers; for example, 1×TsN, buffer B, had $\Delta pK_a$=–0.033/° C. versus–0.030/° C. for 100 mM Tris, and 1×TcK, buffer C, had $\Delta pK_a$=–0.022/° C. versus–0.025/° C. for 100 mM tricine.

Test PCR buffers containing Tris, tricine, or EPPS were used to test PCR fidelity with no conversion of the MspI site (CCGG) at codon 248 of p53 (FIG. 12). The objective in this experiment was to test the error rate of PCR using various buffers and polymerase enzymes. Since introduced errors create template that cannot be cleaved by the selected restriction enzyme, false-positives accumulate as this error template continues to amplify alongside true mutant DNA. This established the conditions necessary to achieve amplification while minimizing error. The same polymerase and buffer set was used in both preamplification of p53 exon 7 from genomic DNA and in the "conversion" step. As mentioned, the "conversion" step maintains the MspI site by using perfectly matched primers whose 3' ends terminate on the C and G bases flanking the central CpG. After an initial MspI digest, template and amplification products were periodically redigested every ten cycles during reamplification to remove WT sequence. Synthetic marker mutant MK with the sequence CGGG was present in these reactions at $10^{-3}$, $10^{-4}$, or $10^{-5}$ and 0 ratio to wild-type (WT). MK will not be cleaved by MspI restriction digestion, but will amplify with each PCR cycle to provide an internal control to measure product quantities (see below). The MK product will also maintain its sequence, as the perfect match primers in the conversion step will again terminate on the C and G bases flanking the central GG. Error products resulting from MK PCR will in general lack MspI sites and will be indistinguishable from regular MK template. If an MspI site is accidentally created, the product will be destroyed by digestion. If false LDR error products are also generate, these can be detected by comparison with a "no marker" control.

For each buffer, LDR detected MK products in each of the four parallel reactions, with the 0 MK control indicating the background level of CGGG error produced. The intensities of other error products detected by LDR were compared to MK to estimate the fraction of each error product generated. AmpliTaq generated few transversions (C→G or C→A), but a large amount of C→T transition was observed, as shown in FIG. 12A. Vent generated much less of the C→T transition compared to AmpliTaq (FIG. 12B). AmpliTaq showed little dependence on the presence of potassium acetate in buffers A, C, and E (FIG. 12A lanes 1–4, 9–12, 17–20) versus ammonium sulfate in buffers B, D, and F (FIG. 12A lanes 5–8, 13–16, 21–24). Vent polymerase amplified template more efficiently in Tris/ammonium sulfate buffer B than Tris/potassium acetate buffer A (FIG. 12B lanes 1–4 versus lanes 5–8), as described previously (Barnes, "PCR Amplification of up to 35-Kb DNA with High Fidelity and High Yield from Lambda Bacteriophage Templates," *Proc. Natl. Acad. Sci. USA*, 91(6):2216–20 (1994); Keohavong et al., *PCR Meth. Appl.* 2:288–92 (1993); Cariello et al., "Fidelity of *Thermococcus Litoralis* DNA Polymerase (Vent) in PCR Determined by Denaturing Gradient Gel Electrophoresis," *Nucleic Acids Res.*, 19(15):4193–8 (1991); and Mattila et al., "Fidelity of DNA Synthesis by the *Thermococcus Litoralis* DNA Polymerase—An Extremely Heat Stable Enzyme with Proofreading Activity," *Nucleic Acids Res.*, 19(18):4967–73 (1991)). However, Vent exhibited improved fidelity in tricine/potassium acetate buffer C (FIG. 12B lanes 9–12) and EPPS buffer E (FIG. 12B lanes 17–20) compared to tricine/ammonium sulfate buffer D (FIG. 12B lanes 13–16) and EPPS/ammonium sulfate buffer F (FIG. 12B lanes 21–24).

The relative fidelities of the different polymerase-buffer combinations may be described by their "sensitivity" expressed as the $-\log_{10}$ of the ratio of MK to WT initially present. The C→T error for AmpliTaq amplification in Tris/potassium acetate buffer A can be taken as an example. If the signal for the CTGG error product (FIG. 12A lane 2) is compared to the MK CGGG signal (FIG. 12A lanes 1–3), the intensity of the signal most resembles the $10^{-3}$ MK:WT dilution (FIG. 12A lane 1). Thus, the C→T error rate is $10^{-3}$; the sensitivity is 3, since $-\log[MK/WT]=-\log[10^{-3}]=3$. From this it can be seen that the higher the sensitivity, the lower the error rate. Reactions with higher sensitivities for each mutation had the highest overall fidelity (Results summarized in Table 1). Many of the Vent reactions had sensitivities of 5 (i.e., 1 in $10^5$) for every mutation (FIG. 12B), while the AmpliTaq reactions had sensitivities of 3 (i.e, 1 in $10^3$), as shown in FIG. 12A. Sensitivity indicates the usefulness of the assay rather than the error rate of the polymerase. Error (ER) per base per cycle may be estimated from the fraction (F) of all mutations occurring at one base which accumulated over 65 cycles (D) before digestion. For purposes of the present invention, the number of cycles is an estimate of the number of duplications, since multiple non-saturating PCRs were performed. From ER=F/D, Vent polymerase had an error rate of less than $1\times10^{-7}$/base/cycle in tricine/potassium acetate buffer C, approximately $2\times10^{-7}$/base/cycle in tricine/ammonium sulfate buffer D, and $2\times10^{-6}$/base/cycle in TsN, buffer B. An error rate of $2\times10^{-5}$/base/cycle was observed. This was due mainly to the C→T transition for AmpliTaq in tris/potassium acetate buffer A. Elimination of this artifact could improve AmpliTaq fidelity by more than 10-fold. Others have used cloning and screening methods to estimate polymerase error (Eckert et al., "High Fidelity DNA Synthesis by the *Thermus Aquaticus* DNA Polymerase," *Nucleic Acids Res.*, 18(13):3739–44 (1990); Cline et al., "PCR Fidelity of Pfu DNA Polymerase and Other Thermostable DNA Polymerases," *Nucleic Acids Res.*, 24(18):3546–51 (1996); Mattila et al., "Fidelity of DNA Synthesis by the *Thermococcus Litoralis* DNA Polymerase—An Extremely Heat Stable Enzyme with Proofreading Activity," *Nucleic Acids Res.* 19(18):4967–73 (1991); and Huang et al., "Fidelity and Predominant Mutations Produced by Deep Vent Wild-Type and Exonuclease-Deficient DNA Polymerases During in Vitro DNA Amplification," *DNA Cell Biol.*, 15(7):589–94 (1996)), and denaturing gradient gel electrophoresis (DGGE) has also been used (Keohavong et al., *PCR Meth. Appl.*, 2:288–92 (1993); Keohavong et al., *Proc. Natl. Acad. Sci. USA*, 86)23):9253–7 (1989); Cariello et al., "Fidelity of *Thermococcus Litoralis* DNA Polymerase (Vent) in PCR Determined by Denaturing Gradient Gel Electrophoresis," *Nucleic Acids Res.*, 19(15):4193–8 (1991); and Ling et al., "Optimization of the Polymerase Chain Reaction with Regard to Fidelity: Modified T7, Taq, and Vent DNA Polymerases," *PCR Methods Appl.*, 1(1):63–9 (1991)). However, these methods do not directly measure mutated DNA, and do not detect all mutations. By cloning and DGGE methods, Vent polymerase has an error rate estimated from 0.3 to $4\times10^{-5}$/base/cycle (Cariello et al., "Fidelity of *Thermococcus Litoralis* DNA Polymerase (Vent) in PCR Determined by Denaturing Gradient Gel Electrophoresis," *Nucleic Acids Res.*, 19(15):4193–8 (1991); and Ling et al., "Optimization of the Polymerase Chain Reaction with Regard to Fidelity: Modified T7, Taq, and Vent DNA Polymerases," *PCR Methods Appl.*, 1(1):63–9 (1991)). The error rate of Taq polymerase has been estimated from 0.8 to $9\times10^{-5}$/base/cycle (Eckert et al., "High Fidelity DNA Synthesis by the *Thermus Aquaticus* DNA Polymerase," *Nucleic Acids Res.*, 18(13):3739–44 (1990); Cline et al., "PCR Fidelity of Pfu DNA Polymerase and Other Thermostable DNA Polymerases," *Nucleic Acids Res.*, 24(18):3546–51 (1996); and Brail et al., "Improved Polymerase Fidelity in PCR-SSCPA," *Mutat. Res.*, 303(4):171–5 (1993)), comparable to the error rate we observed for AmpliTaq in TsK, buffer A. Of the thermostable polymerases, Pfu has the lowest reported error rate estimated from 0.7 to $1.6\times10^{-6}$/base/cycle (Cline et al., "PCR Fidelity of Pfu DNA Polymerase and Other Thermostable DNA Polymerases," *Nucleic Acids Res.* 24(18):3546–51 (1996); Lundberg et al., "High-Fidelity Amplification Using a Thermostable DNA Polymerase Isolated from *Pyrococcus Furiosus*," *Gene*, 108(1):1–6 (1991); and Andre et al., "Fidelity and Mutational Spectrum of Pfu DNA Polymerase on a Human Mitochondrial DNA Sequence," *Genome Res.*, 7(8): 843–52 (1997)). Pfu polymerase may also exhibit improved fidelity in tricine or other low $|\Delta pK_a|$ buffers.

While high fidelity proofreading enzymes appeared to improve amplification from genomic DNA, proofreading still must be avoided in the conversion step. Different high fidelity genomic amplification conditions were tested in combination with fixed conversion conditions. Genomic amplification was performed with either Vent(exo-) Citrate/ammonium sulfate, buffer G, or Vent(exo-) Citrate/ammonium sulfate, buffer G, with 10% formamide buffer G(f) (see Table 4). Nonconversion primers were used with Vent(exo-) to optimize PCR fidelity in anticipation of conversion by mismatch primer extension. The highest fidelity conditions were as follows: Genomic amplifications with Vent/Buffer G were initiated by spiking genomic amplification product from Expand/Buffer C with 10% formamide reactions after 3 cycles. These Vent/Buffer G reactions required 4 mM $Mg^{2+}$ and PCR primers, but no additional genomic DNA was provided. See Table 4 for observed error rate with other conditions tested.

TABLE 4

| Polymerase enzymes 1) Genomic DNA PCR → 2) conversion | Buffer 1)→2) | Limiting error | Error rate total | per cycle[a] |
|---|---|---|---|---|
| Taq → Taq | A→A | C→T | $10^{-3}$ | $2 \times 10^{-5}$ |
| " | B→B | " | $10^{-3}$ | $2 \times 10^{-5}$ |
| " | C→C | " | $10^{-3}$ | $2 \times 10^{-5}$ |
| " | D→D | " | $10^{-3}$ | $2 \times 10^{-5}$ |
| " | E→E | " | $10^{-3}$ | $2 \times 10^{-5}$ |
| " | F→F | " | $10^{-3}$ | $2 \times 10^{-5}$ |
| Taq[b] → Vent | A→A | C→T | $>10^{-3}$ | $>2 \times 10^{-5}$ |
| Vent → Vent | B→B | " | $10^{-5}$ | $2 \times 10^{-7}$ |
| " | C→C | " | $>10^{-5}$ | $>2 \times 10^{-7}$ |
| " | D→D | " | $10^{-4}$ | $2 \times 10^{-6}$ |
| " | E→E | " | $>10^{-5}$ | $>2 \times 10^{-7}$ |
| " | F→F | " | $10^{-5}$ | $2 \times 10^{-7}$ |
| Vent (exo-) → Vent | C→G | C→T | $10^{-4}$ | $2 \times 10^{-6}$ |
| Vent (exo-) → Vent (exo-) | C→G | " | $10^{-3}$ | $2 \times 10^{-5}$ |
| Vent → Vent (exo-) | C→G | " | $10^{-4}$ | $2 \times 10^{-6}$ |
| Vent → Vent (exo-) | C→G(f) | " | $10^{-5}$ | $2 \times 10^{-7}$ |
| Vent[c] → Vent (exo-) | G(4)→G | " | $10^{-4}$ | $2 \times 10^{-6}$ |
| Vent → Vent (exo-) | G(8)→G(f) | " | $10^{-5}$ | $2 \times 10^{-7}$ |
| Vent[c] → Vent (exo-) | G(4)→G(f) | " | $>10^{-5}$ | $>2 \times 10^{-7}$ |

[a]Based on minimum of 50 total cycles, i.e. observed error + 50.
[b]No vent PCR product from genomic DNA. Used Taq amplified product for Vent conversion PCR.
[c]Template added by taking 1 µl after 3rd PCR cycle from a parallel genomic DNA amplification using Expand polymerase mix in Buffer C.
Table 4. Comparison of fidelity using proofreading and nonproofreading polymerases in different buffers for PCR to amplify the target sequence from genomic DNA and for conversion PCR. Taq and Vent polymerases were initially tested using one buffer for genomic amplification and conversion. During the conversion step, only nonconversion of the MspI site near p53 codon 248 was performed using short perfect match primers(FIG. 11A) to determine the background level of polymerase error. LDR quantified MspI site mutations at the second position (CCGG → CNGG). Fidelity was compared in parallel reactions using proofreading and nonproofreading polymerases in genomic amplification and conversion. Expand polymerase mix, Taq with proofreading Pfu polymerase added, was used to initiate target amplification from genomic DNA for subsequent highfidelity Vent polymerase PCR. Vent polymerase was substituted with nonproofreading Vent(exo-) to determine whether proofreading was required and also in the conversion step where proofreading is not permitted. The effect of 10% formamide in the conversion PCR buffer was also tested. All buffers contained 200 µg/ml bovine serum albumin, 2.5 mM MgCl$_2$, and 200 µM dNTP (each). Specific components were:
A (TsK), 20 mM Tris pH 9.1, 50 mM potassium acetate (standard Taq polymerase buffer).
B (TsN): 20 mM Tris pH 9.1, 16 mM ammonium sulfate (standard Vent polymerase buffer).
C (TcK): 20 mM tricine pH 8.7, 50 mM potassium acetate.
D (TcN): 20 mM tricine pH 8.7, 16 mM ammonium sulfate.
E (EpK): 20 mM EPPS pH 8.4, 50 mM potassium acetate.
F (EpN): 20 mM EPPS pH 8.4, 16 mM ammonium sulfate.
G (CiN): 20 mM citrate pH 7.6, 16 mM ammonium sulfate.
(f) indicates presence of 10% formamide.
(4) indicates increase to 4 mM MgCl$_2$.
(8) indicates increase to 8 mM MgCl$_2$.

PCR conditions were found for each step in PCR/RE/LDR that maintain high fidelity when no mismatch conversion was performed. Using known high fidelity PCR conditions, conversion was also tested by changing the p53 codon 248 MspI site (CCGG) into a TaqI site (TCGA). MK (CGGG) was added as before in parallel reactions to measure fidelity relative to the initial wild-type DNA present. High fidelity PCR was performed as described above and some (but not all) reactions were subjected to preconversion. Preconversion was performed using primers containing the degenerate pyrimidine nucleotide analog $Q_6$ at their 3' ends, as shown in FIG. 10B. The final conversion was accomplished using natural base 3' T mismatch primers. Products were detected using LDR to interrogate the second base position in the MspI, TaqI and MK sequence: CNGG or TNGA. Fidelity for conversion with and without preconversion was compared to a nonconversion control. Successful conversion will change the MspI site (CCGG) into a TaqI site (TCGA); MK will also be converted from CGGG to TGGA. However, the main issue of conversion success is the maintenance of the central bases in all cases: CpG for TaqI conversions and GpG for MK. FIG. 13 shows the results of conversion. In FIG. 13, lanes 1–4 (C:G) are nonconverted reactions that were digested with MspI; lanes 5–8 ($Q_6$:G) are preconverted/converted reactions that were digested with TaqI; lanes 9–12 (T:G) are converted reactions lacking preconversion that were digested with TaqI. PCR/RE/LDR with no conversion was sensitive to better than 1 in $10^4$ using the previously determined best conditions for preamplification and conversion shown in FIG. 13, C:G lanes 1–4. PCR/RE/LDR with conversion of the MspI site to a TaqI site by T mismatch primers was apparently very successful at first glance, FIG. 13, T:G lanes 9–12. As would be expected for successful conversion, no MspI product can be detected in the _CG_ region of the figure; hence, it appears that the site was converted to TaqI and then digested. However, although a very large fraction of MK (CGGG) is observed in the reactions with added MK, FIG. 13, T:G lanes 9–11; the same large fraction is also observed in the 0 MK control lane in FIG. 13, T:G lane 12. Thus, the entire quantity of MK is an artifact produced by mismatch extension of the natural base T primers. This event would convert the second position C in the MspI site to a G during extension, mimicking the internal sequence of MK (CCGG→TGGA). Preconversion with $Q_6$ primers eliminates the MK artifact, $Q_6$:G lanes 5–8.

The greater amount of WT present in nonconverted samples, shown in FIG. 13 lanes 1–4, compared to $Q_6$ converted samples, lanes 5–8, may be due to inhibition of MspI digestion by formamide. Formamide apparently inhibits MspI digestion as evidenced by the presence of strong wild-type LDR bands (WT) in the nonconversion control, C:G lanes, which are not present after TaqI digestion of the converted sequence, $Q_6$:G and T:G lanes.

The low amount of MK product seen in the $Q_6$ $10^{-4}$ and $10^{-5}$ MK lanes (FIG. 13, $Q_6$:G lanes 6, 7) compared to the respective nonconversion control reactions, (FIG. 13,C:G lanes 2, 3) may be due to low efficiency of MK conversion. The production of a TaqI site actually requires two conversions, one on each side of the central CpG dinucleotide. Lowering the concentration of MK 10-fold may reduce MK conversion far more than 10-fold. Thus, with only one side of the MK sequence converted in a large amount of its product, one half of the LDR probes will be unable to properly hybridize to this sequence and ligation will not occur. LDR detection will only reveal the lesser quantity of fully converted template. Nevertheless, the amount of MK product is greater than the control in these two lanes. Compare FIG. 13, lane 8 to FIG. 13, lanes 6 and 7. While formamide may reduce conversion efficiency, conversion fidelity is greatly improved.

Newton et al., "Analysis of Any Point Mutation in DNA. The Amplification Refractory Mutation System (ARMS)," *Nucleic Acids Res.* 17(7):2503–16 (1989) found that C•T, A•A, and T•T mismatches were all far more difficult to extend with Taq polymerase than purine-pyrimidine mismatches. These results reflect PCR efficiency of extension rather than fidelity. Others have observed low fidelity in extending natural base mismatches (O'Dell et al., *Genome Res.* 6(6):558–68 (1996); and Eiken et al., "Application of Natural and Amplification Created Restriction Sites for the Diagnosis of PKU Mutations," *Nucleic Acids Res.*, 19(7): 1427–30 (1991)). Use of a nucleotide analog with structural similarities to multiple bases could potentially be used to allow polymerase extension (reading) from the analog when paired with different bases and insertion of different bases opposite the analog (writing). For the purposes of the present invention, the efficiency of the preconversion process need not necessarily be high. However, successful conversion requires high PCR fidelity to ensure that only the bases targeted for conversion are altered. False-positive mutation artifacts will result from alterations of bases not targeted for conversion within the sequence probed for mutations. Preconversion using 3' $Q_6$ primers forming a $Q_6$:G mismatch avoids starting polymerase extension with a G•T mismatch. In subsequent amplification cycles, A is apparently written frequently opposite $Q_6$. This observation is consistent with the results of Hill et al. in which $Q_6$ base-paired like C and T with nearly equal frequency (Hill et al., "Polymerase Recognition of Synthetic Oligodeoxyribonucleotides Incorporating Degenerate Pyrimidine and Purine Bases," *Proc. Natl. Acad. Sci. USA,* 95(8):4258–63 (1998)). Facile tautomerization allows $Q_6$ to mimic either pyrimidine when base-paired and avoids mismatch wobble. When the natural base primer is added after preconversion, a significant quantity of perfect match template already exists, otherwise the MK artifact would appear in the reaction regardless of preconversion. Other nucleotide analogs in addition to $Q_6$ may serve as a bridge for more efficient conversions (Day et al., *Nucleic Acids Res.,* (1999)).

The fidelity of polymerase extension from primers in PCR has been measured, and conditions were found, which in some cases improve fidelity. Presumably, higher fidelity resulted from a decrease in polymerase misincorporation, primer slippage, and template degradation. PCR/RE/LDR allows the measurement of very low-level "mutant" sequences by preferentially amplifying non-wild-type sequences. The method of the present invention clearly demonstrates that natural base mismatch primer extension cannot be used as a general technique to create restriction sites at will in any sequence for RFLP analysis. As shown in FIG. 13 and observed previously (O'Dell et al., *Genome Res.,* 6(6):558–68 (1996); and Eiken et al., "Application of Natural and Amplification Created Restriction Sites for the Diagnosis of PKU Mutations," *Nucleic Acids Res.,* 19(7):1427–30 (1991)), natural base mismatch extension is prone to error. To perfectly engineer a restriction site from existing sequence, an error-free approach is required. The results of these examples, using the method of the present invention, indicates that the use of nucleotide analogs combined with high fidelity PCR conditions may radically decrease errors. Monitoring the true specificity of primer extension was possible in these studies because LDR can measure specific PCR errors accurately and with high sensitivity. Thus, the products of different polymerases and buffers could be assayed at different steps during PCR/RE/LDR to maximize both PCR efficiency and fidelity. As a result, a PCR/RE/LDR strategy could be assembled to achieve the goal of 105 sensitivity. However, this highest sensitivity was achieved only in the special case of no conversion at a preexisting MspI site. At this time, primer slippage remains an important mechanism through which mismatch primer extension errors can arise (Day et al., *Nucleic Acids Res.,* (1999)). Although the importance of this source of error in vivo is uncertain, it may have a dramatic impact on allele-specific PCR and other in vitro methods of mutation detection. An additional source of error arises from using natural base primers to select specific sequences for amplification following preconversion with nucleotide analogs. This is because a fraction of the selective natural base primers may form a mismatched pair with bases other than the intended base. It is known that a characteristic set of different bases insert opposite nucleotide analogs (Day et al., *Nucleic Acids Res.,* (1999); and Hill et al., "Polymerase Recognition of Synthetic Oligodeoxyribonucleotides Incorporating Degenerate Pyrimidine and Purine Bases," *Proc. Natl. Acad. Sci. USA,* 95(8):4258–63 (1998)). Thus, a high fidelity mismatch primer extension protocol awaits the development of new convertides that can overcome these problems. In combination with high fidelity PCR and LDR monitoring of efficiency, mismatch primer extension may become a technique for the precise introduction of desired mutations without artifacts.

Although the invention has been described in detail for the purpose of illustration, it is understood that such details are solely for that purpose. The variations can be made therein by those skilled in the art without departing from the spirit of the scope of the invention which is defined by the following claims.

What is claimed:

1. A method for identifying one or more low abundance sequences differing by one or more single-base changes, insertions, or deletions from a high abundance sequence, in a sample containing a plurality of target nucleotide sequences comprising:

providing a sample potentially containing one or more low abundance target nucleotide sequences with at least one sequence difference each from the high abundance target sequences;

providing a primary oligonucleotide primer set characterized by (a) a first oligonucleotide primer containing a target-specific portion, and (b) a second oligonucleotide primer containing a target-specific portion, wherein the primary oligonucleotide primers hybridize to complementary strands of high and low abundance target nucleotide sequences to permit formation of a polymerase chain reaction product, but have a mismatch which interferes with formation of such a polymerase chain reaction product when hybridized to any other nucleotide sequence present in the sample;

providing a polymerase;

blending the sample, the primary oligonucleotide primers, and the polymerase to form a primary polymerase chain reaction mixture;

subjecting the primary polymerase chain reaction mixture to two or more polymerase chain reaction cycles;

providing a secondary oligonucleotide primer set characterized by (a) a first oligonucleotide primer, having a target-specific portion and a 5' upstream secondary primer-specific portion, and (b) a second oligonucleotide primer, having a target-specific portion and a 5' upstream secondary primer-specific portion, wherein the secondary oligonucleotide primers in a particular set hybridize to complementary strands of the primary extension products to permit formation of a secondary polymerase chain reaction product which contains or creates a restriction endonuclease recognition site when amplifying the high abundance target, but does not contain or create a restriction endonuclease recognition site when amplifying the one or more low abundance targets;

providing a polymerase;

blending the primary extension products, the secondary oligonucleotide primers, and the polymerase to form a secondary polymerase chain reaction mixture;

subjecting the secondary polymerase chain reaction mixture to two or more polymerase chain reaction cycles, wherein high abundance secondary extension products contain a restriction site but low abundance secondary extension products do not;

providing a restriction endonuclease;

blending the secondary extension product and the restriction endonuclease to form an endonuclease digestion reaction mixture;

subjecting the endonuclease digestion reaction mixture to an endonuclease digestion reaction such that the restriction endonuclease recognizes and cleaves the restriction endonuclease recognition site contained within or created when amplifying the high abundance target but not the low abundance target in the secondary extension products, thus selectively destroying the high abundance secondary extension products;

providing a tertiary oligonucleotide primer set characterized by (a) a first tertiary primer containing the same sequence as the 5' upstream portion of the first oligonucleotide primer of the secondary oligonucleotide primer set, and (b) a second tertiary primer containing the same sequence as the 5' upstream portion of a second oligonucleotide primer of the secondary oligonucleotide primer set, wherein the set of tertiary oligonucleotide primers are amplification primers for amplification of all the secondary extension products;

blending the secondary extension products, the tertiary oligonucleotide primer set, and the polymerase to form a tertiary polymerase chain reaction mixture;

subjecting the tertiary polymerase chain reaction mixture to two or more polymerase chain reaction cycles;

providing a plurality of oligonucleotide probe sets, each set characterized by (a) a first oligonucleotide probe, having a tertiary extension product-specific portion and a detectable reporter label, and (b) a second oligonucleotide probe, having a tertiary extension product-specific portion, wherein the oligonucleotide probes in a particular set ligate together when hybridized adjacent to one another on a complementary tertiary extension product-specific portion, but have a mismatch which interferes with said ligation when hybridized to any other nucleotide sequence present in the sample;

providing a ligase;

blending the tertiary extension product, the plurality of oligonucleotide probe sets, and the ligase to form a ligase detection reaction mixture;

subjecting the ligase detection reaction mixture to one or more ligase detection reaction cycles comprising a denaturation treatment, wherein any hybridized oligonucleotides are separated from the tertiary extension products, and a hybridization treatment, wherein the oligonucleotide probe sets hybridize at adjacent positions in a base-specific manner to their respective tertiary extension products, if present, and ligate to one another to form a ligation product sequence containing (a) the detectable reporter label and (b) the tertiary extension product-specific portions connected together, wherein the oligonucleotide probe sets may hybridize to nucleotide sequences other than their respective complementary tertiary extension products but do not ligate together due to a presence of one or more mismatches and individually separate during the denaturation treatment; and detecting the reporter labels of the ligation product sequences, thereby identifying the presence of one or more low abundance target nucleotide sequences in the sample.

2. A method according to claim 1, wherein the oligonucleotide probes in an oligonucleotide probe set have a unique length whereby the ligation product sequences which they form are distinguished from other ligation product sequences, said method comprising:

separating the ligation product sequences by electrophoretic mobility prior to said detecting and distinguishing, after said detecting, the ligation product sequences which differ in electrophoretic mobility.

3. A method according to claim 1, wherein the second oligonucleotide probe of each oligonucleotide probe set further comprises an addressable array-specific portion, said method further comprising:

providing a solid support comprising an array of address-specific capture oligonucleotides, and contacting the ligase detection reaction mixture, after said subjecting it to one or more ligase detection reaction cycles, with the solid support to hybridize the ligation product sequences to the capture oligonucleotides in a base-specific manner, thereby capturing the addressable array-specific portions to the solid support at the site with the complementary capture oligonucleotide, wherein said detecting identifies the presence of ligation product sequences captured using the addressable array-specific portions and immobilized to the solid support at particular sites, thereby identifying the presence of one or more target nucleotide sequences in the sample.

4. A method according to claim 1 further comprising:

quantifying the amount of the low abundance sequence, wherein said quantifying comprises:

providing a known amount of one or more marker target nucleotide sequences as an internal standard;

providing one or more internal standard sequence-specific oligonucleotide probe sets specifically designed for hybridization to the internal standard, wherein the internal standard sequence-specific oligonucleotide probe sets have (1) a first oligonucleotide probe with a target-specific portion complementary to the marker target nucleotide sequence, and (2) a second oligonucleotide probe with a target-specific portion complementary to the marker target nucleotide sequence and a detectable reporter label;

blending the internal standard, and the internal standard sequence-specific probe sets, with the ligase detection reaction mixture; and quantifying the amount of ligation product sequences by comparing the amount of ligation product sequences generated from the unknown low abundance sample to the amount of ligation product sequences generated from said internal standard to provide a quantitative measure of one or more low abundance target nucleotide sequences in the sample.

5. A method according to claim 4, wherein one or more low abundance sequence is present in less than a 1:1,000 molar ratio relative to the amount of the high abundance sequence present in the sample.

6. A method according to claim 4, wherein one or more low abundance sequence is present in less than a 1:10,000 molar ratio relative to the amount of the high abundance sequence present in the sample.

7. A method according to claim 4, wherein one or more low abundance sequence is present in less than a 1:100,000 molar ratio relative to the amount of the high abundance sequence present in the sample.

8. A method according to claim 1, wherein prior to providing the secondary oligonucleotide primer set, said method comprises:

providing a pre-secondary oligonucleotide primer set characterized by (a) a first oligonucleotide primer, having a target-specific portion, and (b) a second oligonucleotide primer, having a target-specific portion, wherein the target-specific portions are identical or substantially identical to the secondary oligonucleotide primer set but at least one primer contains one or more nucleotide analogs, wherein the oligonucleotide primers in a particular pre-secondary oligonucleotide primer set hybridize to complementary strands of the primary extension products to form a pre-secondary polymerase chain reaction product which contains one or more nucleotide analogs and opposite strand base changes, wherein the pre-secondary oligonucleotide primer set facilitates conversion of the primary polymerase chain reaction product sequence into a restriction endonuclease recognition site in the subsequent secondary polymerase chain reaction;

providing a polymerase;

blending the primary extension products, the pre-secondary oligonucleotide primers, and the polymerase to form a pre-secondary polymerase chain reaction mixture;

subjecting the pre-secondary polymerase chain reaction mixture to two or more polymerase chain reaction cycles comprising a denaturation treatment, wherein hybridized nucleic acid sequences are separated, a hybridization treatment, wherein the pre-secondary oligonucleotide primers hybridize to the primary extension products, an extension treatment, wherein the hybridized pre-secondary oligonucleotide primers are extended to form pre-secondary extension products complementary to the primary extension products, wherein the pre-secondary extension products contain one or more nucleotide analogues and opposite strand base changes which facilitate conversion of the primary polymerase chain reaction product sequence into a restriction endonuclease recognition site in the subsequent secondary polymerase chain reaction, wherein the pre-secondary extension products are then used in place of the primary extension products in the secondary polymerase chain reaction mixture, whereby the efficiency and accuracy of converting the high abundance primary polymerase chain reaction product into a secondary polymerase chain reaction product containing a restriction endonuclease site is improved.

9. A method according to claim 8, wherein the oligonucleotide probes in an oligonucleotide probe set have a unique length whereby the ligation product sequences which they form are distinguished from other ligation product sequences, said method further comprising:

separating the ligation product sequences by electrophoretic mobility prior to said detecting and distinguishing, after said detecting, the ligation product sequences which differ in electrophoretic mobility.

10. A method according to claim 8, wherein the second oligonucleotide probe of each set further comprises an addressable array-specific portion, said method further comprising:

providing a solid support comprising an array of address-specific capture oligonucleotides and contacting the ligase detection reaction mixture, after said subjecting it to one or more ligase detection reaction cycles, with the solid support to hybridize the ligation product sequences to the capture oligonucleotides in a base-specific manner, thereby capturing the addressable array-specific portions to the solid support at the site with the complementary capture oligonucleotide, wherein said detecting identifies the presence of ligation product sequences captured using the addressable array-specific portions and immobilized to the solid support at particular sites, thereby identifying the presence of one or more target nucleotide sequences in the sample.

11. A method according to claim 8 further comprising:

quantifying the amount of low abundance sequence, wherein said quantifying comprises:

providing a known amount of one or more marker target nucleotide sequences as an internal standard;

providing one or more internal standard sequence-specific oligonucleotide probe sets specifically designed for hybridization to the internal standard, wherein the internal standard sequence-specific oligonucleotide probe sets have (1) a first oligonucleotide probe with a target-specific portion complementary to the marker target nucleotide sequence, and (2) a second oligonucleotide probe with a target-specific portion complementary to the marker target nucleotide sequence and a detectable reporter label;

blending the internal standard and the internal standard sequence-specific probe sets with the ligase detection reaction mixture; and quantifying the amount of ligation product sequences by comparing the amount of ligation product sequences generated from the unknown low abundance sample to the amount of ligation product sequences generated from said internal standard to provide a quantitative measure of one or more low abundance target nucleotide sequences in the sample.

12. A method according to claim 11, wherein one or more of a low abundance sequence is present in a molar ratio of than less than 1:1,000 relative to the amount of the high abundance sequence in the sample.

13. A method according to claim 11, wherein one or more of a low abundance sequence is present in a molar ratio of than less than 1:10,000 relative to the amount of the high abundance sequence in the sample.

14. A method according to claim 11, wherein one or more of a low abundance sequence is present in a molar ratio of than less than 1:100,000 relative to the amount of the high abundance sequence in the sample.

15. A method according to claim 8, where the nucleotide analog of at least one oligonucleotide primer of the pre-secondary oligonucleotide primer set is at the 3' end of the primer.

16. A method according to claim 8, where the nucleotide analog is selected from the group consisting of 1-(2'-deoxy-β-D-ribofuranosyl)imidazole-4-carboxamide, 1-(2'-deoxy-β-D-ribofuranosyl)-3-nitropyrrole, 2'-deoxyinosine, 6-(2'-deoxy-β-D-ribofuranosyl)-6H,8H-3,4-dihydropyrimido[4,5-c][1,2]oxazine-7-one, 2-amino-7-(2'-deoxy-β-D-ribofuranosyl)-6-methoxyaminopurine, 1-(2'-deoxy-β-D-ribofuranosyl)-4-iodopyrazole, 1-(2'-deoxy-β-D-ribofuranosyl)pyrrole-3-carboxamide, and 1-(2'-deoxy-β-D-ribofuranosyl)-4-nitropyrazole.

17. A method according to claim 1 further comprising:

blending the ligation product sequences and the restriction endonuclease, wherein the restriction endonuclease recognizes and cleaves the restriction endonuclease recognition site contained within any remaining high abundance target, thereby selectively destroying the high abundance tertiary extension products.

* * * * *